(12) United States Patent
Sporn et al.

(10) Patent No.: US 9,757,359 B2
(45) Date of Patent: *Sep. 12, 2017

(54) SYNTHETIC TRITERPENOIDS AND METHODS OF USE IN THE TREATMENT OF DISEASE

(71) Applicants: REATA PHARMACEUTICALS, INC., Irving, TX (US); TRUSTEES OF DARTMOUTH COLLEGE, Hanover, NH (US)

(72) Inventors: Michael B. Sporn, Turnbridge, VT (US); Karen T. Liby, West Lebanon, NH (US); Gordon W. Gribble, Lebanon, NH (US); Tadashi Honda, Port Jefferson Station, NY (US); Robert M. Kral, Grapevine, TX (US); Colin J. Meyer, Frisco, TX (US)

(73) Assignees: REATA PHARMACEUTICALS, INC., Irving, TX (US); TRUSTEES OF DARTMOUTH COLLEGE, Hanover, NH (US)

( * ) Notice: Subject to any disclaimer, the term of this patent is extended or adjusted under 35 U.S.C. 154(b) by 671 days.

This patent is subject to a terminal disclaimer.

(21) Appl. No.: 13/886,053

(22) Filed: May 2, 2013

(65) Prior Publication Data

US 2013/0345276 A1 Dec. 26, 2013

Related U.S. Application Data

(63) Continuation of application No. 13/359,381, filed on Jan. 26, 2012, now Pat. No. 8,455,544, which is a continuation of application No. 12/352,473, filed on Jan. 12, 2009, now Pat. No. 8,129,429.

(60) Provisional application No. 61/109,114, filed on Oct. 28, 2008, provisional application No. 61/020,624, filed on Jan. 11, 2008.

(51) Int. Cl.
| | |
|---|---|
| *A61K 31/21* | (2006.01) |
| *A61K 31/4174* | (2006.01) |
| *A61K 31/275* | (2006.01) |
| *A61K 31/4164* | (2006.01) |
| *A61K 31/277* | (2006.01) |

(52) U.S. Cl.
CPC ........ *A61K 31/4174* (2013.01); *A61K 31/275* (2013.01); *A61K 31/277* (2013.01); *A61K 31/4164* (2013.01)

(58) Field of Classification Search
CPC .............. A61K 31/4174; A61K 31/277; A61K 31/275; A61K 31/4164
USPC ................................ 514/399, 510
See application file for complete search history.

(56) References Cited

U.S. PATENT DOCUMENTS

| | | |
|---|---|---|
| 4,395,423 A | 7/1983 | Neumann |
| 5,248,807 A | 9/1993 | Fujimoto et al. |
| 5,603,958 A | 2/1997 | Morein et al. |
| 6,326,507 B1 | 12/2001 | Gribble et al. |
| 6,369,101 B1 | 4/2002 | Carlson |
| 6,552,075 B2 | 4/2003 | Gribble et al. |
| 6,642,217 B2 | 11/2003 | Krasutsky et al. |
| 6,649,654 B1 | 11/2003 | Karin et al. |
| 6,800,639 B2 | 10/2004 | Giles et al. |
| 6,974,801 B2 | 12/2005 | Honda et al. |
| 7,144,875 B2 | 12/2006 | Gibson et al. |
| 7,176,237 B2 | 2/2007 | Honda et al. |
| 7,288,568 B2 | 10/2007 | Gribble et al. |
| 7,399,606 B2 | 7/2008 | Karin et al. |
| 7,435,755 B2 | 10/2008 | Konopleva et al. |
| 7,678,830 B2 | 3/2010 | Honda et al. |
| 7,714,012 B2 | 5/2010 | Honda et al. |
| 7,795,305 B2 | 9/2010 | Konopleva et al. |
| 7,795,306 B2 | 9/2010 | Dev et al. |
| 7,863,327 B2 | 1/2011 | Gribble et al. |
| 7,915,402 B2 | 3/2011 | Anderson et al. |
| 7,943,778 B2 | 5/2011 | Jiang et al. |
| 8,034,955 B2 | 10/2011 | Gribble et al. |
| 8,067,394 B2 | 11/2011 | Honda et al. |
| 8,067,465 B2 | 11/2011 | Honda et al. |
| 8,071,632 B2 | 12/2011 | Jiang et al. |
| 8,088,824 B2 | 1/2012 | Walling et al. |
| 8,124,656 B2 | 2/2012 | Anderson et al. |
| 8,124,799 B2 | 2/2012 | Anderson et al. |
| 8,129,429 B2 | 3/2012 | Sporn et al. |
| 8,258,329 B2 | 9/2012 | Anderson et al. |
| 8,299,046 B2 | 10/2012 | Sporn et al. |
| 8,309,601 B2 | 11/2012 | Walling et al. |
| 8,314,137 B2 | 11/2012 | Honda et al. |

(Continued)

FOREIGN PATENT DOCUMENTS

| | | |
|---|---|---|
| CN | 102070697 | 5/2011 |
| JP | 55 055153 | 4/1980 |

(Continued)

OTHER PUBLICATIONS

Kolyada et al (Molecular Medicine, 2001, 7(5), 329-343, Abstract used).*

(Continued)

*Primary Examiner* — Jason Sims
*Assistant Examiner* — Ibrahim D Bori
(74) *Attorney, Agent, or Firm* — Parker Highlander PLLC

(57) ABSTRACT

The present invention concerns methods for treating and preventing renal/kidney disease, insulin resistance/diabetes, fatty liver disease, and/or endothelial dysfunction/cardiovascular disease using synthetic triterpenoids, optionally in combination with a second treatment or prophylaxis.

25 Claims, 15 Drawing Sheets

(56) References Cited

U.S. PATENT DOCUMENTS

| | | | |
|---|---|---|---|
| 8,338,618 B2 | 12/2012 | Jiang et al. | |
| 8,394,967 B2 | 3/2013 | Jiang et al. | |
| 8,440,820 B2 | 5/2013 | Anderson et al. | |
| 8,440,854 B2 | 5/2013 | Anderson et al. | |
| 8,455,544 B2 | 6/2013 | Sporn et al. | |
| 8,513,436 B2 | 8/2013 | Anderson et al. | |
| 8,586,775 B2 | 11/2013 | Gribble et al. | |
| RE45,288 E | 12/2014 | Anderson et al. | |
| RE45,325 E | 1/2015 | Anderson et al. | |
| 8,993,640 B2 | 3/2015 | Anderson et al. | |
| 9,000,188 B2 | 4/2015 | Honda et al. | |
| 2002/0042535 A1 | 4/2002 | Gribble et al. | |
| 2003/0119732 A1 | 6/2003 | Konopleva et al. | |
| 2003/0232786 A1 | 12/2003 | Honda et al. | |
| 2003/0236303 A1 | 12/2003 | Gribble et al. | |
| 2004/0002463 A1* | 1/2004 | Honda | A61K 31/275 514/25 |
| 2004/0097436 A1 | 5/2004 | Krasutsky et al. | |
| 2005/0142199 A1* | 6/2005 | Tian | A61K 9/2018 424/472 |
| 2005/0208151 A1 | 9/2005 | Hurez et al. | |
| 2005/0288363 A1 | 12/2005 | Gribble et al. | |
| 2007/0155742 A1 | 7/2007 | Honda et al. | |
| 2007/0244081 A1 | 10/2007 | Krasutsky et al. | |
| 2007/0249561 A1 | 10/2007 | Taylor | |
| 2008/0220057 A1 | 9/2008 | Gribble et al. | |
| 2008/0233195 A1 | 9/2008 | Spoorn et al. | |
| 2008/0261985 A1 | 10/2008 | Honda et al. | |
| 2009/0036524 A1 | 2/2009 | Dev et al. | |
| 2009/0048204 A1 | 2/2009 | Walling et al. | |
| 2009/0048205 A1 | 2/2009 | Meyer et al. | |
| 2009/0060873 A1 | 3/2009 | Sporn et al. | |
| 2009/0093447 A1 | 4/2009 | Konopleva et al. | |
| 2009/0326063 A1 | 12/2009 | Sporn et al. | |
| 2010/0041904 A1 | 2/2010 | Jiang et al. | |
| 2010/0048887 A1 | 2/2010 | Anderson et al. | |
| 2010/0048892 A1 | 2/2010 | Anderson et al. | |
| 2010/0048911 A1 | 2/2010 | Jiang et al. | |
| 2010/0056777 A1 | 3/2010 | Anderson et al. | |
| 2010/0261930 A1 | 10/2010 | Honda et al. | |
| 2011/0009363 A1 | 1/2011 | Honda et al. | |
| 2011/0196007 A1 | 8/2011 | Honda et al. | |
| 2011/0245206 A1 | 10/2011 | Jiang et al. | |
| 2011/0245233 A1 | 10/2011 | Anderson et al. | |
| 2011/0281955 A1 | 11/2011 | Meyer et al. | |
| 2012/0022156 A1 | 1/2012 | Zhang et al. | |
| 2012/0071684 A1 | 3/2012 | Walling et al. | |
| 2012/0101149 A1 | 4/2012 | Honda et al. | |
| 2012/0196880 A1 | 8/2012 | Anderson et al. | |
| 2012/0214814 A1 | 8/2012 | Anderson et al. | |
| 2012/0220652 A1 | 8/2012 | Sporn et al. | |
| 2012/0238767 A1 | 9/2012 | Jiang et al. | |
| 2012/0245374 A1 | 9/2012 | Anderson et al. | |
| 2012/0252776 A1 | 10/2012 | Anderson et al. | |
| 2012/0283450 A1 | 11/2012 | Anderson et al. | |
| 2013/0237721 A1 | 9/2013 | Gribble et al. | |
| 2013/0274480 A1 | 10/2013 | Honda et al. | |
| 2013/0317007 A1 | 11/2013 | Anderson et al. | |
| 2013/0324599 A1 | 12/2013 | Anderson et al. | |
| 2013/0345276 A1 | 12/2013 | Sporn et al. | |
| 2014/0051739 A1 | 2/2014 | Anderson et al. | |
| 2014/0066408 A1 | 3/2014 | Jiang et al. | |
| 2014/0073700 A1 | 3/2014 | Wagner et al. | |
| 2014/0088163 A1 | 3/2014 | Jiang et al. | |
| 2014/0088188 A1 | 3/2014 | Jiang et al. | |
| 2014/0100227 A1 | 4/2014 | Bender et al. | |
| 2014/0179928 A1 | 6/2014 | Anderson et al. | |
| 2014/0275618 A1 | 9/2014 | Gribble et al. | |
| 2015/0080465 A1 | 3/2015 | Chen et al. | |

FOREIGN PATENT DOCUMENTS

| | | |
|---|---|---|
| JP | 2001 240573 | 9/2001 |
| JP | 2005-314381 | 11/2005 |
| JP | 2008 110962 | 5/2008 |
| JP | 2008 247898 | 10/2008 |
| WO | WO 99/65478 | 12/1999 |
| WO | WO 00/73253 | 12/2000 |
| WO | WO 02/03996 | 1/2002 |
| WO | WO 02/32410 | 4/2002 |
| WO | WO 02/47611 | 6/2002 |
| WO | WO 02/092768 | 11/2002 |
| WO | WO 03/059339 | 7/2003 |
| WO | WO 2004/064723 | 8/2004 |
| WO | WO 2004/089357 | 10/2004 |
| WO | WO 2004/105517 | 12/2004 |
| WO | WO 2005/042002 | 5/2005 |
| WO | WO 2005/046732 | 5/2005 |
| WO | WO 2005/113761 | 12/2005 |
| WO | WO 2006/029221 | 3/2006 |
| WO | WO 2007/005879 | 6/2007 |
| WO | WO 2007/069895 | 6/2007 |
| WO | WO 2007/112043 | 10/2007 |
| WO | WO 2007/127791 | 11/2007 |
| WO | WO 2008/000068 | 1/2008 |
| WO | WO 2008/000070 | 1/2008 |
| WO | WO 2008/016095 | 2/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/059245 | 5/2010 |
| WO | WO 2010/093944 | 8/2010 |
| WO | WO 2011/130302 | 10/2011 |
| WO | WO 2012/125488 | 9/2012 |
| WO | WO 2013/163344 | 10/2013 |
| WO | WO 2013/188818 | 12/2013 |
| WO | WO 2014/040056 | 3/2014 |
| WO | WO 2014/040060 | 3/2014 |
| WO | WO 2014/040073 | 3/2014 |
| WO | WO 2014/176415 | 11/2014 |
| WO | WO 2015/027206 | 2/2015 |

OTHER PUBLICATIONS

Alabran, et al., "Human neuroblastoma cells rapidly enter cell cycle arrest and apoptosis following exposure to C-28 derivatives of the synthetic triterpenoid CDDO," *Cancer Biology & Therapy*, 7(5):709-717, 2008.

Chadalapaka, et al., "Structure-dependent inhibition of bladder and pancreatic cancer cell growth by 2-substituted glycyrrhetinic and ursolic acid derivatives," *Bioorganic & Medicinal Chemistry Letters*, 18:2633-2639, 2008.

Deeb, et al., "CDDO-ME inhibits proliferation, induces apoptosis, down-regulates Akt, mTOR, NF-κB and NF-κB-regulated antiapoptotic and proangiogenic proteins in TRAMP prostate cancer cells," *J. of Experimental Therapeutics and Oncology*, 7:31-39, 2008.

Heather E. Ferguson, "PPARγ ligands have potent anti-fibrotic activity: mechanism of action and implications for therapy of pulmonary fibrosis," Dissertation, University of Rochester, 2008.

Hughes, et al., "The synthetic triterpenoid CDDO-Im inhibits fatty acid synthase expression and has antiproliferative and proapoptotic effects in human liposarcoma cells," *Cancer Investigation*, 26:118-127, 2008.

Hyer, et al., "Apoptotic activity and mechanism of 2-cyano-3,12-dioxoolean-1,9-dien-28-oic acid and related synthetic triterpenoids in prostate cancer," *Cancer Res.*, 68:2927-2933, 2008.

(56) References Cited

OTHER PUBLICATIONS

Liu, et al., "Coordinate regulation of enzyme markers for inflammation and for protection against oxidants and electrophiles," *Proc. Natl. Acad. Sci.*, 105(41):15926-15931, 2008.
Andrew E. Place, "Pre-clincial evaluation of the novel synthetic triterpenoid CDDO-Imidazolide," Thesis, Dartmouth College, May 5, 2004.
Riccioni, et al., "Resistance of acute myeloid leukemic cells to the triterpenoid CDDO-Imidazolide is associated with low caspase-8 and FADD levels," *Leukemia Research*, 32:1244-1258, 2008.
Samudio, et al., "Inhibition of mitochondrial metabolism by methyl-2-cyano-3,12-dioxoolean-1,9-diene-28-oate induces apoptotic or autophagic cell death in chronic myelogenous leukemia cells," *Mol. Cancer Ther.*, 7(5):1130-1139, 2008.
Subba Rao, et al., "Chemical modifications of natural triterpenes—glycyrrhetinic and boswellic acids: evaluation of their biological activity," *Tetrahedron*, 64(51):11541-11548, 2008.
Sun, et al., "Therapeutic potential of synthetic triterpenoids in neuroblastoma," *Cancer Biology & Therapy*, 7(5):720-722, 2008.
To, et al., "The synthetic triterpenoid 2-cyano-3,12-dioxooleana-1,9-dien-28-oic acid-imidazolide alters transforming growth factor β-dependent signaling and cell migration by affecting the cytoskeleton and the polarity complex," *J. Biol. Chem.*, 283:11700-11713, 2008.
Venè, et al., "Glycogen synthase kinase 3β regulates cell death induced by synthetic triterpenoids," *Cancer Res.*, 68:6987-6996, 2008.
Wang, "Differentiating and anti-inflammatory activities of the triterpenoid, CDDO," Thesis, Dartmouth College, May 4, 2001.
Wen, et al., "Naturally occurring pentacyclic triterpenes as inhibitors of glycogen phosphorylase: synthesis, structure-activity relationships, and X-ray crystallographic studies," *J. Med. Chem.*, 51:3540-3554, 2008.
Xu, et al., "Inhibition of the signal transducer and activator of transcription-3 (STAT3) signaling pathway by 4-oxo-l-phenyl-1,4-dihydroquinoline-3-carboxylic acid esters," *J. Med. Chem.*, 51:4115-4121, 2008.
Zou, et al., "c-FLIP downregulation contributes to apoptosis induction by the novel synthetic triterpenoid methyl-2-cyano-3,12-dioxooleana-1,9-dien-28-oate (CDDO-Me) in human lung cancer cells," *Cancer Biology & Therapy*, 6(10):1614-1620, 2007.
Zou, et al., "Coupling of endoplasmic reticulum stress to CDDO-Me-induced up-regulation of death receptor 5 via a CHOP-dependent mechanism involving JNK activation," *Cancer Res.*, 68:7484-7492, 2008.
Abraham and Kappas, "Heme oxygenase and the cardiovascular-renal system", *Free Radic. Biol. Med.*, 2005, 39(1):1-25.
Agodoa, et al., "Effect of ramipril vs. amlodipine on renal outcomes in hypertensive nephrosclerosis", *JAMA*, 2001, 285:2719-2728.
Ahmad, et al., "Triterpenoid CDDO-Me blocks the NF-κB pathway by direct inhibition of IKKβ on Cys-179", *J. Biol. Chem.*, 2006, 281:35764-35769.
Ahmad, et al., "Triterpenoid CDDO-methyl ester inhibits the Janus-activated kinase-1 (JAK1) signal transducer and activator of transcription-3 (STAT3) pathway by direct inhibition of JAK1 and STAT3", *Cancer Res.*, 2008, 68(8): 2920-2926.
Albini and Sporn, "Opinion: the tumour microenvironment as a target for chemoprevention", *Nature Reviews Cancer*, 2002, Abstract 501:149.
Ambs, et al., "p53 and vascular endothelial growth factor regulate tumor growth of NOS2-expressing human carcinoma cells", *Nat. Med.*, 1998, 4(12):1371-1376.
Andreef, et al., "PPARγ nuclear receptor as a novel molecular target in leukemias", 2002 Keystone Symposia, 2002, Abstract 501:149.
Araujo, et al., "Systemic rather than local heme oxygenase-1 overexpression improves cardiac allograft outcomes in a new transgenic mouse", *J. Immunol.*, 2003, 171(3):1572-1580.
Ardestani, et al., "Effects of dexamethasone and betamethasone as COX-2 gene expression inhibitors on rigidity in a rat model of Parkinson's disease", *Indian J. Pharmacol.*, 2007, 39:235-9.
Arend, et al., "Interleukin-1 receptor antagonist: role in biology", *Annu. Rev. Immunol.*, 1998, 16:27-55.
Arkan, et al., "IKK-β links inflammation to obesity-induced insulin resistance", *Nat. Med.*, 2005, 11(2):191-198.
Aschner, et al., "Effect of the dipeptidyl peptidase-4 inhibitor sitagliptin as monotherapy on glycemic control in patients with type 2 diabetes", *Diabetes Care*, 2006, 29(12):2632-2637.
Awale, et al., "Inhibition of NO production by highly-oxygenated diterpenes of *Orthosiphon stamineus* and their structure-activity relationship", *Biological and Pharmaceutical Bulletin*, 2003, 26(4):468-473.
Bach, et al., "Heine oxygenase-1 and transplantation tolerance", *Hum. Immun.*, 2006, 67(6):430-432.
Baeuerle, et al., "NF-κB: ten years after", *Cell*, 1996, 87:13-20.
Bagasra, et al., "Activation of the inducible form of nitric oxide synthase in the brains of patients with multiple sclerosis", *Proc. Natl. Acad. Sci. USA*, 1995, 92:12041-12045.
Balwdin, et al., "The NF-κB and IκB proteins: new discoveries and insights", *Annu. Rev. Immunol.*, 1996, 14:649-681.
Balkwill, et al., "Smoldering and polarized inflammation in the initiation and promotion of malignant disease", *Cancer Cell*, 2005, 7(3):211-217.
Ballesta-Acosta, et al., "A new 24-nor-oleanane triterpenoid from *Salvia carduacea*", *J. Nat. Prod*, 2002, 65(10):1513-1515.
Bargou, et al., "Constitutive nuclear factor κB-RelA activatioin is required for porliferation and survival of Hodgkin's disease tumor cells", *J. Clin. Invest.*, 1997, 100:2961-2969.
Barkett and Gilmore, "Control of apoptosis by Rel/NF-κB transcription factors", *Oncogene*, 1999, 18:6910-6924.
Barnes and Karin, "Nuclear factor-κB—a pivotal transcription factor in chronic inflammation diseases", *N. Engl. J. Med.*, 1997, 336:1066-1071.
Beal, et al., "Mitochondria, free radicals, and neurodegeneration", *Curr. Opin. Neurobiol.*, 1996, 6:661-666.
Blann, et al., "Circulating endothelial cells: biomarker of vascular disease", *Throm. Haemost.*, 2005, 93:228-235.
Bore, et al., "The anti-inflammatory triterpenoid methyl 2-cyano-3,12-dioxoolean 1,9(11)-dien-28-oate methanol solvate hydrate", *Acta Crystallorg C.*, 2002, 58(Pt 3):o199-o200.
Bowden, et al., "Constituents of the fruit of *Pseudopanax arboretum* (Araliaceae)", *Australian Journal of Chemistry*, 1975, 28(1):91-107.
Brookes, et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore", *Cancer Res.*, 2007, 67:1793-18.
Brown and Dubois, "COX-2: a molecular target for colorectal cancer prevention", *J. Clin. Oncol.*, 2005, 23(12):2840-2855.
Buchanan, et al., "The conversion of turraeanthin and turraeanthin A into simple melaiacins by a route involving an oxidative rearrangement of probable biogenetic importance", *J. Chem. Soc. C*, 1970, 17:2280-2284.
Burger and Dayer, "Inhibitory cytokines and cytokine inhibitors", *Neurology*, 1995, 45(6S-6):S39-S43.
Buzoni-Gatel, et al., "Murine ileitis after intracellular parasite infection is controlled by TGF-β-producing intraepithelial lymphocytes", *Gastroenterology*, 2001, 120:914-924.
Cai, et al., "Local and systemic insulin resistance resulting from hepatic activation of IKKβ and NF-Kb", *Nature Medicine*, 2005, 11(2):183-190.
Chauhan, et al., "The bortezomib/proteasome inhibitor PS-341 and triterpenoid CDDO-Im induce synergistic anti-multiple myeloma (MM) activity and overcome bortezomib resistance", *Blood*, 2004, 103:3158-3166.
Chauhan and Chauhan, "Oxidative stress in autism", *Pathophysiology*, 2006, 13(3):171-181.
Chintharlapalli, et al., "2-Cyano-3,12-dioxoolean-1,9-dien-28-oic acid and related compounds inhibit growth of colon cancer cells through peroxisome proliferator-activated receptor γ-dependent and -independent pathways", *Mol. Pharmacol.*, 2005, 68:119-128.
Chintharlapalli, et al., "2-Cyano-lup-1-en-3-oxo-20-oic acid, a cyano derivative of betulinic acid, activates peroxisome prolifera-

(56) References Cited

OTHER PUBLICATIONS tor-activated receptor γ in colon and pancreatic cancer cells.", *Carcinogenesis*, 2007, 28(11):2337-2346.

Chintharlapalli, et al., "Structure-dependent activity of glycyrrhetinic acid derivatives as peroxisome proliferator-activated receptor γ agonists in colon cancer cells", *Molecular Cancer Therapeutics*, 2007, 6(5):1588-1598.

Cho, et al., "The transcription factor NRF2 protects against pulmonary fibrosis", *FASEB Journal*, 2004, 18:1-29.

Cianchi, et al., "Cyclooxygenase-2 activation mediates the proangiogenic effect of nitric oxide in colorectal cancer", *Clinical Cancer Research*, 2004, 10:2694-2704.

Clinicaltrials.gov Study Record, NCT 00352040, "CDDO in treating patients with metastatic or unresectable solid tumors or lymphoma conditions: lymphoma; small intestine cancer; unspecified adult solid tumor, protocol specifc", update of Jul. 6, 2009.

clinicaltrials.gov Study Record, NCT 00508807, "RTA 402 in advanced solid tumors or lymphoid malignancies", update as of Dec. 14, 2008.

clinicaltrials.gov Study Record, NCT 00508807, "RTA 402 in advanced solid tumors or lymphoid malignancies conditions: lymphoid malignancies; solid tumors", update of Aug. 27, 2008.

clinicaltrials.gov Study Record, NCT 00508807, "RTA 402 in advanced solid tumors or lymphoid malignancies conditions: lymphoid malignancies; solid tumors", update of Oct. 5, 2010.

clinicaltrials.gov Study Record, NCT 00529113, "Study with gemcitabine and RTA 402 for patients with unresectable pancreatic cancer", update of Dec. 1, 2010.

clinicaltrials.gov Study Record, NCT 00529113, "Study with gemcitabine and RTA 402 for patients with unresectable pancreatic cancer", update of Jun. 12, 2008.

clinicaltrials.gov Study Record, NCT 00529438, "RTA 402 in patients with advanced solid tumors or lymphoid malignancies conditions: advanced solid tumors; lymphoid malignancies", update of Dec. 21, 2008.

clinicaltrials.gov Study Record, NCT 00550849 , "Study to assess the safety, tolerability, and pharmacodynamics of RTA 402 in patients with hepatic dysfunction", Update as of Dec. 14, 2008.

clinicaltrials.gov Study Record, NCT 00550849, "Study to assess the safety, tolerability, and pharmacodynamics of RTA 402 in patients with hepatic dysfunction condition: liver disease", update of Nov. 6, 2007.

clinicaltrials.gov Study Record, NCT 00664027 , "Phase IIa trail to determine the effects of bardoxolone methyl on renal function in patients with diabetic nephropathy", update as of Dec. 14, 2008.

clinicaltrials.gov Study Record, NCT 00664027, "Phase IIa trial to determine the effects of bardoxolone methyl on renal function in patients with diabetic nephropathy condition: diabetic nephropathy", update of Feb. 18, 2009.

clinicaltrials.gov Study Record, NCT 00664027, "Phase IIa trial to determine the effects of bardoxolone methyl on renal function in patients with diabetic nephropathy condition: diabetic nephropathy", update of Jun. 25, 2011.

clinicaltrials.gov Study Record, NCT 00811889, "Trial to determine the effects of bardoxolone methyl on eGFR in patients with type 2 diabetes and chronic kidney disease conditions: chronic kidney disease; type 2 diabetes; diabetic nephropathy", update as Jun. 4, 2009.

clinicaltrials.gov Study Record, NCT0352040, "CDDO in treating patients with metastatic or unresectable solid tumors or lymphoma", Update as of Dec. 14, 2008.

Cohen, et al., "A general method for removal of a 4-methyl group from triterpenoids. Synthesis of 4beta-demethylgylycyrrhetinic acid", *J. Chem. Soc. Perkin Trans. 1*, 1973, 19:2076-2082.

Connolly, et al., "Grandiofolione: a novel tetranortriterpenoid", *Chemical Communications*, 1966, 23:567-568.

Couch, et al., "2-cyano-3,12-dioxooleana-1,9(11)-diene-28-oic Acid Disrupts Microtubule Polymerization: A Possible Mechanism Contributing to Apoptosis", *Molecular Pharmacology*, 2006, 69:1158-1165.

Couch, et al., "Studies on the reactivity of CDDO, a promising new chemopreventive and chemotherapeutic agent: implications for a molecular mechanism of action", *Bioorganic and Medicinal Chemistry Letters*, 2005, 15(9):2215-2219.

Crowell, et al., "Is inducible nitric oxide synthase a target for chemoprevention", *Mol. Cancer Ther.*, 2003, 2(8):815-823.

Cui, Yong, "A material sceince perspective of pharmaceutical solids", *Int. J. Pharmaceuticals*, 2007, 339:3-18.

Damsté, et al., "A sedimentary tetrahydrophenanthrene derivative of tetrahymanol", *Tetrahedron Letters*, 1999, 40(20):3949-3952.

Dean, et al., "Halogenolysis of methyl glycyrrhetate with lithium iodidedimethylformamide", *J. Chem. Soc.*, 1965, 6655-6659.

Deng and Synder, "Preparation of a 24-Nor-1,4-dien-3-one triterpene derivative from betulin: a new route to 24-nortriterpene analogues", *J. of Organic Chemistry*, 2002, 67(9):2864-2873.

Dezube, et al., "Interim results of a phase I trial with a novel orally administered synthetic triterpenoid RTA 402 (CDDO-Me) in patients with solid tumors and lymphoid malignancies", *J. Clin. Oncol.*, 2007 ASCO Annual Meeting Proceedings, 2007, 25(18S):14101.

Dickerson, et al., "Elevated serum levels of C-reactive protein are associated with mania symptoms in outpatients with bipolar disorder", *Prog. Neuropschopharmacol. Biol. Psychiatry*, 2007, 31(4):952-955.

Dinarello, et al., "Interleukin-1, interleukin-1 receptors and interleukin-1 receptor antagonist", *Int. Rev. Immunol.*, 1998, 16(5-6):457-499.

Ding, et al., "Macrophage deactivating factor and transforming growth factors-b1, b2, and b3, inhibit induction of macrophage nitrogen oxide synthesis by IFNg1", *J. Immunol.*, 1990, 145:940-944.

Dinkova-Kostova, et al., "Direct evidence that sulfhydryl groups of Keap1 are the sensors regulating induction of phase 2 enzymes that protect against carcinogens and oxidants", *Proc. Natl. Acad. Sci.*, 2002, 99(18):11908-11913.

Dinkova-Kostova, et al., "Extremely potent triterpenoid inducers of the phase 2 response: correlations of protection against oxidant and inflammatory stress", *Proc. Natl. Acad. Sci.*, 2005, 102(12):4584-4589.

Dirsch, et al., "The triterpenoid quinomethide pristimerin inhibits induction of inducible nitric oxide synthase in murine macrophages", *Eur. J. Pharmacol.*, 1997, 336(2-3):211-217.

Dracinsky, et al., "Preparation and Conformational Study of 19β,28-Epoxy-18α-olean-5-ene derivatives", *Collection of Czechoslovak Chemical Communications*, 2006, 71(3):387-410.

Dragnev, et al., "Specific chemopreventive agents trigger proteasomal degradation of G1 cyclins: implications for combination therapy", *Clin. Cancer Research*, 2004, 10(7): 2570-2577.

Duan, et al., "Di- and triterpenoids from *Triptergium hypoglaucum* Phytochemistry", *Phytochemistry*, 1997, 46(3):535-543.

Duan, et al., "Immunosuppressive terpenoids from extracts of *Tripterygium wilfordii*", *Tetrahedron*, 57(40): 8413-8424.

Eikelenboom, et al., "Neuroinflammation in Alzheimer's disease and prion disease", *Glia*, 2002, 40(2):232-239.

Ekmekcioglu, et al., "Tumor iNOS predicts poor survival for stage III melanoma patients", *Int. J. Cancer*, 2006, 119:861-866.

Ellies, et al al., "Mammary tumor latency is increased in mice lacking the inducible nitric oxide synthase", *Int. J. Cancer*, 2003, 106:1-7.

Elliot, et al., "The triterpenoid CDDO inhibits expression of matrix metalloproteinase-1, matrix metalloproteinase-13 and Bcl-3 in primary human chondrocytes", *Arthritis Res. Ther.*, 2003, 5:R285-R291.

Elsawa, et al., "Preferential Inhibition of Malignant Cell Growth by CDDO in *Waldenstrom Macroglobulinemia*", *Blood*, 2006, 108(11):2528.

Favaloro, Jr., Frank G. et al., "Design and Synthesis of Tricyclic Compounds with Enone Functionalities in Rings A and C: A Novel Class of Highly Active Inhibitors of Nitric Oxide Production in Mouse Macrophages", *J. Med Chem.*, 2002, 45(22):4801-4805.

Finlay, et al., "Novel A-ring cleaved analogs of oleanolic and ursolic acids which affect growth regulation in NRP.152 prostate cells", *Bioorg. Med. Chem. Lett.*, 1997, 7(13):1769-1772.

(56) References Cited

OTHER PUBLICATIONS

Finlay, et al., "The Effect of A and C Ring Modification of Oleanolic and Ursolic Acid on the Inhibition of Nitric Oxide Formation in Mouse Macrophages", 213th American Chemical Society National Meeting, Abstract:084, 1997.
Forstermann, "Janus-faced role of endothelial NO synthase in vascular disease: uncoupling of oxygen reduction from NO synthesis and its pharmacological reversal", Biol Chem., 2006, 387:1521-1533.
Gall, et al., "Risk factors for development of incipient and overt diabetic nephropathy in patients with non-insulin dependent diabetes mellitus: prospective, observational study", BMJ, 1997, 314:783-788.
Gallery and Webster, "The immuno-inflammatory cascade", Br. J. Anaesth., 1996, 77(1):11-16.
Gao, et al., "Synthetic triterpenoids inhibit growth and induce apoptosis in human glioblastoma and neuroblastoma cells through inhibition of prosurvival Akt, NF-κB and Notch1 signaling", J. of Neurooncology, 2007, 84(2):147-157.
Ghanim, et al., "Circulating mononuclear cells in the obese are in a proinflammatory state", Circulation, 2004, 110:1564-1571.
Ghosh, et al., "NF-κB and Rel proteins: evolutionarily conserved mediators of immune response", Annu. Rev. Immunol , 1998, 16:225-260.
Godoy, et al., "Central and systemic IL-1 exacerbates neurodegeneration and motor symptoms in a model of Parkinson's disease", Brain, 2008, 131:1880-1894.
Goldstein, et al., "Effect of initial combination therapy with sitagliptin, a dipeptidyl peptidase-4 inhibitor, and metformin on glycemic control in patients with type 2 diabetes", Diabetes Care, 2007, 30(8):1979-1987.
Goodman, et al., "Heme oxygenase-1 protects against radiocontrast-induced acute kidney injury by regulating anti-apoptotic proteins", Kidney Int., 2007, 72(8):945-953.
Greten, et al., "IKKβ links inflammation and tumorigenesis in a mouse model of colitis-associated cancer", Cell, 2004, 118(3):285-296.
Grieco and Speake, et al., "Synthetic Studies on Quassinoids: Total Synthesis and Biological Evaluation of (+)-Des-D-chaparrinone", J. Org. Chem., 1998, 63:5929-5936.
Grivennikov and Karin, "Dangerous Liaisons: STAT3 and NF-κB collaboration and crosstalk in cancer", Cytokine Growth Factor Rev., 2010, 21(1):11-19.
Guilherme, et al., "Adipocyte dysfunctions linking obesity to insulin resistance and type 2 diabetes", Nat. Rev. Mol. Cell. Biol., 2008, 9(5):367-377.
Guttridge, et al., "NF-κB controls cell growth and differentiation through transcription regulation of cyclin D1", Mol. Cell. Biol., 1999, 19(8):5785-5799.
Habeos, et al., "Simvastatin activates Keap1/Nrf2 signaling in rat liver", J. Mol. Med, 2008, 86(11):1279-85.
Hail, et al., "Evidence supporting a role for calcium in apoptosis induction by the synthetic triterpenoid 2-cyano-3,12-dioxooleana-1,9-dien-28-oic acid (CDDO)", J. Biol. Chem., 2004, 279:11179-11187.
Han, et al., "CDDO-Imidazolide inhibits growth and survival of c-Myc-induced mouse B cell and plasma cell neoplasms", Molecular Cancer, 2006, 5:22.
Hanson, et al., "Inflammation and atherosclerosis", Annu. Rev. Pathol: Mech. Dis., 2006, 1:297-329.
Hanson, et al., "Theories of schizophrenia: a genetic-inflammatory-vascular synthesis", BMC Medical Genetics, 2005, 6:7.
Hart, et al., "Comparison of the suppressive effects of interleukin-10 and interleukin-4 on synovial fluid macrophages and blood monocytes from patients with inflammatory arthritis", Immunology, 1995, 84(4):536-542.
He and Karin, "NF-κB and STAT3—key players in liver inflammation and cancer", Cell Research, 2011, 21:159-168.
Hill, et al., "Synthetical approaches to the pristimerin chromophore", J. of the Chemical Society, 1965, 361-375.

Hinz, et al., "NF-κb function in growth control: regulation of cyclin D1 expression and G0/G1-to-S-phase transition", Mol. Cell. Biol., 1999, 19(4):2690-2698.
Hirota, et al., "Suppression of tumor promoter-induced inflammation of mouse ear by ursolic acid and 4,4-dimethycholestane derivatives", Agric. Biol. Chem., 1990, 54:1073-1075.
Hirota, et al., "Total synthesis of (±)-amarolide, a quassinoid bitter principle", J. Org. Chem., 1991, 56:1119-1127.
Honda, et al., "A novel dicyanotriterpenoid, 2-cyano-3,12-dioxooleana-1,9(11)-dien-28-onitrile, active at picomolar concentrations for inhibition of nitric oxide production", Bioorg. Med. Chem. Lett., 2002, 12:1027-1030.
Honda, et al., "An efficient synthesis of tricyclic compounds (±)—(4aβ, 8aβ, 10βaa)—1,2,3,4,4a,6,7,8,8a,9,1-,10a-Dodecahydro-1,1,4a-Trimethy1-2-Oxophenanthrene-8a-Carboxolic acid, its methyl ester, and (±)-(4aβ,8aβ,10aα)-3,4,4a,6,7,8,8a,9,10,10a-Decahydro-8a-Hydroxymethy,—1,1,4a-Trimethylphenanthren-2(1H)-one," Org. Prep. Proced Int., 2005, 37(6):546-550.
Honda, et al., "Design and synthesis of 23,24-dinoroleanolic acid derivatives, novel triterpenoid—steroid hybrid molecules", J. Org. Chem., 1998, 63:4846-4849.
Honda, et al., "Design and synthesis of 2-cyano-3,12-dioxoolean-1,9-dien-28-oic acid, a novel and highly active inhibitor of nitric oxide production in mouse macrophages", Bioorg Med Chem Lett., 1998, 8(19):2711-2714.
Honda, et al., "Design, synthesis, and biological evaluation of biotin conjugates of 2-cyano-3,12-dioxooleana-1,9(11)-dien-28-oic acid for the isolation of the protein targets", J. Med. Chem., 2004, 47(20):4923-4932.
Honda, et al., "Efficient synthesis of (−)- and (+)-tricyclic compounds with enome functionalities in rings A and C. A novel class of orally active anti-inflammatory and cancer chemopreventive agents", Org Biomol Chem., 2003, 1:4384-4391.
Honda, et al., "New enone derivatives of oleanolic acid and ursolic acid as inhibitors of nitric oxide production in mouse macrophages", Bioorg. Med. Chem. Lett., 1997, 7:1623-1628.
Honda, et al., "New synthetic oleanane and ursane triterpenoids as inhibitors of nitric oxide production in mouse macrophages", The Fifth Chemical Congress of North America, Cancun, Mexico, Abstract 552 and slides for oral presentation, Nov. 1997.
Honda, et al., "Novel synthetic oleanane and ursane triterpenoids with various enone functionalities in ring A as inhibitors of nitric oxide production in mouse macrophages", J. Med. Chem., 2000, 43:1866-1877.
Honda, et al., "Novel synthetic oleanane triterpenoids: a series of highly active inhibitors of nitric oxide production in mouse macrophages", Bioorg. Med. Chem. Lett., 1999, 9(24):3429-3434.
Honda, et al., "Novel tricyclic compounds having acetylene groups at C-8a and cyano enones in rings A and C: highly potent anti-inflammatory and cytoprotective agents", J. Med. Chem., 2007, 50:1731-1734.
Honda, et al., "Revision and confirmation of the regiochemistry of isoxazoles derived from methyl oleanonate and lanost-8-en-3-one. Synthesis of a new lanostane triterpenoid with a cyano-enone functionality in ring A", J. Org. Chem., 2003, 68:4991-4993.
Honda, et al., "Synthesis of (±)-3,3-ethylenedioxy-14a-hydroxy-5-picrasene-11,16-dione, a 14aH-picrasane derivative", Chem. Lett., 1981, 299-302.
Honda, et al., "Synthesis of a novel dicyano abietane analogue: a potential antiinflammatory agent", J. Org. Chem., 2006, 71:3314-3316.
Honda, et al., "Synthetic oleanane and ursane triterpenoids with modified rings A and C: A series of highly active inhibitors of nitric oxide production in mouse macrophages", J. Med. Chem., 2000, 43:4233-4246.
Hong, et al., "Phase I trial of a novel oral NF-M3/pSTAT3 inhibitor RTA-402 in patients with solid tumors and lymphoid malignancies", 44th Annual Meeting of the American Society of Clinical Oncology, 2008.
Hotamisligil, et al., "Inflammation and metabolic disorders", Nature, 2006, 444(7121):960-967.

(56) References Cited

OTHER PUBLICATIONS

Hyer, et al., "Synthetic triterpenoids cooperate with tumor necrosis factor-related apoptosis-inducing ligand to induce apoptosis of breast cancer cells", *Cancer Res.*, 2005, 65:4799-4808.

Ikeda, et al., "Induction of redox imbalance and apoptosis in multiple myeloma cells by the novel triterpenoid 2-cyano-3,12-dioxoolean-1,9-dien-28-oic acid", *Mol. Cancer Ther.*, 2004, 3:39-45.

Ikeda, et al., "The novel triterpenoid CDDO and its derivatives induce apoptosis by disruption of intracellular redox balance", *Cancer Res.*, 2003, 63:5551-5558.

Ikeda, et al., "Triterpenoid CDDO-Im downregulates PML/RAR α-expression in acute promyelocytic leukemia cell", *Cell Death and Differentiation*, 2005, 12(5):523-531.

Inoue, et al., "CDDO induces apoptosis via the intrinsic pathway in lymphoid cells", *Leukemia*, 2004, 18(5):948-952.

Ishikawa, et al., "Heme oxygenase-1 inhibits atherogenesis in Watanabe heritable hyperlipidemic rabbits", *Circulation*, 2001, 104(15):1831-1836.

Ito, et al., "Involvement of caspase-8 in the induction of osteosarcoma cell apoptosis by the novel triterpenoid CDDO", 47th Annual Meeting, Orthopaedic Research Society, Feb. 25-28, 2001, San Francisco, California, 2001, p. 0863, Poster Session.

Ito, et al., "The novel triterpenoid 2-cyano-3,12-dioxoolean-1,9-dien-28-oic acid induces apoptosis of human myeloid leukemia cells by a caspase-8-dependent mechanism", *Cell Growth & Differentiation*, 2000, 11(5):261-267.

Ito, et al., "The novel triterpenoid CDDO induces apoptosis and differentiation of human osteosarcoma cells by a caspase-8 dependent mechanism", *Mol. Pharmacol.*, 2001, 59:1094-1099.

Jang, et al., "24-nor-ursane type triterpenoids from the stems of *Rumex japonicas*", *Chem. Pharm. Bull* (Tokyo), 2005, 53(12):1594-1596.

Ji, et al., "The synthetic triterpenoid CDDO-imidazolide induces monocytic differentiation by activating the Smad and ERK signaling pathways in HL60 leukemia cells", *Molecular Cancer Therapeutics*, 2006, 5(6):1452-1458.

Johansen, et al., "Pharmacology and preclinical pharmacokinetics of the triterpenoid CDDO methyl ester", *Proc. Amer. Assoc. Cancer. Res.*, 2003, 44:1728.

Joyce, et al., "Intergration of Rac-dependent regulation of cyclin D1 transcription through a nuclear factor-κB-dependent pathway", *J. Biol. Chem.*, 1999, 274(236):25245-25249.

Kaltschmidt, et al., "Transcription factor NF-κB is activated in primary neurons by amyloid beta peptides and in neurons surrounding early plaques from patients with Alzheimer disease", *Proc. Natl. Acad. Sci. USA*, 1997, 94:2642-2647.

Kamal, et al., "23-oxoisopristimerin III: an new natural phenolic (9→8)-24-nor-D:A-friedo-oleanane triterpene", *Tetrahedron Letters*, 1983, 24(27):2799-2800.

Kamal, et al., "Structures of two new phenolic 24-nor-D:A-friedoleananes related to zeylasterone: a partial synthesis of trimethylzeylasterone", *Tetrahedron Letters*, 1983, 24(19):2025-2028.

Kamal, et al., "The structure of zeylasterone, the first of a new series of phenolic 24-nor-D: A friedo-oleanane triterpenes", *Tetrahedron Letters*, 1980, 21(49):4749-4752.

Kansanen, et al., "Regulation of Nrf2-dependent gene expression by 15-deoxy-Δ12,14-prostaglandin J2", *Free Radic. Biol. Med.*, 2009, 47(9): 1310-1317.

Karin, et al., "NF-κB in cancer: From innocent bystander to major culprit", *Nature Reviews*, 2002, 2:301-303.

Karin, et al., "Nuclear factor -κB in cancer development and progression", *Nature*, 2006, 441(7092):431-436.

Kasinski, et al., "Inhibition of IκB kinase-nuclear factor-κB signaling pathway by 3,5-bis(2-fluorobenzylidene)piperidin-4-one (EF24), a novel monoketone analog of curcumin", *Mol. Pharmacology*, 2008, 74(3):654-661.

Kawakami, et al., "A comparative study of nitric oxide, glutathione, and glutathione peroxidase activities in cerebrospinal fluid from children with convulsive disease/children with aseptic meningitis", *Brain Dev.*, 2006, 28(4):243-246.

Kendall-Tackett, "Inflammation, cardiovascular disease, and metabolic syndrome as sequelae of violence against women: the role of depression, hostility, and sleep disturbance", *Trauma Violence Abuse*, 2007, 8(2):117-126.

Khalid, et al., "Isolation and characterization of pristimerin as the antiplasmodial and antileishmanial agent of *Maytenus senegalensis* (Lam.) Exell", *ARKIVOC*, 2007, 129-134.

Khan, et al., "A dichotomous role for nitric oxide during acute *Toxoplasma gondii* infection in mice", *Proc. Natl. Acad. Sci. USA*, 1997, 94:13955-13960.

Kim, et al., "An inducible Pathway for Degradation of FLIP protein Sensitizes Tumor Cells to TRAIL-induced Apoptosis", *J. Biological Chemistry*, 2002, 277(25):22320-22329.

Kim, et al., "Capasase-3 activation is Involved in Apoptosis Induced by a Synthetic Triterpenoid in Non-small Cell Lung Cancer (NSCLC) cells", *Proc. Amer. Assoc. Cancer. Res.*, 2000, 41:770, Abstract #4894.

Kim, et al., "Identification of a Novel Synthetic Triterpenoid, methyl-2-cyano-3,12-dioxooleana-1,9-dien-28-oate, that Potently Induces Caspace-mediated apoptosis in Human Lung Cancer Cells", *Molecular Cancer Therapeutics*, 2002, 1:177-184.

Klyne, et al., "The molecular rotations of polycyclic compounds. III. Polycyclic alcohols and their derivatives", *J. Chem. Soc.*, 1954, 1979-1988.

Kobayashi, et al., "The antioxidant defense system Keap1 -Nrf2 comprises a multiple sensing mechanism for responding to a wide range of chemical compounds", *Mol. Cell Biol.*, 2009, 29(2):493-502.

Kobayashi and Yamamoto, "Molecular mechanisms activating the Nrf2-Keap1 pathway of antioxidant gene regulation", *Antioxid. Redox. Signal.*, 2005, 7:385-394.

Kolak, et al., "Antioxidant and anticholinesterase constituents of *Salvia poculata*", *Turkish Journal of Chemistry*, 2009, 33(6):813-823.

Konopleva, et al., "Activation of nuclear transcription factor PPARγ by the novel triterpenoid CDDO as targeted therapy in breast cancer", 2002 Keystone Symposium, 2002, Abstract No. 539.

Konopleva, et al., "Mechanisms and Activity of PPARγ-Active Triterpenoids CDDO and CDDO-Me in Leukemias", *Blood*, 2005, 106:2460.

Konopleva, et al., "Novel synthetic triterpenoid CDDO-Me: potent antiproliferative, proapoptotic and differentiating agent in AML", *Blood*, 2000, 96(11), Part 1:121A, abstract #522.

Konopleva, et al., "Novel synthetic triterpenoid, CDDO, and its methyl ester: Potent antiproliferative, proapoptotic and differentiating agent in AML", *Blood*, 1999, 94(Suppl 1):479a, Abstract #2140.

Konopleva, et al., "Novel triterpenoid CDDO-Me is a potent inhibitor of apoptosis and differentiation in acute myelogenous leukemia", *Blood*, 2002, 99(1):326-335.

Konopleva, et al., "Peroxisome proliferator-activated receptor γ and retinoid X receptor ligands are potent inducers of differentiation and apoptosis in leukemias", *Mol. Cancer Ther.*, 2004, 3:1249-1262.

Konopleva, et al., "PPARγ nuclear receptor as a novel therapeutic target in AML", *Proc. of the AACR*, 2001, 42, Abstract #4458.

Konopleva, et al., "PPARγ nuclear receptor as a novel therapeutic target in AML", *Blood*, 2000, 96(11):460a, Abstract #1982.

Konopleva, et al., "PPARγ Ligand CDDO Induces Apoptosis in Leukemias Via Multiple Apoptosis Pathways", Abstracts of the 44th Annual Meeting of the American Society of Hematology, 2002, Abstract No. 2209.

Konopleva, et al., "PPARγ Ligands Are Potent Induces of Apoptosis in Leukemias and Lymphomas", American Society of Hematology 43rd Annual Meeting and Exposition, 2001, Abstract No. 501.

Konopleva, et al., "PPARγ Nuclear Receptor as a Novel Molecular Target in Leukemia Therapy", *Proc. Amer. Assoc. Cancer Res.*, 2002, 43:4730.

Konopleva, et al., "Suppression of ERK Activation is Required for Triterpenoid Methyl-CDDO-Induced Apoptosis in AML", *Blood*, 2003, 102(110:1404.

(56) References Cited

OTHER PUBLICATIONS

Konopleva, et al., "Synthetic triterpenoid 2-cyano-3,12-dioxooleana-1,9-dien-28-oic acid induces growth arrest in HER2-overexpressing breast cancer cells", *Mol. Cancer. Ther.*, 2006, 5:317-328.

Konopleva, et al., "Synthetic triterpenoid CDDO as a novel therapy for resistant breast cancer", *Proc. Amer. Assoc. Cancer Res.*, 2003, 44:2726.

Konopleva, et al., "The novel treterpenoid CDDO-Me suprresses MAPK pathways and promotes p38 activation in acute myeloid leukemia cells", *Leukemia*, 2005, 19:1350-1354.

Konopleva, et al., "The synthetic triterpenoid 2-cyano-3,12-dioxoolean-1,9-dien-28-oic acid induces caspase-dependent and -independent apoptosis in acute myelogenous leukemia", *Cancer Res.*, 2004, 64:7927-79358:2027-2057.

Konopleva, et al., "Triterpenoid methyl-CDDO is a potent inducer of apoptosis in CD34+ AML progenitor cells via activation of SAPK pathways and inhibition of MAPK cascades", *Blood*, 2004, 104:2533.

Korovin and Tkachev, "Synthesis of quinoxalines fused with triterpenes, ursolic acid and betulin derivatives", *Russian Chemical Bulletin*, (Translation of Izvestiya Akademii Nauk, Seriya Khimicheskaya), 2001, 20(2):304-310.

Koschmieder, et al., "CDDO induces granulocytic differentiation of myeloid leukemic blasts through translational up-regulation of p42 CCAAT enhanced-binding protein α", *Blood*, 110(10):3695-3705.

Kress, et al., "Triterpenoids display single agent activity in a mouse model of CLL/SBL", *Blood*, 2006, 108(11):2530.

Kress, et al., "Triterpenoids display single agent anti-tumor activity in a transgenic mouse model of chronic lymphocytic leukemia and small B cell lymphoma", *PLOS ONE*, 2007, 6(e559):1-11.

Kruger, et al., "Up-regulation of heme oxygenase provides vascular protection in an animal model of diabetes through its antioxidant and antiapoptotic effects", *J. Pharmacol. Exp. Ther.*, 2006, 319(3):1144-1152.

Kurinna, et al., "The novel triterpenoid CDDO-Me promotes apoptosis in Gleevec-resistant chronic meyloid leukemia cells by caspase-independent mechanisms", *Proc. Amer. Assoc. Cancer Res.*, 2005, 46:2240.

Kutschabsky, et al., "Natural products from Vietnamese plants. Part XV. Molecular and crystal structure of a new 24-nor triterpenoid carboxylic acid from *Acanthopanax trifoliatus*", *Croatica Chemica Acta*, 1986, 58(4):427-434.

Lapillonne, et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells", *Cancer Res.*, 2003, 63:5926-5939.

Lavie, et al., "Studies on epoxides. IV. Rearrangments in triterpenoids", *Tetrahedron Letters*, 1968, 17:2097-2100.

Lavie, et al., "Tetranortriterpenoids from *Melia azadirachta*", *Chemical Communications*, 1967, 6:278-280.

Lee, et al., "Double-stranded RNA induces iNOS gene expression in Schwann cells, sensory neuronal death, and peripheral nerve demyelination", *Glia*, 2007, 55(7):712-722.

Leonard, et al., "Expression of nitric oxide synthase in inflammatory bowel disease is not affected by corticosteroid treatment", *J. Clin. Pathol.*, 1998, 51:750-753.

Li, et al., "Terpenoids from *tripterygium wilfordii*", Phytochemistry, 1997, 45(4):791-796.

Li and Nel, "Role of Nrf2-mediated signaling pathway as a negative regulator of inflammation: implications for the impact of particulate pollutants on asthma", *Antioxidants & Redox Signaling*, 2006, 8:88-98.

Liby, et al., "A novel acetylenic tricyclic bis-(cyano enone) potently induces phase 2 cytoprotective pathways and blocks liver carcinogenesis induced by aflatoxin", *Cancer Res.*, 2008, 68:6727-6733.

Liby, et al., "Novel semisynthetic analogues of betulinic acid with diverse cytoprotective, antiproliferative, and proapoptotic activities", *Mol. Cancer Ther.*, 2007, 6(7):2113-2119.

Liby, et al., "The rexinoid LG100268 and the synthetic triterpenoid CDDO-methyl amdie are more potent than erlotinib for prevention of mouse lung carcinogenesis", *Mol. Cancer Ther.*, 2008, 7:1251-1257.

Liby, et al., "The synthetic triterpenoid CDDO-Me suppresses STAT phosphorylation and induces apoptosis in myeloma and lung cancer cells", *Clinical Cancer Research*, 2006, 12(14 Part 1):4288-4293.

Liby, et al., "The synthetic triterpenoids CDDO and CDDO-imidazole, are potent induces of heme oxygenase-1 and Nrf2/ARE signaling", *Cancer Research*, 2005, 65(11):4789-4798.

Liby, et al., "The synthetic triterpenoids CDDO-Methyl ester and CDDO-ethyl amide prevent lung cancer induced by vinyl carbamate in A/J mice", *Cancer Research*, 2007, 67(6):1-7.

Liby, et al., "Triterpenoids and rexinoids as multifunctional agents for the prevention and treatment of cancer", *Nature Review Cancer*, 2007, 7(5):357-369.

Ling, et al., "The novel triterpenoid C-28 methyl ester of 2-cyano-3,12-dioxoolen-1,9-dien-28-oic acid inhibits metastatic murine breast tumor tissue growth through inactivation of STAT3 signaling", *Cancer Research*, 2007, 67:4210-4218.

Ling, et al., "The novel triterpenoid CDDO-Me inhibits metastatic murine breast tumor through inhibition of STAT3 signaling", 2007 AACR Annual Meeting, Abstract No. 301, 2007.

Liu, et al., "Chemical constitutents from root of *Rubus irenaeus*", Zhongcaoyao, 2003, 34(5):394-396.

Liu, et al., "Heme oxygenase-1 (HO-1) inhibits postmyocardial infarct remodeling and restores ventricular function", *FASEB J*, 2006, 20(2):207-216.

Liu, et al., "New lupane-type triterpenoid saponins from leaves of *Oplopanax horridus* (Devil's Club)", *Nat. Prod. Comm.*, 2010, 5(7):1019-1022.

Lozano, et al., "Losartan reduces microalbuminuric in hypertensive microalbuminuric type 2 diabetics", *Nephrol. Dial. Transplant*, 2001, 16(Suppl 1):85-89.

Luo, et al., "IKK/NF-κB signaling: balancing life and death—a new approach to cancer therapy", *J. Clin. Invest.*, 2005, 115(10):2625-2631.

Ma, et al., "Multiorgan autoimmune inflammation, enhanced lymphoproliferation, and impaired homeostasis of reactive oxygen species in mice lacking the antioxidant-activated transcription factors Nrf2", *Am. J. Pathol*, 2006, 168:1960-1974.

Macmicking, et al., "Altered responses to bacterial infection and endotoxic shock in mice lacking inducible nitric oxide synthase", *Cell*, 1995, 81:641-650.

Maines and Gibbs, "30 some years of heme oxygenase: from a 'molecular wrecking ball' to a 'mesmerizing' trigger of cellular events", *Biochem. Biophys. Res. Commun.*, 2005, 338:568-577.

Mann, et al., "Renal outcomes with telmisartan, ramipril, or both, in people at high vascular risk (the ONTARGET study): a multicentre, randomized, double-blind, controlled trial", *Lancet*, 2008, 372:547-553.

Mantovani, et al., "Inflammation by remote control", *Nature*, 2005, 435:752-753.

Marrogi, et al., "Nitric oxide synthase, cyclooxygenase 2, and vascular endothelial growth factor in the angiogenesis of non-small cell lung carcinoma", *Clinical Cancer Research*, 2000, 6:4739-4744.

Marty, et al., "RTA 402 (CDDO-Me) increases survival of mice administered high doses of cytotoxic chemotherapy", presented by Reata Pharmaceuticals, Nov. 2005.

Mazur, et al., "Acetylsalicylic acid (ASA) blcoks influenza virus propagation via its NF-κB-inhibiting activity", *Cell Microbiol.*, 2007, 9(7):1683-1694.

Mazzoni, et al., "Myeloid suppressor lines inhibit T cell response by an NO-dependent mechanism", *J. Immunol.*, 2002, 168(2):689-695.

Melichar, et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression", *Gynecologic Oncology*, 2004, 93:149-154.

Mencherini, et al., "Triterpenoid constituents from the roots of the *Paeonia rockii* ssp. Rockii", *J. Nat. Prod.*, 2011, 74(10):2116-2121.

(56) References Cited

OTHER PUBLICATIONS

Minns, et al., "A novel triterpenoid induces transforming growth factor beta production by intraepithelial lymphocytes to prevent ileitis", *Gastroenterology*, 2004, 127:119-126.

Mix, et al., "A synthetic triterpenoid selectively inhibits the induction of matrix metalloproteinases 1 and 13 by inflammatory cytokines", *Arthritis Rheum.*, 2001, 44:1096-1104.

Mix, et al., "Peroxisome proliferator-activated receptor-gamma-independent repression of collagenase gene expression by 2-cyano-3,12-dioxooleana-1,9-dien-28-oic acid and prostaglandin 15-deoxy-Δ(12,14) J2: a role in Smad signaling", *Mol. Pharmacol.*, 2004, 65(2):309-318.

Moncada, et al., "Nitric Oxide: physiology, pathophysiology, and pharmacology", *Pharmacol. Rev.*, 1991, 43:109-142.

Morris, et al., "Association of a functional inducible nitric oxide synthase promoter variant with complications in type 2 diabetes", *J. Mol. Med.*, 80(2):96-104, 2002, 80(2):96-104.

Morse and Choi, "Heme oxygenase-1: from bench to bedside", *Am. J. Respir. Crit. Care. Med.*, 2005, 172(6):660-670.

Morse and Choi, "Heine oxygenase-1: the 'emerging molecule' has arrived", *Am. J. Respir. Crit. Care Med.*, 2002, 27(1):8-16.

Murphy, et al., "Immunomodulatory Effects of the Triterpenoid CDDO after Allogeneic Bone Marrow Transplantation in Mice: Reduction of Acute Graft-Versus-Host Disease Lethality", *Blood*, 2005, 106:1316.

Na and Surh, et al., "Transcriptional regulation via cysteine thiol modification: a novel molecular strategy for chemoprevention and cytoprotection", *Mol. Carcinog.*, 2006, 45(6):368-380.

Naik, et al., "Role of oxidative stress in pathophysiology of peripheral neuropathy and modulation by N-acetyl-L-cysteine in rats", *Eur. J. Pain*, 2006, 10(7):573-579.

Nair, et al., "Triterpenes. XLVII. Oxidation rates of triterpenoid secondary alcohols with chromic acid", *Collection of Czechoslovak Chemical Communications*, 1976, 41(3):770-779.

Nanduri, et al., "Biological investigation and structure-activity relationship studies on azadirone from *Azadirachta indica* A. juss", *Bioorganic and Medicinal Chemistry*, 2003, 13(22):4111-4115.

Nath, "Heme oxygenase-1: a provenance for cytoprotective pathways in the kidney and other tissues", *Kidney Int.*, 2006, 70:432-443.

Nathan, "Point of control in inflammation", *Nature*, 2002, 420:846-852.

Nathan and Xie, "Nitric oxide synthases: roles, tolls, and controls", *Cell*, 1994, 78:915-918.

Nelson, et al., "Oxidative demethylation at C-4 of a steroid via nitroxide photolysis", *J. of the American Chemical Society*, 1975, 97(3):648-649.

Nguyen, et al., "The Nrf2-antioxidant response element signaling pathway and its activation by oxidative stress", *J. Biol. Chem.*, 2009, 284(20):13291-5.

Nichols, "NF-κB and reperfusion injury", *Drug News Perpect.*, 2004, 17(2):99-104.

Niikura, et al., "The effects of synthetic triterpenoids on superficial zone protein synthesis in articular chondrocytes", Abstract, Orthopedic Research Society, San Diego, 2007.

Niikura, et al., "The effects of synthetic triterpenoids on szp synthesis in articular chondrocytes", Abstract P197, Osteoarthritis and Cartilage, 2006, 14(Suppl B):S112-S113.

Nishimura, et al., "Activity-guided isolation of triterpenoid acyl CoA cholesteryl acyl transferase (ACAT) inhibitors from *Ilex kudincha*", *J. Nat. Prod.*, 1999, 62(7):1061-1064.

Nishino, et al., "Inhibition of the tumor-promoting action of 12-O tetradecanoylphorbol-13-acetate by some oleanane-type triterpenoid compounds", *Cancer Res.*, 1988, 48:5210-5215.

Notice of Allowance, in U.S. Appl. No. 12/352,473, issued Mar. 6, 2012.

Notice of Allowance, in U.S. Appl. No. 13/359,381, issued Jun. 4, 2012.

Osburn, et al., "Genetic of pharmacologic amplification of Nrf2 signaling inhibits acute inflammatory liver injury in mice", *Toxicology Sciences*, 2008, 104:218-227.

Oshima, et al., "Suppression of intestinal polyposis in ApcD716 knockout mice by inhibition of cyclooxygenase 2 (COX-2)", *Cell*, 1996, 87:803-809.

Pahl, "Activators and target genes of Rel/NF-κB transcription factors", *Oncogene*, 1999, 18:6853-6866.

Pall, "Nitric oxide synthase partial uncoupling as a key switching mechanism for the NO/ONOO-cycle", *Med. Hypoth.*, 2007, 69(4):821-825.

PCT Application WO 2009/089545, International Preliminary Report on Patentability, issued Jul. 13, 2010.

Peakman, et al., "Characterization of 24-nor-triterpenoids occurring in sediments and crude oils by comparison with synthesized standards", *Tetrahedron*, 1991, 47(23):3779-3786.

Pedersen, et al., "The triterpenoid CDDO induces apoptosis in refractory CLL B cells", *Blood*, 2002, 100:2965-2972.

Pergola, et al., "Bardoxolone Methyl and Kidney Function in CKD with Type 2 diabetes", *New England Journal of Medicine*, 2011, 365:327-336.

Place, et al., "The novel synthetic triterpenoid, CDDO-imidazolide, inhibits inflammatory response and tumor growth in vivo", *Clin. Cancer Res.*, 2003, 9:2798-2806.

Rajakariar, et al., "Hematopoietic prostaglandin D2 synthase controls the onset and resolution of acute inflammation through PGD2 and 15-deoxyΔ12,14PGJ2", *Proc. Natl. Acad. Sci. USA*, 2007, 104(52):20979-20984.

Rangasamy, et al., "Disruption of Nrf2 enhances susceptibility to severe airway inflammation and asthma in mice", *Journal of Experimental Medicine*, 2005, 202:47-59.

Rasmusson, et al., "Azasteroids: structure-activity relationships for inhibition of 5 alpha-reductase and of androgen receptor binding", *J. Med. Chem.*, 1986, 29(11):2298.

Ray, Denise M. et al., "The novel triterpenoid 2-cyano-3,12-dioxooleana-1,9-dien-28-oic acid (CDDO) Induces Apoptosis of Human Diffuse Large B-cell Lymphoma Cells through a Peroxisome Proliferator-activated Receptor gamma-independent Pathway", *Experimental Hematology*, 2006, 34:1201-1210.

Rayet and Gelina, "Aberrant rel/nfκb genes and activity in human cancer", *Oncogene*, 1999, 18:6938-6947.

Ribo, et al., "Synthesis of methyl 1,11-dioxooleanan-2,12-dien-30-oate and its 24-nor derivative", *Afinidad*, 1981, 38(373):197-200.

Rodriguez-Spong, et al., "General principles of pharmaceutical solid polymorphism: a supramolecular perspective", *Advanced Drug Delivery Reviews*, 2004, 56:241-274.

Ross, et al., "Breast cancer biomarkers and molecular medicine", *Expert Rev. Mol. Diagn.*, 2003, 3(5):573-585.

Ross, et al., "HER-2/neu testing in breast cancer", *Am. J. Clin. Pathol.*, 2003, 120(Suppl):S53-71.

Rossi, et al., "Anti-inflammatory cyclopentenone prostaglandins are direct inhibitors of IκB kinase", *Nature*, 2000, 403:103-108.

Rouquette, et al., "A ring-D functionalized nor-triterpenoid of the lupane series as a key intermediate in the formation of widespread hydrocarbon derivatives of higher plant origin in petroleum", *Organic Geochemistry*, 2005, 36(9):1227-1233.

Ruster, et al., "Detection of elevated N epsilon-carboxymethyllysine levels in muscular tissue and in serum of patients with fibromyalgia", *Scand. J. Rheumatol.*, 2005, 34(6):460-463.

Ruvolo, et al., "The novel triterpenoid methyl-CDDO inhibits Bc12 phosphorylation and potently kills U937 cells", *Blood*, 1999, 94(10), Suppl. 1, Part 1: 280A, abstract #1251.

Sacerdoti, et al., "Heme oxygenase overexpression attenuates glucose-mediated oxidative stress in quiescent cell phase: linking heme to hyperglycemia complications", *Curr. Neurovasc. Res.*, 2005, 2(2):103-111.

Saha, et al., "The triterpenoid 2-cyano-3,12-dioxooleana-1,9-dien-28-oic acid methyl ester has potent anti-diabetic effects in diet-induced diabetic mice and Lepr$^{db/db}$ mice", *J. Biol. Chem.*, 2010, 285:40581-92.

Salvemini, et al., "Endogenous ntiric oxide enhances prostaglandin production in a modelof renal inflammation", *J. Clin. Invest.*, 1994, 93(5):1940-1947.

(56) References Cited

OTHER PUBLICATIONS

Salvemini, et al., "Nitric oxide activates cyclooxygenase enzymes", *Proc. Natl. Acad. Sci. USA*, 1993, 90(15):7240-7244.
Samudio, et al., "2-cyano-3,12-dioxoolean-1,9-diene-28-imidazolide induces apoptosis in pancreatic cancer via redox-dependent cytoplasmic stress", *Proc. Amer. Assoc. Cancer Res.*, 2005, 46:Abstract No. 5899.
Samudio, et al., "2-cyano-3,12-dioxooleana-1,9-dien-28-imidazolide (CDDO-Im) directly targets mitochondrial glutathione to induce apoptosis in pancreatic cancer", *J. Biol. Chem.*, 2005, 280:36273-36282.
Samudio, et al., "A novel mechanism of action of methyl-2-cyano-3,12-dioxoolean-1,9-diene-28-oate (CDDO-Me): Direct permeabilization of the inner mitochondrial membrane to inhibit electron transport and induce apoptosis", *Proc. Am. Assoc. Cancer Res.*, 2006, 47:Abstract #4693.
Samudio, et al., "A novel mechanism of action of methyl-2-cyano-3,12-dioxoolean-1,9-diene-28-oate: direct permeabilization of the inner mitochondrial membrane to inhibit electron transport and induce apoptosis", *Mol. Pharmacol.*, 2006, 69:1182-1193.
Samudio, et al., "The novel triterpenoid CDDOme potently synergizes with inhibition of bcl-2 function to induce apoptosis in AML via disruption of intracellular redox homeostasis", *Proc. Amer. Assoc. Cancer Res.*, 2005, 46:Abstract No. 4955.
Sarchielli, et al., "NF-κB activity and iNOS expression in monocytes from internal jugular blood of migraine without aura patients during attacks", *Cephalalgia*, 2006, 26(9):1071-1079.
Satoh, et al., "Activation of the Keap1/Nrf2 pathway for neuroprotection by electrophilic phase II inducers", *PNAS*, 2006, 103(3):768-773.
Scholtz, et al., "Sensitive and specific methods for the determination of CDDO methyl ester in mouse, rat, dog, monkey, and human plasma by LC-tandem mass spectrometry", *Proc. Amer. Assoc. Cancer Res.*, 2003, 4:Abstract No. 6321.
Schultz, et al., "Nitric oxide, tetrahydrobiopterin, oxidative stress, and endothelial dysfunciton in hypertension", *Antioxid. Redox. Sig.*, 2008, 10(6):1115-1126.
Seibert and Masferrer, "Role of inducible cyclooxygenase (COX-2) in inflammation," *Receptor*, 4(1):17-23, 1994.
Sengul, et al., "Beneficial effect of lisinopril plus telmisartan in patients with type 2 diabetes, microaluminuria and hypertension", *Diabetes Research and Clinical Practice*, 2006, 71:210-219.
Serhan, et al., "Resolving inflammation: dual anti-inflammatory and pro-resolution lipid mediators", *Nat. Rev.*, 2008, 8:349-361.
Shin, "Inhibitory roles of Nrf2 and an oleanolic triterpenoid on adipocyte differentiation and obesity", dissertation submitted to John Hopkins University in conformity with the requirements for the degree of Doctor of Philosophy, Mar. 2009.
Shin, et al., "Nrf2 modulates aryl hydrocarbon receptor signaling: influence on adipogenesis", *Molecular and Cellular Biology*, 2007, 27(20):7188-7197.
Shin, et al., "Role of Nrf2 in prevention of high-fat diet-induced obesity by synthetic triterpenoid CDDO-imidazolium", *Eur. J. Pharmacol.*, 2009, 620(1-3):138-144.
Shishodia, et al., "A synthetic triterpenoid, CDDO-Me, inhibits IκBα kinase and enhances apoptosis induced by TNF and chemotherapuetic agents through down-regulation of expression of nuclear factor κB-regulated gene products in human leukemic cells", *Clinical Cancer Research*, 2006, 12(6):1828-1838.
Siddiqui, et al., "Kanerin and 12,13-dihydroursolic acid, two new pentacyclic triterpenes from the leaves of Nerium oleander", *J. Nat. Prod.*, 1989, 52(1):57-62.
Simonian and Coyle, "Oxidative stress in neurodegenerative diseases", *Annu. Rev. Pharmacol. Toxicol.*, 1996, 36:83-106.
Simonsen, et al., "Tetracyclic hydroxy acids", In the Terpenes, Cambridge University, Cambridge, 1957, 5:221-285.
Singh, et al., "Anti-inflammatory activity of oleanolic acid in rats and mice", *J. Pharm. Pharmacol.*, 1992, 44:456-458.
Singh and Evans, "Nitric Oxide, the biological mediator of the decade: fact or fiction," *Eur. Respir. J.*, 1997, 10:699-707.
Sjoholm and Nystrom, "Inflammation and the etiology of type 2 diabetes", *Diabetes Metab. Res. Rev.*, 2006, 22:4-10.
Slides by Reata Pharmaceuticals, "RTA 402, Therapeutic Properties III", podium presentation at BIO 2006 conference, Apr. 9-12, 2006, Chicago, Illinois.
Slides/Handout by Reata Pharma., "RTA 402, Therapeutic Properties I", Private partnering meetings at BioSquare 2006 conference, Mar. 8-10, 2006, Geneva, Switzerland.
Slides/Handout by Reata Pharma., "RTA 402, Therapeutic Properties II", Private partnering meetings at BIO 2006 conference, Apr. 9-12, 2006, Chicago, Illinois.
Slides/Handout by Reata Pharma., "RTA 402, Therapeutic Properties IV", Private partnering meetings at BioPartnering Europe 2006 conference, Oct. 8-10, 2006, London, England.
Slides/Handout by Reata Pharma., "RTA 402, Therapeutic Properties IX", Private partnering meeting at BIO Europe 2007 conference, Nov. 12-14, 2007, Hamburg, Germany.
Slides/Handout by Reata Pharma., "RTA 402, Therapeutic Properties V", Private partnering meetings at BIO 2007 conference, May 6-9, 2007, Boston, Massachusetts.
Slides/Handout by Reata Pharma., "RTA 402, Therapeutic Properties VI", Private partnering meetings at BIO 2007 conference, May 6-9, 2007, Boston, Massachusetts.
Slides/Handout by Reata Pharma., "RTA 402, Therapeutic Properties VII", Podium presentation at BIO 2007 conference, May 6-9, 2007, Boston, Massachusetts.
Slides/Handout by Reata Pharma., "RTA 402, Therapeutic Properties VIII", Private partnering meetings at BIO Europe 2007 conference, Nov. 12-14, 2007, Hamburg, Germany.
Sporn, et al., "Prospects for prevention and treatment of cancer with selective PPARγ modulators (SPARMs)", *Trends in Molecular Medicine*, 2001, 7(9):395-400.
Sporn, et al., "Transforming growth factor-beta: biological function and chemical structure", *Science*, 1986, 233:532-534.
Sporn and Roberts, "Peptide growth factors and inflammation, tissue repair, and cancer", *J. Clin. Invest.*, 1986, 78:329-332.
Stacul, et al., "Strategies to reduce the risk of contrast-induced nephropathy", *Am. J. Cardiol.*, 2006, 98(suppl):59K-77K.
Stadheim, et al., "The novel triterpenoid 2-cyano-3,12-dioxooleana-1,9-dien-28-oic acid (CDDO) potently enhances apoptosis induced by tumor necrosis factor in human leukemia cells", *J. Biol. Chem*, 2002, 277:16448-16455.
Suh, et al., "A novel synthetic oleanane triterpenoid, 2-cyano-3,12-dioxoolean-1,9-dien-28-oic acid (CDDO), induces cell differentiation in human myeloid leukemias", Proceedings of the American Association for Cancer Research Annual Meeting, 40:300 abstract.
Suh, et al., "A novel synthetic oleanane triterpenoid, 2-cyano-3,12-dioxoolean-1,9-dien-28-oic acid, with potent differentiating, antiproliferative, and anti-inflammatory activity", *Cancer Res.*, 1999, 59(2):336-341.
Suh, et al., "New triterpenoids as cancer preventive and anti-inflammatory agents", Proceedings of the American Association for Cancer Research, 1997, Abstract No. 1457, 38:216.
Suh, et al., "Novel triterpenoids suppress inducible nitric oxide synthase (iNOS) and inducible cyclooxygenase (COX-2)", Proceedings of the American Association for Cancer Research Annual Meeting, 1998, 39:Abstract No. 1821.
Suh, et al., "Novel triterpenoids suppress inducible nitric oxide synthase (iNOS) and inducible cyclooxygenase (COX-2) in mouse macrophages", *Cancer Res.*, 1998, 58:717-723.
Suh, et al., "Synthetic triterpenoids activate a pathway for apoptosis in AML cells involving downregulation of FLIP and sensitization to TRAIL", *Leukemia*, 2003, 17:2122-2129.
Suh, et al., "Synthetic triterpenoids enhance transforming growth factor β/Smad signaling", *Cancer Res.*, 2003, 63:1371-1376.
Suh, et al., "Triterpenoids CDDO and CDDO-Me Down-Regulate FLIP Expression and Sensitize AML cells to Trail-Induced Apoptosis", American Society of Hematology 43rd Annual Meeting and Exposition, 2001, Abstract No. 498.
Sultana, et al., "Phytochemical studies on *Alstonia scholaris*", *Zeitschrift für Naturforschung B, A Journal of Chemical Sciences*, 2010, 65(2):203-210.

(56) References Cited

OTHER PUBLICATIONS

Sun, et al., "Structure-activity relationships of olean- and ursane-type triterpenoids", *Botanical Studies*, 2006, 47:339-368.
Sun, et al., "The synthetic triterpenoid, CDDO, suppresses alloreactive T cell responses and reduces murine early acute graft-versus-host disease mortality", *Biology of Blood and Marrow Transplantation*, 2007, 13(5):521-529.
Sussan, et al., "Disruption of Nrf2, a key inducer of antioxidant defenses, attenuates ApoE-mediated atherosclerosis in mice", *PLoS One*, 2008, 3(11):1-9.
Tabe, et al., "Chromatin-Mediated Transcriptional Activation with Novel Peroxisome Proliferator-Activated Receptor γ (PPARγ) Ligand 2-cyano-1,9-dien-28-oic acid (CDDO) in Acute Promyelocytic leukemia cells", Abstracts of the 44th Annual Meeting of the American Society of Hematology.
Takahashi, et al., "Increased expression of inducible and endothelial constitutive nitric oxide synthases in rat colon tumors induced by azoxymethane", *Cancer Res.*, 1997, 57:1233-1237.
Takahashi, et al., "Organ protective role of heme oxygenase-1 against oxidative stress", *Folia Pharmacolgica Japonica*, 2007, 130:252-256.
Takahashi, et al., "Role of stress protein in organopathy", *Renal and Intestinal Injury*, (English Translation), 2006, 30:359-365.
Takaishi, et al., "Triterpenoid inhibitors of interleukin-1 secretion and tumor-promotion from *Tripterygium wilfordii* var. regelii", *Phytochemistry*, 1997, 45(5):969-974.
Tamir and Tannebaum, "The role of nitric oxide (NO) in the carcinogenic process", *Biochim. Biophys. Acta*, 1996, 1288:F31-F36.
Tanaka, et al., "A new triterpenoid from the leaves of *Eucommia ulmoides* Oliv.", *Chem. Pharm. Bull* (Tokyo), 1997, 45(8):1379-1380.
Ten Haven, et al., "Early diagenetic transformation of higher-plant triterpenoids in deep-sea sediments from Baffin Bay", *Geochimicha et Cosmochimica Acta*, 1992, 56(5):2001-2024.
Thaler, "Hypothalamic inflammation and energy homeostatsis: resolving the paradox", *Front. Neuroendocrinol.*, 2010, 31(1):79-84.
Thimmulappa, et al., "Identification of Nrf2-regulated genes induced by the chemopreventive agent sulforaphane by oligonucleotide microarray", *Cancer Research*, 2002, 62:5196-5203.
Thimmulappa, et al., "Nrf2 is a critical regulator of the innate immune response and survival during experimental sepsis",*J. Clinical Investigations*, 2006, 116(4):984-995.
Thimmulappa, et al., "Nrf2-dependent protection from LPS induced inflammatory response and mortality by CDDO-imidazole", *Biochem. Biophys. Res. Commun.*, 2006, 351:883-889.
Thimmulappa, et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils", *Antioxidants & Redox Signaling*, 2007, 9(11):1-8.
Torres, et al., "Inflammation and nitric oxide production in skeletal muscle of type 2 diabetic patients", *Journal of Endocrinology*, 2004, 181:419-427.
Tran, et al., "The synthetic triterpenoid CDDO-methyl ester modulates microglial activities, inhibits THF production, and provides dopaminergic neuroprotection", *Journal of Neuroinflammation*, 2008, 5:1-14.
Tsao, et al., "DRIP205 co-activator overexpression enhances PPARγ-mediated differentiation of leukemia cells by CDDO", *Proc. Amer. Assoc. Cancer res.*, 2005, 46:Abstract No. 1855.
Tsao, et al., "Targeted Induction of Apoptosis in Leukemias by PPARγ Ligation", American Society of Hematology 43rd Annual Meeting and Exposition, 2001, Abstract No. 2381.
Tumlin, et al., "Pathophysiology of contrast-induced nephropathy", *Am. J. Cardiol.*, 2006, 98(6A):14K-20K.
Urban, et al., "Influence of esterification and modification of A-ring in a group of lupane acids on their cytotoxicity", *Bioorganic and Medicinal Chemistry*, 2005, 13(19):5527-5535.

Urban, et al., "Synthesis of A-seco derivatives of betulinic acid with cytotoxic activity", *J. of Natural Products*, 2004, 67(7):1100-1105.
Uskoković, et al., "D-Homosteroids. I. 3β-hydroxy-17a,17a-dimethyl-D-homoandrostane-17-one and related compounds", *J. of the American Chemical Society*, 1959, 81:4561-4566.
Van Kiem, et al., "A new 24-nor-lupane-gylcoside of *Acanthopanax trifoliatus*", *Arch. Pharm. Res.*, 2003, 26(9):706-708.
Van Muiscwinkel and Kiuperij, "The Nrf2-ARE signaling pathway: promising drug target to combat oxidative stress in neurodegenerative disorders", *Current Drug Trends—CNS & Neurological Disorders*, 2005, 4:267-281.
Vannini, et al., "The synthetic oleanane triterpenoid, CDDO-methyl ester, is a potent antiangiogenic agent", *Molecular Cancer Therapeutics*, 2007, 6(12 Part 1):3139-3146.
Vazquez, et al., "Human immunodeficiency virus type 1-induced macrophage gene expression includes the p21 gene, a target for viral regulation", *J. Virol.*, 2005, 70:4479-4491.
Viberti, et al., "Microalbuminuria reduction with valsartan in patients with type 2 diabetes mellitus—A blood pressure-independent effect", *Circulation*, 2002, 106:676-678.
Vilayur and Harris, "Emerging therapies for chronic kidney disease: what is their role?", *Nature Reviews*, 2009, 5:375-383.
Vincenti, et al., "The synthetic triterpenoid TP-222 inhibits RANKL induction of differentiation and MMP-9 gene expression in osteoclasts", Abstract 1385, American College of Rheumatology Annual Scientific Meeting, 2006.
Wada and Tanaka, "Synthetic lanostane-type triterpenoids as inhibitors of DNA topoisomerase II", *Bioorganic and Medicinal Chemistry Letters*, 2005, 15(12):2966-2969.
Wang, et al., "A novel synthetic triterpenoid, 2-cyano-3,12-dioxoolean-1,9-dien-28-oic acid (CDDO) induces adipocyte differentiation in 3T3-L1 cells", Proceedings of the American Association for Cancer Research Annual Meeting, 1999, 40:300 abstract No. 1989.
Wang, et al., "A synthetic triterpenoid, 2-cyano-3,12-dioxooleana-1,9-dien-28-oic acid (CDDO), is a ligand for the peroxisome proliferator-activated receptor γ", *Mol. Endocrin.*, 2000, 14(10):1550-1556.
Wang, et al., "Synthetic triterpenoid CDDO and its derivatives increase ceramides and are cytotoxic to pediatric acute lymphoblastic leukemia cell lines", *Proc. Am. Assoc. Cancer Res.*, 2006, 47:4643.
Waratchareeyakul, et al., "2,19-dihydroxy-3-oxo-(2,4,19)-24-nor-olean-12-en-28-oic acid monohydrate", *Acta. Cryst.*, 2007, E63, o4062-o4063.
Wardle, et al., "Nuclear factor κB for the nephrologist", *Nephrol. Dial. Transplant.*, 2001, 16(9):1764-68.
Wen, et al., "Pentacyclic triterpenes. Part 2: Synthesis and Biological evaluation of maslinic acid derivatives as glycogen phosphorylase inhibitors", *Bioorganic and Medicinal Chemistry Letters*, 2006, 16(3):722-726.
White, et al., "A novel demethylated oxygenated triterpenoid in crude oils from the Canadian Beaufort sea and northeast Alaska", *Tetrahedron Letters*, 1998, 39(19):3031-3034.
Wu, et al., "Beneficial role of Nrf2 in regulating NADPH generation and consumption", *Toxicological Sciences*, 2011, 123(2):590-600.
Xie, et al., "ARE- and TRE-mediated regulation of gene expression response to xenobiotics and antioxidants", *J. Biol. Chem.*, 1995, 270(12):6894-6900.
Yao, et al., "Ciplatin nephrotoxicity: a review", *Am. J. Med. Sci.*, 2007, 334(2):115-124.
Yates, et al., "Pharmacodynamic characterization of chemopreventive triterpenoids as exceptionally potent inducers of Nrf2-regulated genes", *Mol. Cancer Ther.*, 2007, 6:154-162.
Yates, et al., "Potent protection against aflatoxin-induced tumorigenesis through induction of Nrf2-regulated pathways by the triterpenoid 1-[2-cyano-3,12-dioxooleana-1,9(11)-dien-28-oyl]imidazole", *Cancer Res.*, 2007, 66(4):2488-2494.
Yoh, et al., "Nrf2-deficient female mice develop lupus-like autoimmune nephritis", *Kidney Int.*, 2001, 60(4):1343-1353.
Yore, et al., "The synthetic triterpenoid 1-[2-cyano-3,12-dioxooleana-1,9(11)-dien-28-oyl]imidazole blocks nuclear factor-

(56) References Cited

OTHER PUBLICATIONS

κB activation through direct inhibition of IκB kinase beta", *Mol. Cancer Ther.*, 2006, 5(12):3232-3239.
You, et al., "Synthesis and cytotoxic activity of a-ring modified betulinic acid derivatives", *Bioorganic and Medicinal Chemistry Letters*, 2003, 13(19):3137-3140.
Yu and Kensler, "Nrf2 as a target for cancer chemoprevention", *Mutat. Res.*, 2005, 591(1-2):93-102.
Yue, et al., "Depletion of intracellular glutathione contributes to JNK-mediated death receptor 5 upregulation and apoptosis induction by the novel synthetic tnterpenoid methyl-2-cyano-3,12-dioxooleana-1,9-dien-28-oate (CDDO-Me)", *Cancer & Biology Therapy*, 2006, 5(5):492-497.
Zapata, et al., "CDDO and CDDO-Im reduce tumor burden in a transgenic mouse model of CLL", *Blood*, 2004, 104:3477.
Zapata, et al., "Triterpenoids show activity against leukemic cells in a transgenic mouse model of CLL", *Proc. Amer. Assoc. Cancer Res.*, 2005, 46:Abstract No. 5179.
Zhang, et al., "Hypthalamic IKKβ/NF-κB and ER stress link overnutrition to energy imbalance and obesity", *Cell*, 2008, 135(1):61-73.
Zhang, et al., "Synthetic triterpenoid CDDO as effective therapy for HER2-expressing resistant breast cancer", *Proc. Amer. Assoc. Cancer Res.*, 2004, Abstract No. 3799.
Zhang, et al., "The novel synthetic oleanane triterpenoid CDDO (2-cyano-3,12-dioxoolean-1,9-dien-28-oic acid) induces apoptosis in Mycosis fungoides/Sézary syndrome cells", *J. Invest. Dermatol.*, 2004, 123:380-387.
Zhou, et al., "A new triterpenoid from the roots of *Tripterygium wildfordii*", *Chinese Chemical Letters*, 2010, 21(5):600-602.
Zhou, et al., "Physical stability of amorphous pharmaceuticals: Importance of configurational thermodynamic quantities and molecule mobility", *J. Pharmaceutical Sciences*, 2002, 91(8):1863-1872.
Zingarelli, et al., "Nuclear factor-κB as a therapeutic target in critical care medicine", *Crit. Care Med.*, 2003, 31(Suppl):S105-S111.
Zou, et al., "c-Jun NH2-terminal kinase-mediated up-regulation of death receptor 5 contributes to induction of apoptois by the novel synthetic triterpenoid methyl-2-cyano-3,12-dioxooleana-1,9-dien-28-oate in human lung cancer cells", *Cancer Res.*, 2004, 64:7570.
Zou, et al., "PPARγ ligands enhance TRAIL-induced apoptosis through DR5 upregulation and c-FLIP downregulation in human lung cancer cells", *Cancer Biology and Therapy*, 2007, 6(1):99-106.
Heiss, et al., "Active NF-E2-related factor (Nrf2) contributes to keep endothelial NO synthase (eNOS) in the coupled state: role of reactive oxygen species (ROS), eNOS, and heme oxygenase (HO-1) levels", *J. Biol. Chem.*, 2009, 284:31579-31586.
Hybertson, et al., "Oxidative stress in health and disease: The therapeutic potential of Nrf2 activation", *Molecular Aspects of Medicine*, 2011, 32:234-246.
Sussan, et al., "Targeting Nrf2 with the triterpenoid CDDO-imidazolide attenuate cigarette smoke-induced emphysema and cardiac dysfunction in mice", *Proc. Nat. Sci. Acad. USA*, 2009, 106:250-255.
Xing, et al., "Triterpenoid dihydro-CDDO-trifluoroethyl amide protects against maladaptive cardiac remodeling and dysfunction in mice: a critical role of Nrf2", *PLoS One*, 2012, 7:344899.
Notice of Opposition issued in Colombian Patent Application No. 10.098.518, dated Mar. 14, 2012 (English Summary).
International Search Report and Written Opinion issued in PCT/US2009/030771, dated Apr. 9, 2009.
Kornblau, et al., "Phase I study of mitoxantrone plus etoposide with multidrug blockade by SDZ PSC-833 in relapsed or refractory acute myelogenous leukemia," *J. Clinical Oncology*, 1997, 15(5):1796-1802.
Tsujii and DuBois, "Alterations in cellular adhesion and apoptosis in epithelial cells overexpressing prostaglandin endoperoxide synthase 2," *Cell*, 1995, 83:493-501.

Tsujii, et al., "Cyclooxygenase regulates angiogenesis induced by colon cancer cells," *Cell*, 1998, 93:705-716.
Office Action and Search Report in Co-pending Taiwanese Application 102108736, dated Jul. 29, 2014.
Deeb, et al., "CDDO-Me Induces Apoptosis and Inhibits Akt, mTOR and NF-κB Signaling Proteins in Prostate Cancer Cells," *Anticancer Research*, 27:3035-3044, 2007.
Office Action and Search Report in Co-pending Taiwanese Application 098113098, dated Aug. 19, 2013. (Chinese, English translation of Search Report).
Chartoumpekis and Sykiotis, "Bardoxolone Methyl in Type 2 Diabetes and Advanced Chronic Kidney Disease, Letter to the Editor," *New Eng. J. Med.*, 370(18):1767, 2014.
Chertow and de Zeeuw, "Bardoxolone Methyl in Type 2 Diabetes and Advanced Chronic Kidney Disease, Letter to the Editor," *New Eng. J. Med.*, 370(18):1768, 2014.
Chin, et al., "Bardoxolone methyl analogs RTA 405 and dh404 are well tolerated and exhibit efficacy in rodent models of Type 2 diabetes and obesity," *Am. J. Physiology*, 304(6):F1438-F1446, 2013.
Ellison, "Bardoxolone Methyl in Type 2 Diabetes and Advanced Chronic Kidney Disease, Letter to the Editor," *New Eng. J. Med.*, 370(18):1768, 2014.
Harris, "The Best-Laid Plans," *Am. J. Physiology*, 304(4):F1086-F1087, 2013.
Heiss, et al., "Impact of the Synthetic Triterpenoid CDDO-Im and Nrf2 Activation on the Endothelial Redox System," Poster Presentation at 2008 Nordic Pharmacological Society, Abstract in *Basic and Clinical Pharmacology & Toxicology*, 102(Supp 1):21-57, 2008.
Himmelfarb and Tuttle, "Bardoxolone Methyl in Type 2 Diabetes and Advanced Chronic Kidney Disease, Letter to the Editor," *New Eng. J. Med.*, 370(18):1768-1769, 2014.
Hong, et al., "Phase I Trial with a Novel Orally Administered Synthetic Triterpenoid RTA 402 (CDDO-Me) in Patients with Solid Tumors and Lymphoid Malignancies," Poster Presentation at AACR-NCI-EORTC Molecular Targets and Cancer Therapeutics Conference in San Diego, Oct. 24, 2007.
Kidd, et al., "Mesenchymal stromal cells alone or expressing interferon-β suppress pancreatic tumors in vivo, an effect countered by anti-inflammatory treatment," *Cytotherapy*, 12(5):615-625, 2010.
Laight, et al., "Antioxidants, diabetes, and endothelial dysfunction," *Cardiovascular Research*, 47:457-464, 2000.
McMahon and Forman, "Bardoxolone Methyl, Chronic Kidney Disease, and Type 2 Diabetes: Letter to the Editor," *New Eng. J. Med.*, 365(18):1746, 2011.
McQuaid and Keenan, "Physiological Society Symposium: Impaired Endothelial and Smooth Muscle Cell Function in Oxidative Stress: Endothelial Barrier Dysfunction and Oxidative Stress: Roles for Nitric Oxide?" *Experimental Physiology*, 82:369-376, 1997.
Molnár, et al., "Bardoxolone Methyl in Type 2 Diabetes and Advanced Chronic Kidney Disease, Letter to the Editor," *New Eng. J. Med.*, 370(18):1767-1768, 2014.
Morris and Jardine, "The Vascular Endothelium in Chronic Kidney Failure," *J. Nephrol.*, 3(2):96-105, 2000.
Pergola, et al., "Bardoxolone Methyl, Chronic Kidney Disease, and Type 2 Diabetes: Reply to Letters to the Editor," *New Eng. J. Med.*, 365(18):1746-1747, 2011.
Petronelli, et al., "CDDO-Im is a stimulator of megakaryocytic differentiation," *Leukemia Research*, 35(4):534-544, 2011.
Ochodnicky, et al., "Endothelial dysfunction in chronic kidney disease: determinant of susceptibility to end-organ damage and therapeutic response," *J. Nephrol.*, 19(3):246-258, 2006.
Rogacev, et al., "Bardoxolone Methyl, Chronic Kidney Disease, and Type 2 Diabetes: Letter to the Editor," *New Eng. J. Med.*, 365(18):1745-1746, 2011.
Ruilope, et al., "Cardiovascular Risk Reduction by Reversing Endothelial Dysfunction: ARBs, ACE inhibitors, or both? Expectations from The ONTARGET Trial Programme," *Vascular Health and Risk Management*, 3(1):1-9, 2007.

(56) References Cited

OTHER PUBLICATIONS

Van Laecke and Vanholder, "Bardoxolone Methyl, Chronic Kidney Disease, and Type 2 Diabetes: Letter to the Editor," *New Eng. J. Med.*, 365(18):1745, 2011.

Upadhyay, et al., "Bardoxolone Methyl, Chronic Kidney Disease, and Type 2 Diabetes: Letter to the Editor," *New Eng. J. Med.*, 365(18):1746, 2011.

Zhang, et al., "Kidney disease and the metabolic syndrome," *Am. J. Med. Sci.*, 330(6):319-325, 2005.

Zoja, et al., "Analogs of Bardoxolone Methyl Worsen Diabetic Nephropathy in Rats with Additional Adverse Effects," *Am. J. Physiology*, 304(3):F808-F819, 2013.

Mednis et al., Editors, *Global Atlas on Cardiovascular Disease Prevention and Control*, World Health Organization, Geneva, 2011.

Watnick and Morrison, "Kidney Disease," In: Current Medical Diagnosis & Treatment, edited by Stephen J. McPhee and Maxine A. Papadakis, McGraw Hill Medical, Chapter 22, pp. 785-815, 2008.

Office Action in Counterpart Israeli Patent Application No. 243537 issued on Jan. 29, 2017.

Beyer, et al., "Impaired liver regeneration in Nrf2 knockout mice: role of ROS-mediated insulin/IGF-1 resistance," *The EMBO Journal*, 27:212-223, 2008.

\* cited by examiner

SYNTHETIC TRITERPENOIDS AND METHODS OF USE IN THE TREATMENT OF DISEASE

This application is a continuation of U.S. patent application Ser. No. 13/359,381, filed Jan. 26, 2012, which is a continuation of U.S. patent application Ser. No. 12/352,473, filed Jan. 12, 2009, now U.S. Pat. No. 8,124,429 which claims priority to U.S. Provisional Application No. 61/109,114, filed Oct. 28, 2008 and U.S. Provisional Application No. 61/020,624 filed on Jan. 11, 2008, each of which are specifically incorporated herein by reference without disclaimer.

BACKGROUND OF THE INVENTION

I. Field of the Invention

The present invention relates generally to the fields of biology and medicine. More particularly, it concerns compositions and methods for treating and/or preventing renal/kidney disease (RKD), insulin resistance, diabetes, endothelial dysfunction, fatty liver disease, and cardiovascular disease (CVD).

II. Description of Related Art

Renal failure, resulting in inadequate clearance of metabolic waste products from the blood and abnormal concentrations of electrolytes in the blood, is a significant medical problem throughout the world, especially in developed countries. Diabetes and hypertension are among the most important causes of chronic renal failure, also known as chronic kidney disease (CKD), but it is also associated with other conditions such as lupus or systemic cardiovascular disease. Dysfunction of the vascular endothelium commonly occurs in such conditions and is believed to be a major contributing factor in the development of chronic kidney disease. Acute renal failure may arise from exposure to certain drugs (e.g., acetaminophen) or toxic chemicals or from ischemia-reperfusion injury associated with shock or surgical procedures such as transplantation, and may ultimately result in CKD. In many patients, CKD advances to end-stage renal disease (ESRD) in which the patient requires kidney transplantation or regular dialysis to continue living. Both of these procedures are highly invasive and associated with significant side effects and quality of life issues. Although there are effective treatments for some complications of renal failure, such as hyperparathyroidism and hyperphosphatemia, no available treatment has been shown to halt or reverse the underlying progression of renal failure. Thus, agents that can improve compromised renal function would represent a significant advance in the treatment of renal failure.

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally-occurring molecules is relatively weak, and therefore the synthesis of new analogs to enhance their potency was undertaken (Honda et al., 1997; Honda et al., 1998). An ongoing effort for the improvement of anti-inflammatory and antiproliferative activity of oleanolic and ursolic acid analogs led to the discovery of 2-cyano-3,12-dioxooleane-1,9(11)-dien-28-oic acid (CDDO) and related compounds (Honda et al., 1997, 1998, 1999, 2000a, 2000b, 2002; Suh et al., 1998; 1999; 2003; Place et al., 2003; Liby et al., 2005). Several potent derivatives of oleanolic acid were identified, including methyl-2-cyano-3,12-dioxoooleana-1,9-dien-28-oic acid (CDDO-Me; RTA 402). RTA 402 suppresses the induction of several important inflammatory mediators, such as iNOS, COX-2, TNFα, and IFNγ, in activated macrophages. RTA 402 has also been reported to activate the Keap1/Nrf2/ARE signaling pathway resulting in the production of several anti-inflammatory and antioxidant proteins, such as heme oxygenase-1 (HO-1). These properties have made RTA 402 a candidate for the treatment of neoplastic and proliferative diseases, such as cancer. The ability of this compound and related molecules to treat and/or prevent kidney disease and cardiovascular disease remains untested.

SUMMARY OF THE INVENTION

The present invention provides new methods for treating and/or preventing renal/kidney disease (RKD), insulin resistance, diabetes, endothelial dysfunction, fatty liver disease, cardiovascular disease (CVD), and related disorders. Compounds covered by the generic or specific formulas below or specifically named are referred to as "compounds of the invention," "compounds of the present invention," or "synthetic triterpenoids" in the present application.

In one aspect of the present prevention, methods are provided for treating or preventing renal/kidney disease (RKD), insulin resistance, diabetes, endothelial dysfunction, fatty liver disease, or cardiovascular disease (CVD) in a subject comprising, administering to said subject a pharmaceutically effective amount of a compound having the structure:

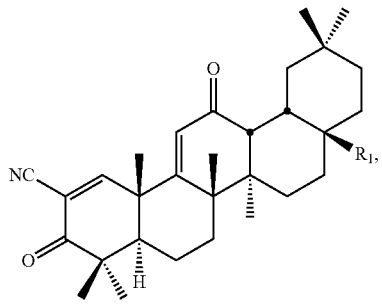

Formula I wherein $R_1$ is: —CN, or $C_1$-$C_{15}$-acyl or $C_1$-$C_{15}$-alkyl, wherein either of these groups is heteroatom-substituted or heteroatom-unsubstituted; or a pharmaceutically acceptable salt, hydrate or solvate thereof.

In some embodiments, methods are provided for treating RKD. In some variations, the RKD is diabetic nephropathy (DN). In other variations, the RKD results from a toxic insult, for example, wherein the toxic insult results from an imaging agent or a drug. For example, the drug may be a chemotherapeutic agent. In a further variation, the RKD results from ischemia/reperfusion injury. In yet a further variation, the RKD results from diabetes or hypertension. In still further variations, the RKD results from an autoimmune disease. In other variations, the RKD is chronic RKD. In still other variations, the RKD is acute RKD.

In some embodiments, the subject has undergone or is undergoing dialysis. In some embodiments, the subject has undergone or is a candidate to undergo kidney transplant. In some embodiments, the subject has RKD and insulin resistance. In some variations on the above embodiments, the subject has RKD, insulin resistance and endothelial dysfunction. In some embodiments, the subject has RKD and diabetes. In some embodiments, the subject has insulin resistance.

In some embodiments, the subject has diabetes. The pharmaceutically effective amount of the compound may also effectively treat one or more complications associated with diabetes. For example, the complications can be selected from the group consisting of obesity, hypertension, atherosclerosis, coronary heart disease, stroke, peripheral vascular disease, hypertension, nephropathy, neuropathy, myonecrosis, diabetic foot ulcers and other diabetic ulcers, retinopathy and metabolic syndrome (syndrome X). Also, for example, the complication can be metabolic syndrome (syndrome X). In some variations, the diabetes results from insulin resistance.

In some embodiments, the subject has RKD and endothelial dysfunction. In other embodiments, the subject has RKD and cardiovascular disease. In some embodiments, the subject has CVD. In some variations, the CVD results from endothelial dysfunction.

In some embodiments, the subject has endothelial dysfunction and/or insulin resistance. In some embodiments, the subject has fatty liver disease. In some variations, the fatty liver disease is non-alcoholic fatty liver disease. In other variations, the fatty liver disease is alcoholic fatty liver disease. In some variations, the subject has fatty liver disease and one or more of the following disorders: renal/kidney disease (RKD), insulin resistance, diabetes, endothelial dysfunction, and cardiovascular disease (CVD).

In some embodiments, the methods further comprise identifying a subject in need of treatment of any of the diseases, dysfunctions, resistances or disorders listed herein. In some embodiments, the subject has a family or patient history of any of the diseases, dysfunctions, resistances or disorders listed herein. In some embodiments, the subject exhibits symptoms of any of the diseases, dysfunctions, resistances or disorders listed herein.

In another aspect of the invention, a method is provided for improving glomerular filtration rate or creatinine clearance in a subject comprising, administering to said subject a pharmaceutically effective amount of a compound having the structure of Formula I, or a pharmaceutically acceptable salt, hydrate or solvate thereof.

In some embodiments, the compound is administered locally. In some embodiments, the compound is administered systemically. In some embodiments, the compound is administered orally, intraadiposally, intraarterially, intraarticularly, intracranially, intradermally, intralesionally, intramuscularly, intranasally, intraocularally, intrapericardially, intraperitoneally, intrapleurally, intraprostatically, intrarectally, intrathecally, intratracheally, intratumorally, intraumbilically, intravaginally, intravenously, intravesicularily, intravitreally, liposomally, locally, mucosally, orally, parenterally, rectally, subconjunctivally, subcutaneously, sublingually, topically, transbuccally, transdermally, vaginally, in crèmes, in lipid compositions, via a catheter, via a lavage, via continuous infusion, via infusion, via inhalation, via injection, via local delivery, via localized perfusion, bathing target cells directly, or any combination thereof. For example, in some variations, the compound is administered intravenously, intraarterially or orally. For example, in some variations, the compound is administered orally.

In some embodiments, the compound is formulated as a hard or soft capsule, a tablet, a syrup, a suspension, a solid dispersion, a wafer, or an elixir. In some variations, the soft capsule is a gelatin capsule. In variations, the compound is formulated as a solid dispersion. In some variations the hard capsule, soft capsule, tablet or wafer further comprises a protective coating. In some variations, the formulated compound comprises an agent that delays absorption. In some variations, the formulated compound further comprises an agent that enhances solubility or dispersibility. In some variations, the compound is dispersed in a liposome, an oil in water emulsion or a water in oil emulsion.

In some embodiments, the pharmaceutically effective amount is a daily dose from about 0.1 mg to about 500 mg of the compound. In some variations, the daily dose is from about 1 mg to about 300 mg of the compound. In some variations, the daily dose is from about 10 mg to about 200 mg of the compound. In some variations, the daily dose is about 25 mg of the compound. In other variations, the daily dose is about 75 mg of the compound. In still other variations, the daily dose is about 150 mg of the compound. In further variations, the daily dose is from about 0.1 mg to about 30 mg of the compound. In some variations, the daily dose is from about 0.5 mg to about 20 mg of the compound. In some variations, the daily dose is from about 1 mg to about 15 mg of the compound. In some variations, the daily dose is from about 1 mg to about 10 mg of the compound. In some variations, the daily dose is from about 1 mg to about 5 mg of the compound.

In some embodiments, the pharmaceutically effective amount is a daily dose is 0.01-25 mg of compound per kg of body weight. In some variations, the daily dose is 0.05-20 mg of compound per kg of body weight. In some variations, the daily dose is 0.1-10 mg of compound per kg of body weight. In some variations, the daily dose is 0.1-5 mg of compound per kg of body weight. In some variations, the daily dose is 0.1-2.5 mg of compound per kg of body weight.

In some embodiments, the pharmaceutically effective amount is administered in a single dose per day. In some embodiments, the pharmaceutically effective amount is administered in two or more doses per day.

In some embodiments, the treatment method further comprises a second therapy. In some variations, the second therapy comprises administering to said subject a pharmaceutically effective amount of a second drug. In some embodiments, the second drug is a cholesterol lowering drug, an anti-hyperlipidemic, a calcium channel blocker, an anti-hypertensive, or an HMG-CoA reductase inhibitor. Non-limiting examples of second drugs are amlodipine, aspirin, ezetimibe, felodipine, lacidipine, lercanidipine, nicardipine, nifedipine, nimodipine, nisoldipine and nitrendipine. Further non-limiting examples of second drugs are atenolol, bucindolol, carvedilol, clonidine, doxazosin, indoramin, labetalol, methyldopa, metoprolol, nadolol, oxprenolol, phenoxybenzamine, phentolamine, pindolol, prazosin, propranolol, terazosin, timolol and tolazoline. In some variations, the second drug is a statin. Non-limiting examples of statins are atorvastatin, cerivastatin, fluvastatin, lovastatin, mevastatin, pitavastatin, pravastatin, rosuvastatin and simvastatin. In some variations, the second drug is a dipeptidyl peptidase-4 (DPP-4) inhibitor. Non-limiting examples of DPP-4 inhibitors are sitagliptin, vildagliptin, SYR-322, BMS 477118 and GSK 823093. In some variations, the second drug is a biguanide. For example, the biguanide can be metformin. In some variations, the second drug is a thiazolidinedione (TZD). Non-limiting examples of TZDs are pioglitazone, rosiglitazone and troglitazone. In some variations, the second drug is a sulfonylurea derivative. Non-limiting examples of sulfonyl urea derivatives are tolbutamide, acetohexamide, tolazamide, chlorpropamide, glipizide, glyburide, glimepiride and gliclazide. In some variations, the second drug is a meglitinide. Non-limiting examples of meglitinides include repaglinide, mitiglinide and nateglinide. In some variations, the second drug is insulin. In some variations, the second drug is an alpha-glucosidase inhibitor. Non-limiting examples of alpha-glucosidase inhibitors are acarbose, miglitol and voglibose. In some variations, the second drug is a glucagon-like peptide-1 analog. Non-limiting examples of glucagon-like peptide-1 analogs are exenatide and liraglutide. In some variations, the second drug is a gastric inhibitory peptide analog. In some variations, the second drug is a GPR40 agonist. In some variations, the second drug is a GPR119 agonist. In some variations the second drug is a GPR30 agonist. In some variations, the second drug is a glucokinase activator. In some variations, the second drug is a glucagon receptor antagonist. In some variations, the second drug is an amylin analog. A non-limiting example of an amylin analog is pramlintide. In some variations, the second drug is an IL-1β receptor antagonist. A non-limiting examples of a IL-1β receptor antagonist is anakinra. In some variations, the second drug is an endocannabinoid receptor antagonist or inverse agonist. A non-limiting example of a endocannabinoid receptor antagonist or inverse agonist is rimonabant. In some variations, the second drug is Orlistat. In some variations, the second drug is Sibutramine. In some variations, the second drug is a growth factor. Non-limiting examples of growth factors are TGF-β1, TGF-β2, TGF-β1.2, VEGF, insulin-like growth factor I or II, BMP2, BMP4, BMP7, a GLP-1 analog, a GIP analog, a DPP-IV inhibitor, a GPR119 agonist, a GPR40 agonist, gastrin, EGF, betacellulin, KGF, NGF, insulin, growth hormone, HGF, an FGF, an FGF homologue, PDGF, Leptin, prolactin, placental lactogen, PTHrP, activin, inhibin, and INGAP. Further non-limiting examples of growth factors are parathyroid hormone, calcitonin, interleukin-6, and interleukin-11.

In some embodiments, the subject is a primate. In some variations, the primate is a human. In other variations, the subject is a cow, horse, dog, cat, pig, mouse, rat or guinea pig.

In some embodiments, the compound is defined as:

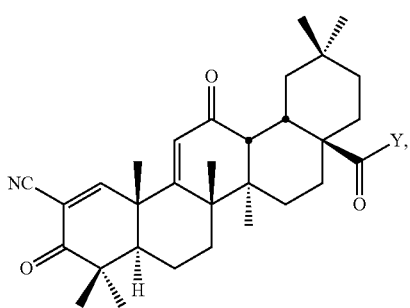

Formula II wherein Y is: —H, hydroxy, amino, halo, or $C_1$-$C_{14}$-alkoxy, $C_2$-$C_{14}$-alkenyloxy, $C_2$-$C_{14}$-alkynyloxy, $C_1$-$C_{14}$-aryloxy, $C_2$-$C_{14}$-aralkoxy, $C_1$-$C_{14}$-alkylamino, $C_2$-$C_{14}$-alkenylamino, $C_2$-$C_{14}$-alkynylamino, $C_1$-$C_{14}$-arylamino, $C_3$-$C_{10}$-aryl, or $C_2$-$C_{14}$-aralkylamino, wherein any of these groups is heteroatom-substituted or heteroatom-unsubstituted; or a pharmaceutically acceptable salt, hydrate or solvate thereof.

In some embodiments, Y is a heteroatom-unsubstituted $C_1$-$C_4$-alkylamino, such that the compound of the invention is, for example:

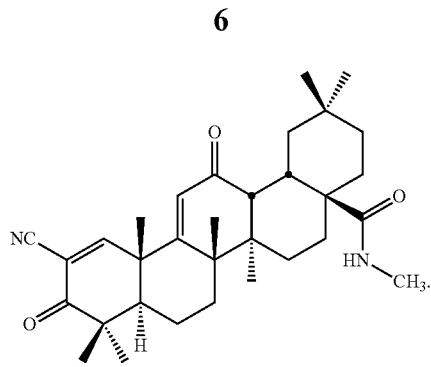

In some embodiments, Y is a heteroatom-substituted or heteroatom-unsubstituted $C_2$-$C_4$-alkylamino, such that the compound of the invention is, for example:

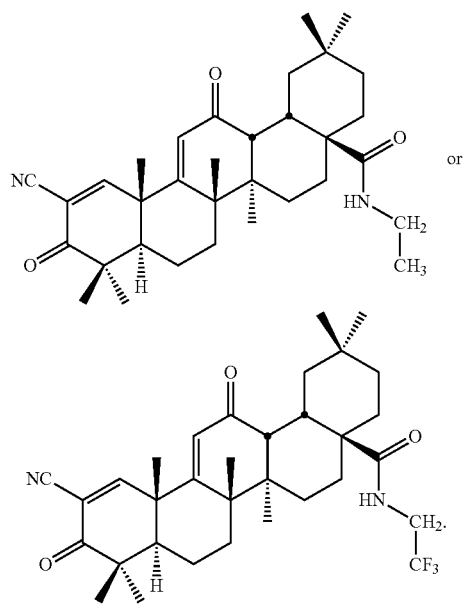

In some embodiments, Y is a heteroatom-substituted or heteroatom-unsubstituted $C_1$-$C_4$-alkoxy, such as a heteroatom-unsubstituted $C_1$-$C_2$-alkoxy. For example, one non-limiting example of such a compound is:

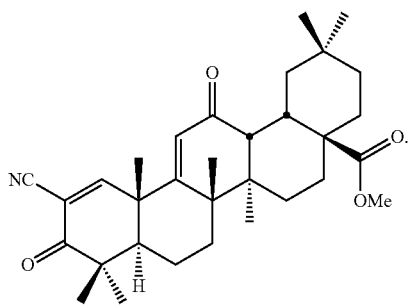

(CDDO-Me, RTA 402)

In some embodiments, at least a portion of the CDDO-Me is present as a polymorphic form, wherein the polymorphic form is a crystalline form having an X-ray diffraction pattern (CuKα) comprising significant diffraction peaks at about 8.8, 12.9, 13.4, 14.2 and 17.4°2θ. In non-limiting examples, the X-ray diffraction pattern (CuKα) is substantially as shown in FIG. 12A or FIG. 12B. In other variations, at least a portion of the CDDO-Me is present as a polymorphic form, wherein the polymorphic form is an amorphous form having an X-ray diffraction pattern (CuKα) with a halo peak at approximately 13.5°2θ, substantially as shown in FIG. 12C, and a $T_g$. In some variations, the compound is an amorphous form. In some variations, the compound is a glassy solid form of CDDO-Me, having an X-ray powder diffraction pattern with a halo peak at about 13.5°2θ, as shown in FIG. 12C, and a $T_g$. In some variations, the $T_g$ value falls within a range of about 120° C. to about 135° C. In some variations, the $T_g$ value is from about 125° C. to about 130° C.

In some embodiments, Y is hydroxy, such that the compound of the invention is, for example:

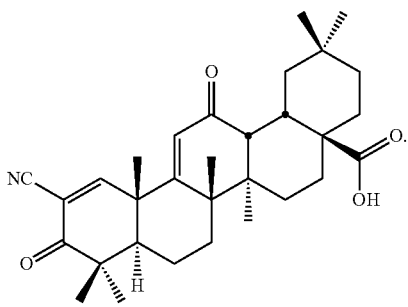

In some embodiments, the compound is:

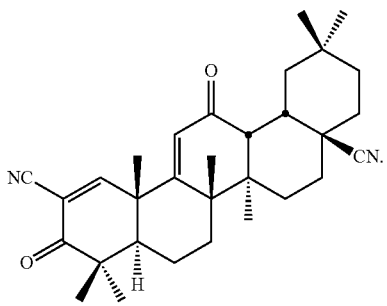

In some embodiments, the compound is defined as:

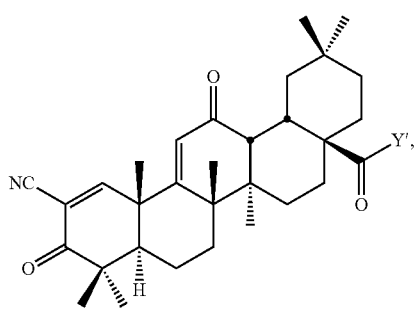

Formula III wherein Y' is a heteroatom-substituted or heteroatom-unsubstituted $C_1$-$C_{14}$-aryl; or a pharmaceutically acceptable salt, hydrate or solvate thereof.

In some embodiments, the compound is:

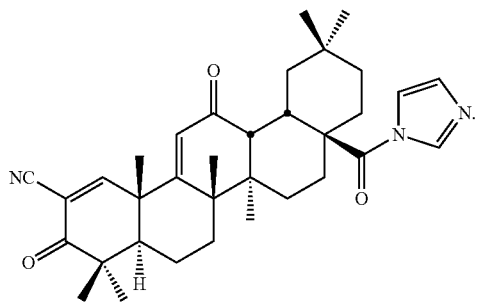

In some variations of the above methods, the compound is substantially free from optical isomers thereof. In some variations of the above methods, the compound is in the form of a pharmaceutically acceptable salt. In other variations of the above methods, the compound is not a salt.

In some embodiments, the compound is formulated as a pharmaceutical composition comprising (i) a therapeutically effective amount of the compound and (ii) an excipient is selected from the group consisting of (A) a carbohydrate, carbohydrate derivative, or carbohydrate polymer, (B) a synthetic organic polymer, (C) an organic acid salt, (D) a protein, polypeptide, or peptide, and (E) a high molecular weight polysaccharide. In some variations, the excipient is a synthetic organic polymer. In some variations, the excipient is selected from the group consisting of a hydroxpropyl methyl cellulose, a poly[1-(2-oxo-1-pyrrolidinyl)ethylene or copolymer thereof, and a methacrylic acid-methylmethacrylate copolymer. In some variations, the excipient is hydroxpropyl methyl cellulose phthalate ester. In some variations, the excipient is PVP/VA. In some variations, the excipient is a methacrylic acid-ethyl acrylate copolymer (1:1). In some variations, the excipient is copovidone.

Any embodiment discussed herein with respect to one aspect of the invention applies to other aspects of the invention as well, unless specifically noted.

Other objects, features and advantages of the present invention will become apparent from the following detailed description and any accompanying drawings. It should be understood, however, that the detailed description and any specific examples or drawings provided, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1a) On Day 1, blood was collected from animals that were subjected to clamping and "sham" control animals that underwent surgery without clamping of the renal artery. Blood urea nitrogen (BUN)

levels were measured as a surrogate for renal damage. (FIGS. 1b-d) Sections of kidneys from RTA 402-treated or vehicle-treated mice were scored for histological damage (FIGS. 1b & 1d) and inflammation (FIG. 1c). (FIG. 1d) Black arrows (vehicle group) show two of many severely damaged tubules in the outer medulla. Red arrows (RTA 402 group) show two of many undamaged tubules in the outer medulla.

(FIG. 2c) Less damage to the proximal tubules is observed in RTA 402-treated animals compared to vehicle-treated animals.

(FIG. 3a) Cynomolgus monkeys were administered RTA 402 orally at the indicated doses once daily for 28 days. The percent reduction of serum creatinine on Day 28 in RTA 402-treated monkeys relative to vehicle-treated control monkeys is shown. (FIG. 3b) RTA 402 was administered orally to beagle dogs at the indicated doses daily for three months. Control animals received vehicle (sesame oil). The percent change in serum creatinine at the three-month time point relative to baseline is shown. (FIG. 3c) Sprague-Dawley rats were administered RTA 402 orally at the indicated doses once daily for a period of one month. The percent reduction of serum creatinine at study completion in RTA 402-treated rats relative to vehicle-treated control rats is shown. (FIG. 3d) Sprague-Dawley rats were administered the amorphous form of RTA 402 orally at the indicated doses once daily for a period of three months. The percent reduction of serum creatinine at study completion in RTA 402-treated rats relative to vehicle-treated control rats is shown. Note: in FIGS. 3a, 3c and 3d, "% reduction" on the vertical axis indicates percent change. For example, a reading of −15 on this axis indicates a 15% reduction in serum creatinine.

FIG. 4A: Serum creatinine was measured in RTA 402-treated patients enrolled in a Phase I clinical trial for the treatment of cancer. The patients were administered RTA 402 (p.o.) once daily for 21 days at doses ranging from 5 to 1,300 mg/day. The percent reduction of serum creatinine relative to baseline levels is shown for the indicated study days. Significant decreases in serum creatinine levels were observed on Days 15 and 21. FIG. 4B: The estimated glomerular filtration rate (eGFR) was calculated for the patients in FIG. 4A. Significant improvements in the eGFR were observed in both groups. All patients: n=24; patients with baseline ≥1.5: n=5. For FIGS. 4A and 4B, * indicates p≤0.04; † indicates p=0.01, and ‡ indicates p≤0.01. Note: in FIG. 4A, "% Reduction from Baseline" on the vertical axis indicates percent change. For example, a reading of −15 on this axis indicates a 15% reduction in serum creatinine.

FIG. 12A shows unmicronized Form A; FIG. 12B shows micronized Form A; FIG. 12C shows Form B.

DESCRIPTION OF ILLUSTRATIVE EMBODIMENTS

I. The Present Invention

Figure 1:
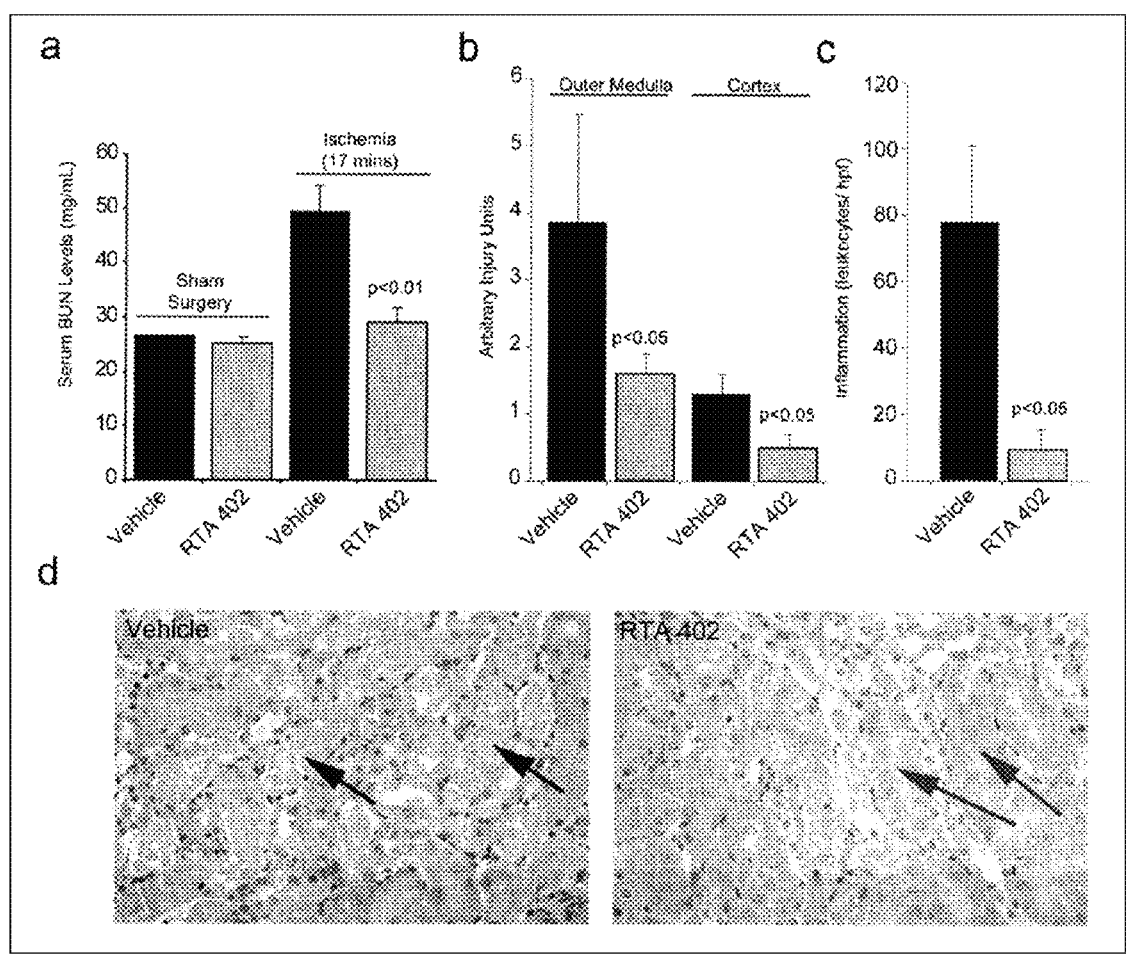
FIGS. 1a-d—RTA 402 reduces renal damage following ischemia-reperfusion. Mice were administered RTA 402 at 2 mg/kg or simply the vehicle (sesame oil) daily by oral gavage beginning on Day 2. On Day 0, a clamp was placed on the left renal artery for 17 minutes and then removed to induce ischemia-reperfusion.

The present invention concerns new methods for the treatment and prevention of renal disease and related disorders, including diabetes and cardiovascular disease, involving the use of triterpenoids.

II. Definitions

As used herein, the term "amino" means —$NH_2$; the term "nitro" means —$NO_2$; the term "halo" designates —F, —Cl, —Br or —I; the term "mercapto" means —SH; the term "cyano" means —CN; the term "silyl" means —$SiH_3$, and the term "hydroxy" means —OH.

The term "heteroatom-substituted," when used to modify a class of organic radicals (e.g., alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, =O, =S, —$NO_2$, —$N(CH_3)_2$, amino, or —SH. Specific heteroatom-substituted organic radicals are defined more fully below.

The term "heteroatom-unsubstituted," when used to modify a class of organic radicals (e.g., alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group —$C_6H_4C\equiv CH$ is an example of a heteroatom-unsubstituted aryl group, while —$C_6H_4F$ is an example of a heteroatom-substituted aryl group. Specific heteroatom-unsubstituted organic radicals are defined more fully below.

The term "alkyl" includes straight-chain alkyl groups, branched-chain alkyl groups, cycloalkyl (alicyclic) groups, alkyl heteroatom-substituted cycloalkyl groups, and cycloalkyl heteroatom-substituted alkyl groups. The term "heteroatom-unsubstituted $C_n$-alkyl" refers to a radical having a linear or branched, cyclic or acyclic structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —$CH_3$, —$CH_2CH_3$, —$CH_2CH_2CH_3$, —$CH(CH_3)_2$, —$CH(CH_2)_2$ (cyclopropyl), —$CH_2CH_2CH_2CH_3$, —$CH(CH_3)CH_2CH_3$, —$CH_2CH(CH_3)_2$, —$C(CH_3)_3$, —$CH_2C(CH_3)_3$, cyclobutyl, cyclopentyl, and cyclohexyl, are all examples of heteroatom-unsubstituted alkyl groups. The term "heteroatom-substituted $C_n$-alkyl" refers to a radical having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all examples of heteroatom-substituted alkyl groups: trifluoromethyl, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH(CH_2)_2$, —$CH_2OCH_2CF_3$, —$CH_2OCOCH_3$, —$CH_2NH_2$, —$CH_2NHCH_3$, —$CH_2N(CH_3)_2$, —$CH_2NHCH_2CH_3$, —$CH_2N(CH_3)CH_2CH$, —$CH_2NHCH_2CH_2CH_3$, —$CH_2NHCH(CH_3)_2$, —$CH_2NHCH(CH_2)_2$, —$CH_2N(CH_2CH_3)_2$, —$CH_2CH_2F$, —$CH_2CH_2Cl$, —$CH_2CH_2Br$, —$CH_2CH_2I$, —$CH_2CH_2OH$, —$CH_2CH_2OCOCH_3$, —$CH_2CH_2NH_2$, —$CH_2CH_2N(CH_3)_2$, —$CH_2CH_2NHCH_2CH_3$, —$CH_2CH_2N(CH_3)CH_2CH_3$, —$CH_2CH_2NHCH_2CH_2CH_3$, —$CH_2CH_2NHCH(CH_3)_2$, —$CH_2CH_2NHCH(CH_2)_2$, —$CH_2CH_2N(CH_2CH_3)_2$, —$CH_2CH_2NHCO_2C(CH_3)_3$, and —$CH_2Si(CH_3)_3$.

The term "heteroatom-unsubstituted $C_n$-alkenyl" refers to a radical having a linear or branched, cyclic or acyclic structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —$CH=CH_2$, —$CH=CHCH_3$, —$CH=CHCH_2CH_3$, —$CH=CHCH_2CH_2CH_3$, —$CH=CHCH(CH_3)_2$, —$CH=CHCH(CH_2)_2$, —$CH_2CH=CH_2$, —$CH_2CH=CHCH_3$, —$CH_2CH=CHCH_2CH_3$, —$CH_2CH=CHCH_2CH_2CH_3$, —$CH_2CH=CHCH(CH_3)_2$, —$CH_2CH=CHCH(CH_2)_2$, and —$CH=CH-C_6H_5$. The term "heteroatom-substituted $C_n$-alkenyl" refers to a radical having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —$CH=CHF$, —$CH=CHCl$ and —$CH=CHBr$, are examples of heteroatom-substituted alkenyl groups.

The term "heteroatom-unsubstituted $C_n$-alkynyl" refers to a radical having a linear or branched, cyclic or acyclic structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —$C\equiv CH$, —$C\equiv CCH_3$, and —$C\equiv CC_6H_5$ are examples of heteroatom-unsubstituted alkynyl groups. The term "heteroatom-substituted $C_n$-alkynyl" refers to a radical having a single nonaromatic carbon atom as the point of attachment and at least one carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —$C\equiv CSi(CH_3)_3$, is an example of a heteroatom-substituted alkynyl group.

The term "heteroatom-unsubstituted $C_n$-aryl" refers to a radical having a single carbon atom as a point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Examples of heteroatom-unsubstituted aryl groups include phenyl, methylphenyl, (dimethyl)phenyl, —$C_6H_4CH_2CH_3$, —$C_6H_4CH_2CH_2CH_3$, —$C_6H_4CH(CH_3)_2$, —$CH_4CH(CH_2)_2$, —$C_6H_3(CH_3)CH_2CH_3$, —$C_6H_4CH=CH_2$, —$C_6H_4CH=CHCH_3$, —$C_6H_4C\equiv CH$, —$C_6H_4C\equiv CCH_3$, naphthyl, and the radical derived from biphenyl. The term "heteroatom-unsubstituted aryl" includes carbocyclic aryl groups, biaryl groups, and radicals derived from polycyclic fused hydrocarbons (PAHs). The term "heteroatom-substituted $C_n$-aryl" refers to a radical having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. The term "heteroatom-substituted aryl" includes heteroaryl groups. It also includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like. Further examples of heteroatom-substituted aryl groups include the groups: —$C_6H_4F$, —$C_6H_4Cl$, —$C_6H_4Br$, —$C_6H_4I$, —$C_6H_4OH$, —$C_6H_4OCH_3$, —$C_6H_4OCH_2CH_3$, —$C_6H_4OCOCH_3$, —$C_6H_4OC_6H_5$, —$C_6H_4NH_2$, —$C_6H_4NHCH_3$, —$C_6H_4NHCH_2CH_3$, —$C_6H_4CH_2Cl$, —$C_6H_4CH_2Br$, —$C_6H_4CH_2OH$, —$C_6H_4CH_2OCOCH_3$, —$C_6H_4CH_2NH_2$, —$C_6H_4N(CH_3)_2$, —$C_6H_4CH_2CH_2Cl$, —$C_6H_4CH_2CH_2OH$, —$C_6H_4CH_2CH_2OCOCH_3$, —$C_6H_4CH_2CH_2NH_2$, —$C_6H_4CH_2CH$=$CH_2$, —$C_6H_4CF_3$, —$C_6H_4CN$, —$C_6H_4C$≡$CSi(CH_3)_3$, —$C_6H_4COH$, —$C_6H_4COCH_3$, —$C_6H_4COCH_2CH_3$, —$C_6H_4COCH_2CF_3$, —$C_6H_4COC_6H_5$, —$C_6H_4CO_2H$, —$C_6H_4CO_2CH_3$, —$C_6H_4CONH_2$, —$C_6H_4CONHCH_3$, —$C_6H_4CON(CH_3)_2$, furanyl, thienyl, pyridyl, pyrrolyl, pyrimidyl, pyrazinyl, imidazoyl, quinolyl and indolyl.

The term "heteroatom-unsubstituted $C_n$-aralkyl" refers to a radical having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, a heteroatom-unsubstituted $C_7$-$C_{10}$-aralkyl has 7 to 10 carbon atoms. Examples of heteroatom-unsubstituted aralkyls include phenylmethyl (benzyl) and phenylethyl. The term "heteroatom-substituted $C_n$-aralkyl" refers to a radical having a single saturated carbon atom as the point of attachment, further having a total of n carbon atoms, 0, 1, or more than one hydrogen atom, and at least one heteroatom, wherein at least one of the carbon atoms is incorporated in an aromatic ring structure, further wherein each heteroatom is independently selected from the group consisting of N, O, F, Cl, Br, I, Si, P, and S. For example, a heteroatom-substituted $C_2$-$C_{10}$-heteroaralkyl has 2 to 10 carbon atoms.

The term "heteroatom-unsubstituted $C_n$-acyl" refers to a radical having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —COH, —$COCH_3$, —$COCH_2CH_3$, —$COCH_2CH_2CH_3$, —$COCH(CH_3)_2$, —$COCH(CH_2)_2$, —$COC_6H_5$, —$COC_6H_4CH_3$, —$COC_6H_4CH_2CH_3$, —$COC_6H_4CH_2CH_2CH_3$, —$COC_6H_4CH(CH_3)_2$, —$COC_6H_4CH(CH_2)_2$, and —$COC_6H_3(CH_3)_2$, are examples of heteroatom-unsubstituted acyl groups. The term "heteroatom-substituted $C_n$-acyl" refers to a radical having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The term heteroatom-substituted acyl includes carbamoyl, thiocarboxylate, and thiocarboxylic acid groups. The groups, —$COCH_2CF_3$, —$CO_2H$, —$CO_2CH_3$, —$CO_2CH_2CH_3$, —$CO_2CH_2CH_2CH_3$, —$CO_2CH(CH_3)_2$, —$CO_2CH(CH_2)_2$, —$CONH_2$, —$CONHCH_3$, —$CONHCH_2CH_3$, —$CONHCH_2CH_2CH_3$, —$CONHCH(CH_3)_2$, —$CONHCH(CH_2)_2$, —$CON(CH_3)_2$, —$CON(CH_2CH_3)CH_3$, —$CON(CH_2CH_3)_2$ and —$CONHCH_2CF_3$, are examples of heteroatom-substituted acyl groups.

The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —$OCH_3$, —$OCH_2CH_3$, —$OCH_2CH_2CH_3$, —$OCH(CH_3)_2$, and —$OCH(CH_2)_2$. The term "heteroatom-substituted $C_n$-alkoxy" refers to a group, having the structure —OR, in which R is a heteroatom-substituted $C_n$-alkyl, as that term is defined above. For example, —$OCH_2CF_3$ is a heteroatom-substituted alkoxy group.

The term "heteroatom-unsubstituted $C_n$-alkenyloxy" refers to a group, having the structure —OR, in which R is a heteroatom-unsubstituted $C_n$-alkenyl, as that term is defined above. The term "heteroatom-substituted $C_n$-alkenyloxy" refers to a group, having the structure —OR, in which R is a heteroatom-substituted $C_n$-alkenyl, as that term is defined above.

The term "heteroatom-unsubstituted $C_n$-alkynyloxy" refers to a group, having the structure —OR, in which R is a heteroatom-unsubstituted $C_n$-alkynyl, as that term is defined above. The term "heteroatom-substituted $C_n$-alkynyloxy" refers to a group, having the structure —OR, in which R is a heteroatom-substituted $C_n$-alkynyl, as that term is defined above.

The term "heteroatom-unsubstituted $C_n$-aryloxy" refers to a group, having the structure —OAr, in which Ar is a heteroatom-unsubstituted $C_n$-aryl, as that term is defined above. An example of a heteroatom-unsubstituted aryloxy group is —$OC_6H_5$. The term "heteroatom-substituted $C_n$-aryloxy" refers to a group, having the structure —OAr, in which Ar is a heteroatom-substituted $C_n$-aryl, as that term is defined above.

The term "heteroatom-unsubstituted $C_n$-aralkyloxy" refers to a group, having the structure —$OR_{Ar}$, in which $R_{Ar}$ is a heteroatom-unsubstituted $C_n$-aralkyl, as that term is defined above. The term "heteroatom-substituted $C_n$-aralkyloxy" refers to a group, having the structure —$OR_{Ar}$, in which $R_{Ar}$ is a heteroatom-substituted $C_n$-aralkyl, as that term is defined above.

The term "heteroatom-unsubstituted $C_n$-acyloxy" refers to a group, having the structure —OAc, in which Ac is a heteroatom-unsubstituted $C_n$-acyl, as that term is defined above. A heteroatom-unsubstituted acyloxy group includes alkylcarbonyloxy and arylcarbonyloxy groups. For example, —$OCOCH_3$ is an example of a heteroatom-unsubstituted acyloxy group. The term "heteroatom-substituted $C_n$-acyloxy" refers to a group, having the structure —OAc, in which Ac is a heteroatom-substituted $C_n$-acyl, as that term is defined above. A heteroatom-substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "heteroatom-unsubstituted $C_n$-alkylamino" refers to a radical having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted $C_n$-alkylamino" refers to a radical having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "heteroatom-unsubstituted $C_n$-alkenylamino" refers to a radical having a single nitrogen atom as the point of attachment, further having one or two carbon atoms attached to the nitrogen atom, further having a linear or branched, cyclic or acyclic structure, containing at least one nonaromatic carbon-carbon double bond, a total of n carbon atoms, 4 or more hydrogen atoms, a total of one nitrogen atom, and no additional heteroatoms. For example, a heteroatom-unsubstituted $C_2$-$C_{10}$-alkenylamino has 2 to 10 carbon atoms. The term "heteroatom-unsubstituted $C_n$-alkenylamino" includes groups, having the structure —NHR, in which R is a heteroatom-unsubstituted $C_n$-alkenyl, as that term is defined above. Examples of heteroatom-unsubstituted $C_n$-alkenylamino groups also include dialkenylamino and alkyl(alkenyl)amino groups. The term "heteroatom-substituted $C_n$-alkenylamino" refers to a radical having a single nitrogen atom as the point of attachment and at least one nonaromatic carbon-carbon double bond, but no carbon-carbon triple bonds, further having one or two carbon atoms attached to the nitrogen atom, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkenylamino has 2 to 10 carbon atoms. The term "heteroatom-substituted $C_n$-alkenylamino" includes groups, having the structure —NHR, in which R is a heteroatom-substituted $C_n$-alkenyl, as that term is defined above.

The term "heteroatom-unsubstituted $C_n$-alkynylamino" refers to a radical having a single nitrogen atom as the point of attachment, further having one or two carbon atoms attached to the nitrogen atom, further having a linear or branched, cyclic or acyclic structure, containing at least one carbon-carbon triple bond, a total of n carbon atoms, at least one hydrogen atom, a total of one nitrogen atom, and no additional heteroatoms. For example, a heteroatom-unsubstituted $C_2$-$C_{10}$-alkynylamino has 2 to 10 carbon atoms. The term "heteroatom-unsubstituted $C_n$-alkynylamino" includes groups, having the structure —NHR, in which R is a heteroatom-unsubstituted $C_n$-alkynyl, as that term is defined above. An alkynylamino group includes dialkynylamino and alkyl(alkynyl)amino groups. The term "heteroatom-substituted $C_n$-alkynylamino" refers to a radical having a single nitrogen atom as the point of attachment, further having one or two carbon atoms attached to the nitrogen atom, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_2$-$C_{10}$-alkynylamino has 2 to 10 carbon atoms. The term "heteroatom-substituted $C_n$-alkynylamino" includes groups, having the structure —NHR, in which R is a heteroatom-substituted $C_n$-alkynyl, as that term is defined above.

The term "heteroatom-unsubstituted $C_n$-arylamino" refers to a radical having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, a heteroatom-unsubstituted $C_6$-$C_{10}$-arylamino has 6 to 10 carbon atoms. The term "heteroatom-unsubstituted $C_n$-arylamino" includes groups, having the structure —NHR, in which R is a heteroatom-unsubstituted $C_n$-aryl, as that term is defined above. A heteroatom-unsubstituted arylamino group includes diarylamino and alkyl(aryl)amino groups. The term "heteroatom-substituted $C_n$-arylamino" refers to a radical having a single nitrogen atom as the point of attachment, further having a total of n carbon atoms, at least one hydrogen atom, at least one additional heteroatoms, that is, in addition to the nitrogen atom at the point of attachment, wherein at least one of the carbon atoms is incorporated into one or more aromatic ring structures, further wherein each additional heteroatom is independently selected from the group consisting of N, O, F, Cl, Br, I, Si, P, and S. For example, a heteroatom-substituted $C_6$-$C_{10}$-arylamino has 6 to 10 carbon atoms. The term "heteroatom-substituted $C_n$-arylamino" includes groups, having the structure —NHR, in which R is a heteroatom-substituted $C_n$-aryl, as that term is defined above. A heteroatom-substituted arylamino group includes heteroarylamino groups.

The term "heteroatom-unsubstituted $C_n$-aralkylamino" refers to a radical having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, a heteroatom-unsubstituted $C_7$-$C_{10}$-aralkylamino has 7 to 10 carbon atoms. The term "heteroatom-unsubstituted $C_n$-aralkylamino" includes groups, having the structure —NHR, in which R is a heteroatom-unsubstituted $C_n$-aralkyl, as that term is defined above. An aralkylamino group includes diaralkylamino groups. The term "heteroatom-substituted $C_n$-aralkylamino" refers to a radical having a single nitrogen atom as the point of attachment, further having at least one or two saturated carbon atoms attached to the nitrogen atom, further having a total of n carbon atoms, 0, 1, or more than one hydrogen atom, at least one additional heteroatom, that is, in addition to the nitrogen atom at the point of attachment, wherein at least one of the carbon atom incorporated into an aromatic ring, further wherein each heteroatom is independently selected from the group consisting of N, O, F, Cl, Br, I, Si, P, and S. For example, a heteroatom-substituted $C_7$-$C_{10}$-aralkylamino has 7 to 10 carbon atoms. The term "heteroatom-substituted $C_n$-aralkylamino" includes groups, having the structure —NHR, in which R is a heteroatom-substituted $C_n$-aralkyl, as that term is defined above. The term "heteroatom-substituted aralkylamino" includes the term "heteroaralkylamino."

The term amido includes N-alkyl-amido, N-aryl-amido, N-aralkyl-amido, acylamino, alkylcarbonylamino, arylcarbonylamino, and ureido groups. The group, —NHCOCH$_3$, is an example of a heteroatom-unsubstituted amido group. The term "heteroatom-unsubstituted $C_n$-amido" refers to a radical having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, a heteroatom-unsubstituted $C_1$-$C_{10}$-amido has 1 to 10 carbon atoms. The term "heteroatom-unsubstituted $C_n$-amido" includes groups, having the structure —NHR, in which R is a heteroatom-unsubstituted $C_n$-acyl, as that term is defined above. The term "heteroatom-substituted $C_n$-amido" refers to a radical having a single nitrogen atom as the point of attachment, further having a carbonyl group attached via its carbon atom to the nitrogen atom, further having a linear or branched, cyclic or acyclic structure, further having a total of n aromatic or nonaromatic carbon atoms, 0, 1, or more than one hydrogen atom, at least one additional heteroatom in addition to the oxygen of the carbonyl group and the nitrogen atom at the point of attachment, wherein each additional heteroatom is independently selected from the group consisting of N, O, F, Cl, Br, I, Si, P, and S. For example, a heteroatom-substituted $C_1$-$C_{10}$-amido has 1 to 10 carbon atoms. The term "heteroatom-substituted $C_n$-amido" includes groups, having the structure —NHR, in which R is a heteroatom-unsubstituted $C_n$-acyl, as that term is defined above. The group, —NHCO$_2$CH$_3$, is an example of a heteroatom-substituted amido group.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Similarly, it is contemplated that one or more oxygen atom(s) of a compound of the present invention may be replaced by a sulfur or a selenium atom(s).

Any undefined valency on an atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts Properties and Use* (P. H. Stahl & C. G. Wermuth eds., Verlag Helvetica Chimica Acta, 2002).

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

"Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, the term "water soluble" means that the compound dissolves in water at least to the extent of 0.010 mole/liter or is classified as soluble according to literature precedence.

Other abbreviations used herein are as follows: DMSO, dimethyl sulfoxide; NO, nitric oxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFNγ or IFN-γ, interferon-γ; LPS, bacterial endotoxic lipopolysaccharide; TNFα or TNF-α, tumor necrosis factor-α; IL-1β, interleukin-1β; GAPDH, glyceraldehyde-3-phosphate dehydrogenase; MTBE, methyl-tert-butylether; MTT, 3-[4,5-dimethylthiazol-2-yl]-2,5-diphenyltetrazolium bromide; TCA, trichloroacetic acid; HO-1, inducible heme oxygenase.

The above definitions supersede any conflicting definition in any of the reference that is incorporated by reference herein.

III. Synthetic Triterpenoids

Triterpenoids, biosynthesized in plants by the cyclization of squalene, are used for medicinal purposes in many Asian countries; and some, like ursolic and oleanolic acids, are known to be anti-inflammatory and anti-carcinogenic (Huang et al., 1994; Nishino et al., 1988). However, the biological activity of these naturally-occurring molecules is relatively weak, and therefore the synthesis of new analogs to enhance their potency was undertaken (Honda et al., 1997; Honda et al., 1998). Subsequent research has identified a number of synthetic compounds that have improved activity as compared to the naturally-occurring triterpenoids.

The ongoing efforts for the improvement of anti-inflammatory and antiproliferative activity of oleanolic and ursolic acid analogs led to the discovery of 2-cyano-3,12-dioxooleane-1,9(11)-dien-28-oic acid (CDDO, RTA 402) and related compounds (e.g., CDDO-Me, TP-225, CDDO-Im) (Honda et al., 1997, 1998, 1999, 2000a, 2000b, 2002; Suh et al., 1998; 1999; 2003; Place et al., 2003; Liby et al., 2005). In the case of inducing cytoprotective genes through Keap1-Nrf2-antioxidant response element (ARE) signaling, a recent structure activity evaluation of 15 triterpenoids noted the importance of Michael acceptor groups on both the A and C rings, a nitrile group at C-2 of the A ring, and that substituents at C-17 affected pharmacodynamic action in vivo (Yates et al., 2007).

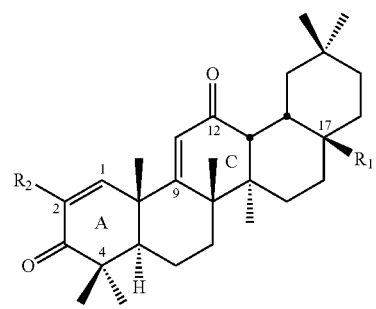

In general, CDDO is the prototype for a large number of compounds in a family of agents that have been shown useful in a variety of contexts. For example, CDDO-Me and CDDO-Im are reported to possess the ability to modulate transforming growth factor-β (TGF-β)/Smad signaling in several types of cells (Suh et al., 2003; Minns et al., 2004; Mix et al., 2004). Both are known to be potent inducers of heme-oxygenase-1 and Nrf2/ARE signaling (Liby et al., 2005), and a series of synthetic triterpenoid (TP) analogs of oleanolic acid have also been shown to be potent inducers of the phase 2 response, that is elevation of NAD(P)H-quinone oxidoreductase and heme oxygenase 1 (HO-1), which is a major protector of cells against oxidative and electrophile stress (Dinkova-Kostova et al., 2005). Like previously identified phase 2 inducers, the TP analogs were shown to use the antioxidant response element-Nrf2-Keap1 signaling pathway.

RTA 402 (bardoxolone methyl), one of the compounds for use with the methods of this invention, is an Antioxidant Inflammation Modulator (AIM) in clinical development for inflammation and cancer-related indications that inhibits immune-mediated inflammation by restoring redox homeostasis in inflamed tissues. It induces the cytoprotective transcription factor Nrf2 and suppresses the activities of the pro-oxidant and pro-inflammatory transcription factors NF-κB and STAT3. In vivo, RTA 402 has demonstrated significant single agent anti-inflammatory activity in several animal models of inflammation such as renal damage in the cisplatin model and acute renal injury in the ischemia-reperfusion model. In addition, significant reductions in serum creatinine have been observed in patients treated with RTA 402.

In one aspect of the invention, the compounds of the present invention may be used for treating a subject having a renal disease or condition caused by elevated levels of oxidative stress in one or more tissues. The oxidative stress may be accompanied by either acute or chronic inflammation. The oxidative stress may be caused by acute exposure to an external agent such as ionizing radiation or a cytotoxic chemotherapy agent (e.g., doxorubicin), by trauma or other acute tissue injury, by ischemia/reperfusion injury, by poor circulation or anemia, by localized or systemic hypoxia or hyperoxia, or by other abnormal physiological states such as hyperglycemia or hypoglycemia.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively in advance of a predictable state of oxidative stress (e.g., organ transplantation or the administration of therapy to a cancer patient), or it may be administered therapeutically in settings involving established oxidative stress and inflammation.

Newer amide derivatives of CDDO have now also been found to be promising agents, for example for their ability to pass through the blood brain barrier. In addition to the methyl amide of CDDO (CDDO-MA), as reported in Honda et al. (2002), the invention provides for the use of additional CDDO amide derivatives, such as the ethyl amide (CDDO-EA), as well fluorinated amide derivatives of CDDO, such as the 2,2,2-trifluoroethyl amide derivative of CDDO (CDDO-TFEA).

The compounds of the present invention can be prepared according to the methods taught by Honda et al. (1998), Honda et al. (2000b), Honda et al. (2002), Yates et al. (2007), and U.S. Pat. Nos. 6,326,507 and 6,974,801, which are all incorporated herein by reference.

Non-limiting examples of triterpenoids that may be used in accordance with the methods of this invention are shown here.

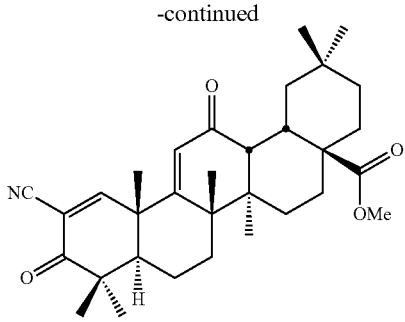

CDDO—Me
bardoxolone methyl
(TP-155)
(RTA 402)

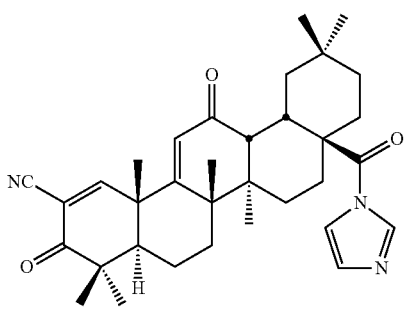

CDDO-Im
(TP-235)
(RTA 403)

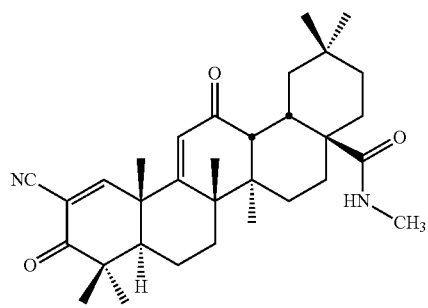

CDDO-MA
(TP-224)

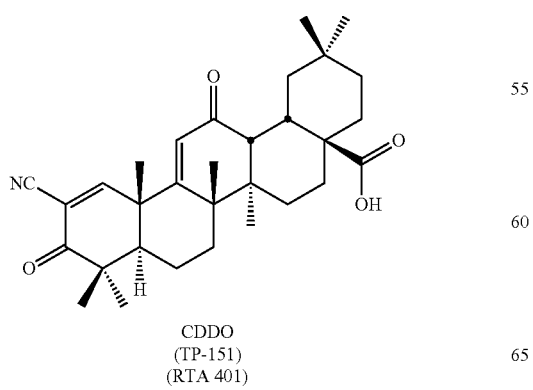

CDDO
(TP-151)
(RTA 401)

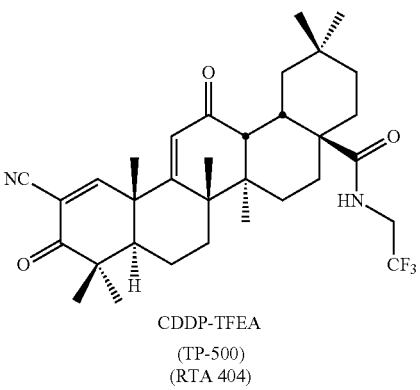

CDDP-TFEA
(TP-500)
(RTA 404)

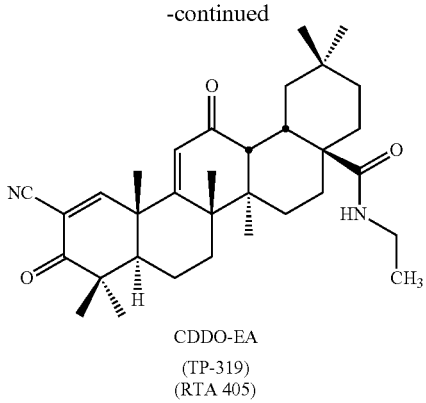

CDDO-EA
(TP-319)
(RTA 405)

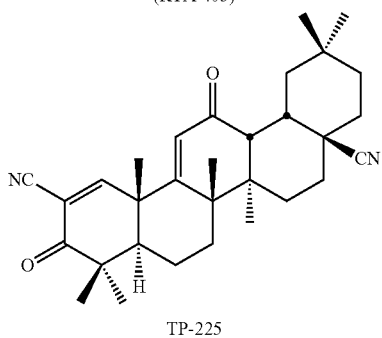

TP-225

The compounds for use with the present invention, such as those of the table above, are structurally similar to RTA 402 and in many cases exhibit similar biological properties, as has been noted above. As additional examples, Table 1 summarizes in vitro results for several of these compounds in which RAW264.7 macrophages were pre-treated with DMSO or drugs at various concentrations (nM) for 2 hours, then treated with 20 ng/ml IFNγ for 24 hours. NO concentration in media was determined using a Griess reagent system; cell viability was determined using WST-1 reagent. NQO1 CD represents the concentration required to induce a two-fold increase in the expression of NQO1, an Nrf2-regulated antioxidant enzyme, in Hepa1c1c7 murine hepatoma cells (Dinkova-Kostova et al., 2005). All these results are orders of magnitude more active than, for example, the parent oleanolic acid molecule. In part because induction of antioxidant pathways resulting from Nrf2 activation provides important protective effects against oxidative stress and inflammation, compounds related to RTA 402 may also provide significant benefits similar to those presented for RTA 402 in this application, and these related compounds may, therefore, be used for the treatment and/or prevention of diseases, such as: renal/kidney disease (RKD), insulin resistance, diabetes, endothelial dysfunction, fatty liver disease, cardiovascular disease (CVD), and related disorders.

TABLE 1

Suppression of IFNγ-induced NO production.

| Working ID | RAW264.7 (20 ng/ml IFNγ) | | Hepa1c1c7 cells |
| | NO IC$_{50}$ | WST-1 IC$_{50}$ | NQO1 CD |
| --- | --- | --- | --- |
| RTA 401 | ~10 nM | >200 nM | 2.3 nM |
| RTA 402 | 2.2 nM | 80 nM | 1.0 nM |
| RTA 403 | ~0.6 nM | 100 nM | 3.3 nM |
| RTA 404 | 5.8 nM | 100 nM | n/a |

TABLE 1-continued

Suppression of IFNγ-induced NO production.

| Working ID | RAW264.7 (20 ng/ml IFNγ) | | Hepa1c1c7 cells |
| | NO IC$_{50}$ | WST-1 IC$_{50}$ | NQO1 CD |
| --- | --- | --- | --- |
| RTA 405 | 6 nM | ~200 nM | n/a |
| TP-225 | ~0.4 nM | 75 nM | 0.28 nM |

The synthesis of CDDO-MA is discussed in Honda et al. (2002), which is incorporated herein by reference. The syntheses of CDDO-EA and CDDO-TFEA are presented in Yates et al. (2007), which is incorporated herein by reference, and shown in the Scheme 1 below.

Scheme 1

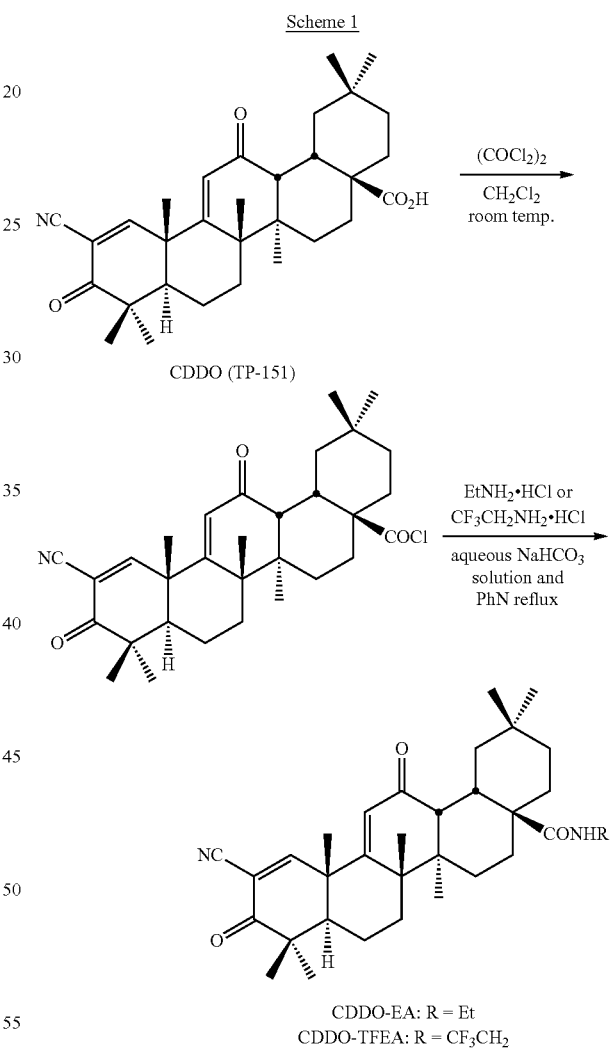

CDDO (TP-151)

CDDO-EA: R = Et
CDDO-TFEA: R = CF$_3$CH$_2$

IV. Polymorphic Forms of CDDO-Me

Figure 15:
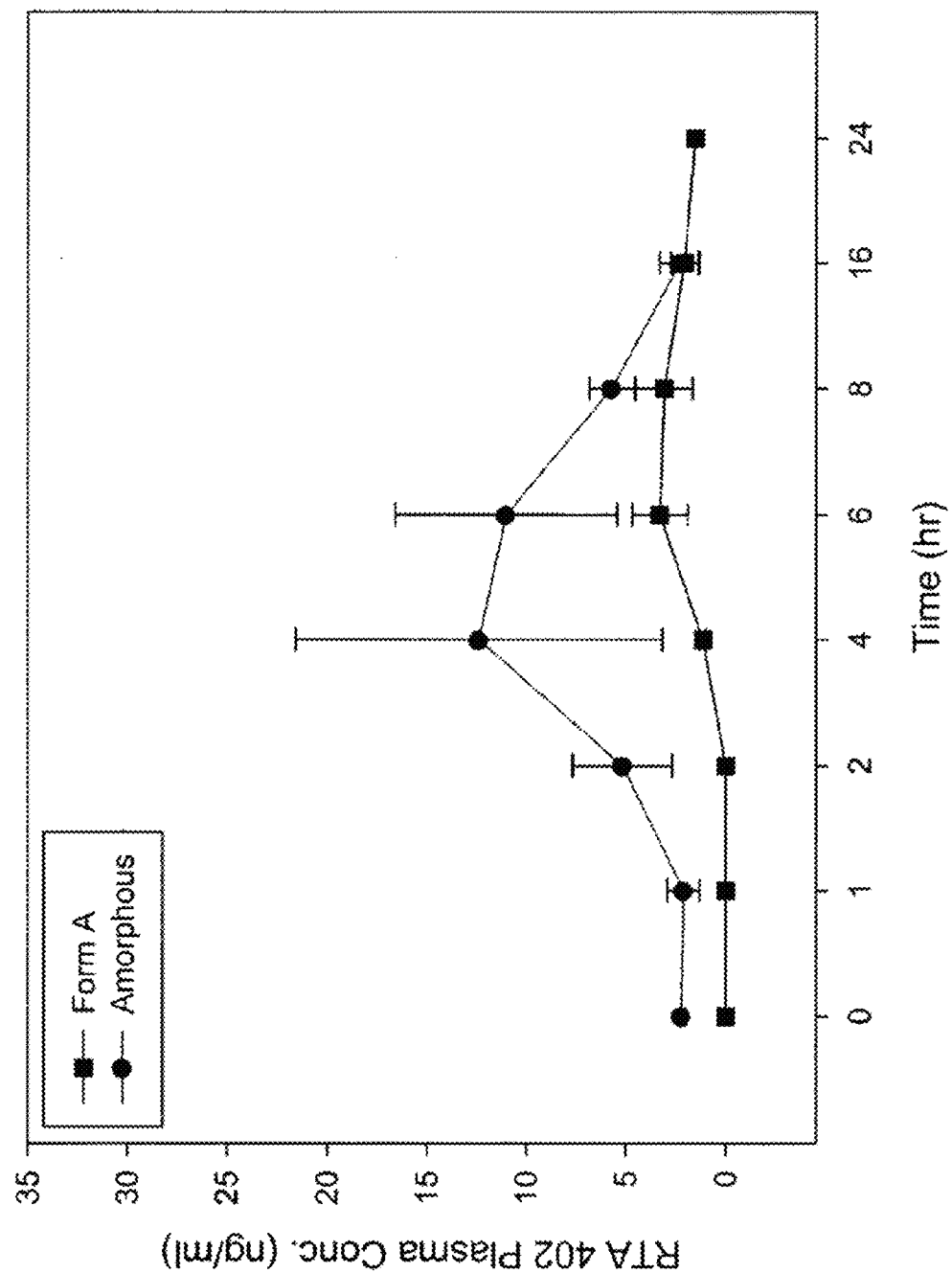
FIG. 15—Improved Bioavailability of Form B (Amorphous) in Cynomolgus Monkeys. The figure shows a representative plot of the area under the curve for Form A and Form B, following a 4.1 mg/kg oral administration to cynomolgus monkeys. Each data point represents the mean plasma concentration of CDDO methyl ester in 8 animals. Error bars represent the standard deviation within the sampled population.

Polymorphic forms of the compounds of the present invention, e.g., Forms A and B of CDDO-Me, may be used in accordance with the methods of this inventions. Form B displays a bioavailability that is surprisingly better than that of Form A (FIG. 15). Specifically the bioavailability of Form B was higher than that of Form A CDDO-Me in monkeys when the monkeys received equivalent dosages of the two forms orally, in gelatin capsules (U.S. application Ser. No. 12/191,176, filed Aug. 13, 2008).

Figure 12:
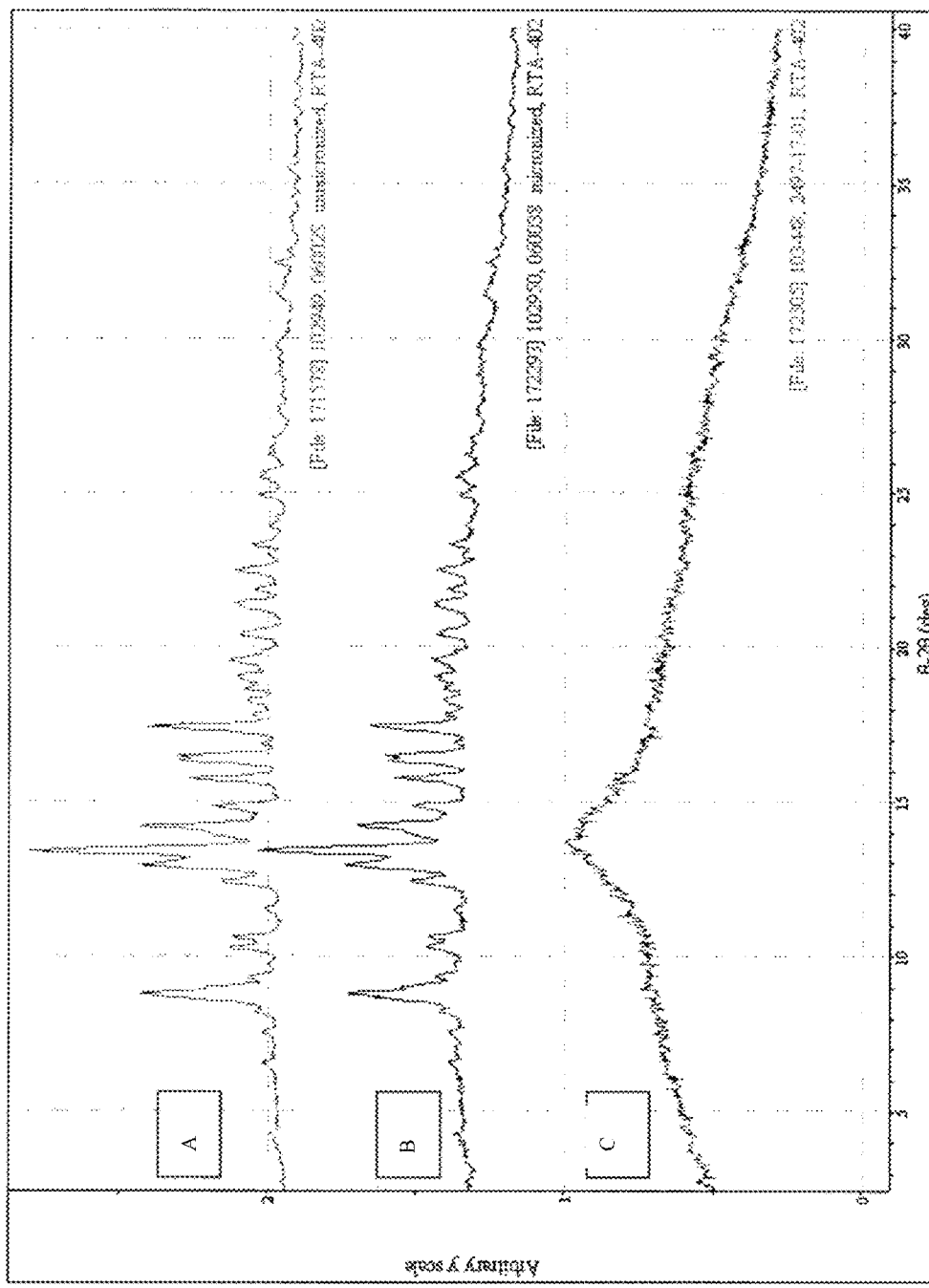
FIGS. 12A-C—X-ray Powder Diffraction (XRPD) Spectra of Forms A and B of RTA 402.

"Form A" of CDDO-Me (RTA 402) is unsolvated (non-hydrous) and can be characterized by a distinctive crystal structure, with a space group of $P4_3\,2_12$ (no. 96) unit cell dimensions of a=14.2 Å, b=14.2 Å and c=81.6 Å, and by a packing structure, whereby three molecules are packed in helical fashion down the crystallographic b axis. In some embodiments, Form A can also be characterized by X-ray powder diffraction (XRPD) pattern (CuKα) comprising significant diffraction peaks at about 8.8, 12.9, 13.4, 14.2 and 17.4°2θ. In some variations, the X-ray powder diffraction of Form A is substantially as shown in FIG. 12A or FIG. 12B.

Figure 14:
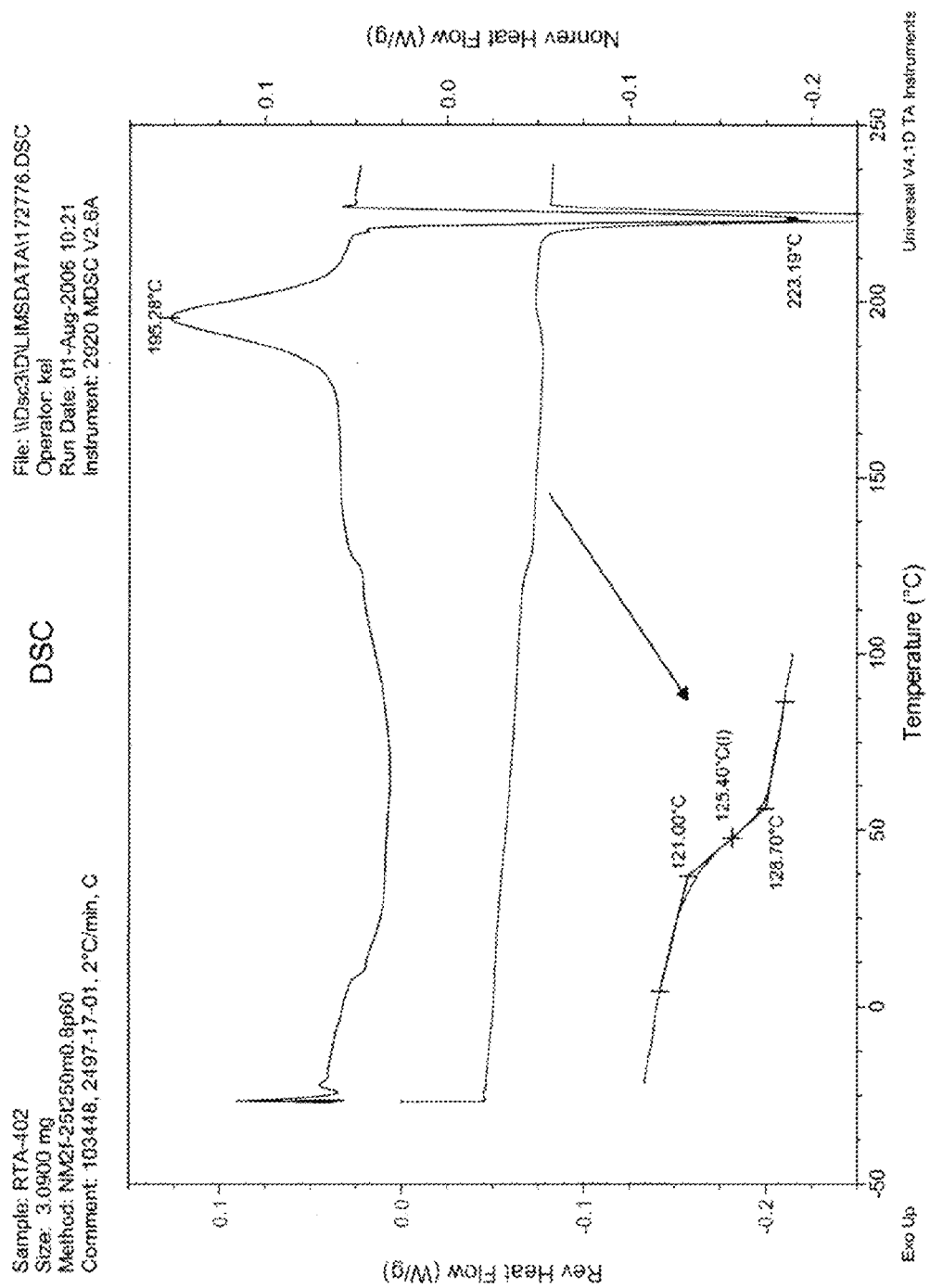
FIG. 14—Modulated Differential Scanning Calorimetry (MDSC) Curve of Form B RTA 402. The section of the curve shown in the expanded view is consistent with a glass transition temperature ($T_g$).

Unlike Form A, "Form B" of CDDO-Me is in a single phase but lacks such a defined crystal structure. Samples of Form B show no long-range molecular correlation, i.e., above roughly 20 Å. Moreover, thermal analysis of Form B samples reveals a glass transition temperature ($T_g$) in a range from about 120° C. to about 130° C. (FIG. 14). In contrast, a disordered nanocrystalline material does not display a $T_g$ but instead only a melting temperature ($T_m$), above which crystalline structure becomes a liquid. Form B is typified by an XRPD spectrum (FIG. 12C) differing from that of Form A (FIG. 12A or FIG. 12B). Since it does not have a defined crystal structure, Form B likewise lacks distinct XRPD peaks, such as those that typify Form A, and instead is characterized by a general "halo" XRPD pattern. In particular, the non-crystalline Form B falls into the category of "X-ray amorphous" solids because its XRPD pattern exhibits three or fewer primary diffraction halos. Within this category, Form B is a "glassy" material.

Form A and Form B of CDDO-Me are readily prepared from a variety of solutions of the compound. For example. Form B can be prepared by fast evaporation or slow evaporation in MTBE, THF, toluene, or ethyl acetate. Form A can be prepared in several ways, including via fast evaporation, slow evaporation, or slow cooling of a CDDO-Me solution in ethanol or methanol. Preparations of CDDO-Me in acetone can produce either Form A, using fast evaporation, or Form B, using slow evaporation.

Figure 13:
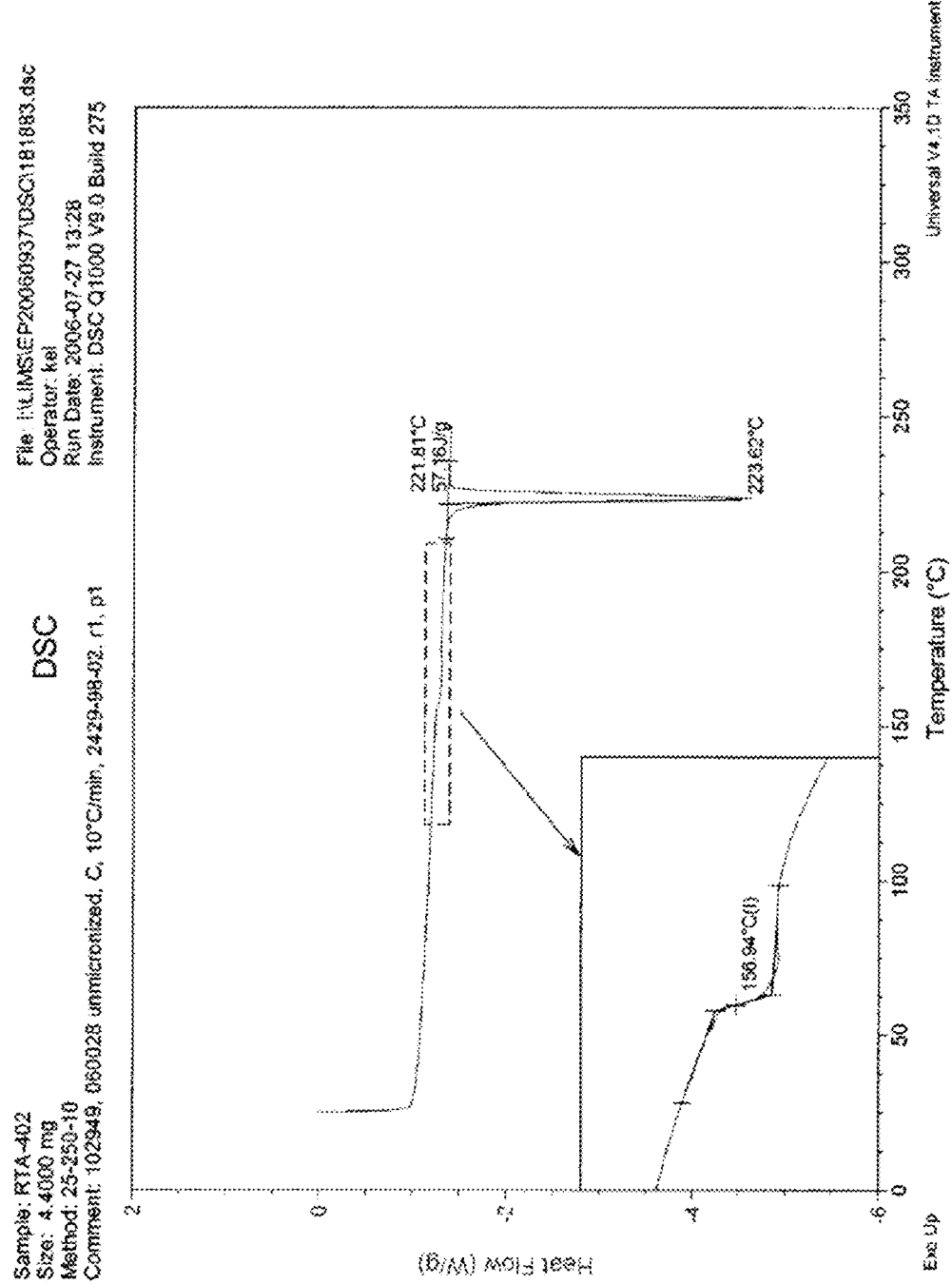
FIG. 13—Modulated Differential Scanning Calorimetry (MDSC) Curve of Form A RTA 402. The section of the curve shown in the expanded view is consistent with a glass transition temperature ($T_g$).

Various means of characterization can be used together to distinguish Form A and Form B CDDO-Me from each other and from other forms of CDDO-Me. Illustrative of the techniques suitable for this purpose are solid state Nuclear Magnetic Resonance (NMR), X-ray powder diffraction (compare FIGS. 12A & B with FIG. 12C), X-ray crystallography, Differential Scanning Calorimetry (DSC) (compare FIG. 13 with FIG. 14), dynamic vapor sorption/desorption (DVS), Karl Fischer analysis (KF), hot stage microscopy, modulated differential screening calorimetry, FT-IR, and Raman spectroscopy. In particular, analysis of the XRPD and DSC data can distinguish Form A, Form B, and a hemibenzenate forms of CDDO-Me (U.S. application Ser. No. 12/191,176, filed Aug. 13, 2008.)

Additional details regarding polymorphic forms of CDDO-Me are described in U.S. Provisional Application No. 60/955,939, filed Aug. 15, 2007, and the corresponding non-provisional U.S. application Ser. No. 12/191,176, filed Aug. 13, 2008, which are both incorporated herein by reference in their entireties.

V. Use of Triterpenoids for the Treatment of Chronic Kidney Disease, Insulin Resistance/Diabetes and Endothelial Dysfunction/Cardiovascular Disease The compounds and methods of this invention may be used for treating various aspects of renal/kidney disease, including both acute and chronic indications. In general, the method will comprise administering to the subjects pharmaceutically effective amounts of a compound of this invention.

Inflammation contributes significantly to the pathology of chronic kidney disease (CKD). There is also a strong mechanistic link between oxidative stress and renal dysfunction. The NF-κB signaling pathway plays an important role in the progression of CKD as NF-κB regulates the transcription of MCP-1, a chemokine that is responsible for the recruitment of monocytes/macrophages resulting in an inflammatory response that ultimately injures the kidney (Wardle, 2001). The Keap1/Nrf2/ARE pathway controls the transcription of several genes encoding antioxidant enzymes, including heme oxygenase-1 (HO-1). Ablation of the Nrf2 gene in female mice results in the development of lupus-like glomerular nephritis (Yoh et al., 2001; Ma et al., 2006). Furthermore, several studies have demonstrated that HO-1 expression is induced in response to renal damage and inflammation and that this enzyme and its products—bilirubin and carbon monoxide—play a protective role in the kidney (Nath et al., 2006).

The glomerulus and the surrounding Bowman's capsule constitute the basic functional unit of the kidney. Glomerular filtration rate (GFR) is the standard measure of renal function. Creatinine clearance is commonly used to measure GFR. However, the level of serum creatinine is commonly used as a surrogate measure of creatinine clearance. For instance, excessive levels of serum creatinine are generally accepted to indicate inadequate renal function and reductions in serum creatinine over time are accepted as an indication of improved renal function. Normal levels of creatinine in the blood are approximately 0.6 to 1.2 milligrams (mg) per deciliter (dl) in adult males and 0.5 to 1.1 milligrams per deciliter in adult females.

Acute kidney injury (AKI) can occur following ischemia-reperfusion, treatment with certain pharmacological agents such as cisplatin and rapamycin, and intravenous injection of radiocontrast media used in medical imaging. As in CKD, inflammation and oxidative stress contribute to the pathology of AKI. The molecular mechanisms underlying radiocontrast-induced nephropathy (RCN) are not well understood; however, it is likely that a combination of events including prolonged vasoconstriction, impaired kidney autoregulation, and direct toxicity of the contrast media all contribute to renal failure (Tumlin et al., 2006). Vasoconstriction results in decreased renal blood flow and causes ischemia-reperfusion and the production of reactive oxygen species. HO-1 is strongly induced under these conditions and has been demonstrated to prevent ischemia-reperfusion injury in several different organs, including the kidney (Nath et al., 2006). Specifically, induction of HO-1 has been shown to be protective in a rat model of RCN (Goodman et al., 2007). Reperfusion also induces an inflammatory response, in part though activation of NF-κB signaling (Nichols, 2004). Targeting NF-κB has been proposed as a therapeutic strategy to prevent organ damage (Zingarelli et al., 2003).

Without being bound by theory, the potency of the compounds of the present invention, e.g., RTA 402, is largely derived from the addition of α,β-unsaturated carbonyl groups. In in vitro assays, most activity of the compounds can be abrogated by the introduction of dithiothreitol (DTT), N-acetyl cysteine (NAC), or glutathione (GSH); thiol containing moieties that interact with α,β-unsaturated carbonyl groups (Wang et al., 2000; Ikeda et al., 2003; 2004; Shishodia et al., 2006). Biochemical assays have established that RTA 402 directly interacts with a critical cysteine residue (C179) on IKKβ (see below) and inhibits its activity (Shishodia et al., 2006; Ahmad et al., 2006). IKKβ controls activation of NF-κB through the "classical" pathway which involves phosphorylation-induced degradation of IκB resulting in release of NF-κB dimers to the nucleus. In macrophages, this pathway is responsible for the production of many pro-inflammatory molecules in response to TNFα and other pro-inflammatory stimuli.

RTA 402 also inhibits the JAK/STAT signaling pathway at multiple levels. JAK proteins are recruited to transmembrane receptors (e.g., IL-6R) upon activation by ligands such as interferons and interleukins. JAKs then phosphorylate the intracellular portion of the receptor causing recruitment of STAT transcription factors. The STATs are then phosphorylated by JAKs, form dimers, and translocate to the nucleus where they activate transcription of several genes involved in inflammation. RTA 402 inhibits constitutive and IL-6-induced STAT3 phosphorylation and dimer formation and directly binds to cysteine residues in STAT3 (C259) and in the kinase domain of JAK 1 (C1077). Biochemical assays have also established that the triterpenoids directly interact with critical cysteine residues on Keap1 (Dinkova-Kostova et al., 2005). Keap1 is an actin-tethered protein that keeps the transcription factor Nrf2 sequestered in the cytoplasm under normal conditions (Kobayashi & Yamamoto, 2005). Oxidative stress results in oxidation of the regulatory cysteine residues on Keap1 and causes the release of Nrf2. Nrf2 then translocates to the nucleus and binds to antioxidant response elements (AREs) resulting in transcriptional activation of many antioxidant and anti-inflammatory genes. Another target of the Keap1/Nrf2/ARE pathway is heme oxygenase 1 (HO-1). HO-1 breaks down heme into bilirubin and carbon monoxide and plays many antioxidant and anti-inflammatory roles (Maines & Gibbs, 2005). HO-1 has recently been shown to be potently induced by the triterpenoids (Liby et al., 2005), including RTA 402. RTA 402 and many structural analogs have also been shown to be potent inducers of the expression of other Phase 2 proteins (Yates et al., 2007).

RTA 402 is a potent inhibitor of NF-κB activation. Furthermore. RTA 402 activates the Keap1/Nrf2/ARE pathway and induces expression of HO-1. As described below, RTA 402 has demonstrated activity in two animal models of AKI. Furthermore, reduced serum creatinine levels and improvement of glomerular filtration have been observed in the majority of human patients that have been treated with RTA 402 (see Examples below). Significant improvements have now been observed in a Phase II study of patients with diabetic nephropathy. The findings indicate that RTA 402 may be used to improve renal function in patients with diabetic nephropathy through suppression of renal inflammation and improvement of glomerular filtration.

As noted above, both diabetes and essential hypertension are major risk factors for the development of chronic kidney disease and, ultimately, renal failure. Both of these conditions, along with indicators of systemic cardiovascular disease such as hyperlipidemia, are frequently present in the same patient, especially if that patient is clinically obese. Although the unifying factors are not completely understood, dysfunction of the vascular endothelium has been implicated as a significant pathological factor in systemic cardiovascular disease, chronic kidney disease, and diabetes (see, e.g., Zoccali, 2006). Acute or chronic oxidative stress in vascular endothelial cells has been implicated in the development of endothelial dysfunction, and is strongly associated with chronic inflammatory processes. Therefore, an agent capable of relieving oxidative stress and concomitant inflammation in the vascular endothelium may alleviate dysfunction and restore endothelial homeostasis. Without being bound by theory, compounds of the invention, by stimulating Nrf2-regulated endogenous antioxidant mechanisms, have shown the highly unusual ability to improve parameters related to renal function (e.g., serum creatinine and estimated glomerular filtration rate), glycemic control and insulin resistance (e.g., hemoglobin A1c), and systemic cardiovascular disease (e.g., circulating endothelial cells) in patients having abnormal clinical values for these parameters. Currently, combination therapy is typically required in such patients to achieve improvements in measures of glycemic control and cardiovascular disease, including the use of angiotensin-converting enzyme inhibitors or angiotensin II receptor blockers to alleviate hypertension and slow the progression of chronic kidney disease. By achieving simultaneous and clinically meaningful improvements in all of these parameters, especially measures of renal function, compounds of the invention represent a significant improvement over currently available therapies. In some aspects, the compounds of the present invention may be used to treat a combination of the above conditions as a single therapy, or in combination with fewer additional therapies than would currently be used.

These findings also indicate that administration of RTA 402 may be used to protect patients from kidney damage such as from exposure to radiocontrast agents, as in the case of radiocontrast-induced nephropathy (RCN), as well as in other contexts. In one aspect, the compounds of this invention may be used to treat ischemia-reperfusion- and/or chemotherapy-induced acute renal injury. For example, the results shown in Examples 2 and 3 below demonstrate that RTA 402 is protective in animal models of ischemia-reperfusion- and chemotherapy-induced acute renal injury.

Serum creatinine has been measured in several animal models treated with RTA 402. Significant reductions of serum creatinine levels relative to baseline levels or levels in control animals have been observed in cynomolgus monkeys, beagle dogs, and Sprague-Dawley rats (FIGS. 3A-D). This effect has been observed in rats with both forms of RTA 402 (crystalline and amorphous).

RTA 402 reduces serum creatinine in patients. For example, improvements were observed in cancer patients receiving RTA 402. In humans, nephrotoxicity is a dose-limiting side-effect of treatment with cisplatin. Cisplatin-induced damage to the proximal tubules is thought to be mediated by increased inflammation, oxidative stress, and apoptosis (Yao et al., 2007). Serum creatinine has also been measured in patients with chronic kidney disease (CKD) enrolled in an open label Phase II clinical trial of RTA 402 (Example 6). This study was designed with multiple endpoints, in categories of insulin resistance, endothelial dysfunction/CVD, and CKD, including measurements of hemoglobin A1c (A1c), a widely used phase 3 endpoint for glycemic control.

A1c is a minor component of hemoglobin to which glucose is bound. A1c also is referred to as glycosylated or glucosylated hemoglobin. A1c may be separated by charge and size from the other hemoglobin A components in blood using high performance liquid chromatography (HPLC). Because A1c is not affected by short-term fluctuations in blood glucose concentrations, for example, due to meals, blood can be drawn for A1c testing without regard to when food was eaten. In healthy, non-diabetic patients the A1c level is less than 7% of total hemoglobin. The normal range is 4-5.9%. In poorly controlled diabetes, it can be 8.0% or above. It has been demonstrated that the complications of diabetes can be delayed or prevented if the A1c level can be kept close to 7%.

Recently approved agents typically only reduce A1c levels an amount of 0.4 to 0.80 over six months of treatment, with 28 day improvements typically smaller. The table below shows six-month Hemoglobin A1c Reductions by two approved agents, sitagliptin and pramlintide acetate (Aschner et al., 2006; Goldstein et al., 2007; Pullman et al., 2006).

| Drug | Duration of DM (years) | Study Design | Mean A1c | Change |
|---|---|---|---|---|
| Sitagliptin | 4.3 | +/− placebo with A1c ≥7.0 | 8.0 | −0.8 |
| | 4.4 | +/− metformin with A1c ≥7.5 | 8.9 | −0.7 |
| | 6.1 | pioglitazone +/− sitagliptin; A1c ≥7.0 | 8.1 | −0.7 |
| Pramlintide acetate | 13 | +/− insulin | 9.1 | −0.4 |

In comparison, RTA 402 reduces A1c in 28 days in refractory diabetics on top of standard of care. The treatment showed an intent-to-treat reduction of 0.34 (n=21) and an elevated baseline (≥7.0 at baseline) reduction of 0.50 (n=16). These results are presented in greater detail in the Examples section below. See also FIGS. 6 and 7.

In another aspect, the compounds of this invention may also be used to improve insulin sensitivity and/or glycemic control. For example, hyperinsulinemic euglycemic clamp test results in the study detailed in Example 6 showed that treatment with RTA 402 improved glycemic control. The hyperinsulinemic euglycemic clamp test is a standard method for investigating and quantifying insulin sensitivity. It measures the amount of glucose necessary to compensate for an increased insulin level without causing hypoglycemia (DeFronzo et al., 1979).

The typical procedure is as follows: Through a peripheral vein, insulin is infused at 10-120 mU per $m^2$ per minute. In order to compensate for the insulin infusion, glucose 20% is infused to maintain blood sugar levels between 5 and 5.5 mmol/liter. The rate of glucose infusion is determined by checking the blood sugar levels every 5 to 10 minutes.

Typically, low-dose insulin infusions are more useful for assessing the response of the liver, whereas high-dose insulin infusions are useful for assessing peripheral (i.e., muscle and fat) insulin action.

Results are typically evaluated as follows: The rate of glucose infusion during the last 30 minutes of the test determines insulin sensitivity. If high levels (7.5 mg/min or higher) are required, the patient is insulin-sensitive. Very low levels (4.0 mg/min or lower) indicate that the body is resistant to insulin action. Levels between 4.0 and 7.5 mg/min may not be definitive and may suggest "impaired glucose tolerance," an early sign of insulin resistance.

Figure 9:
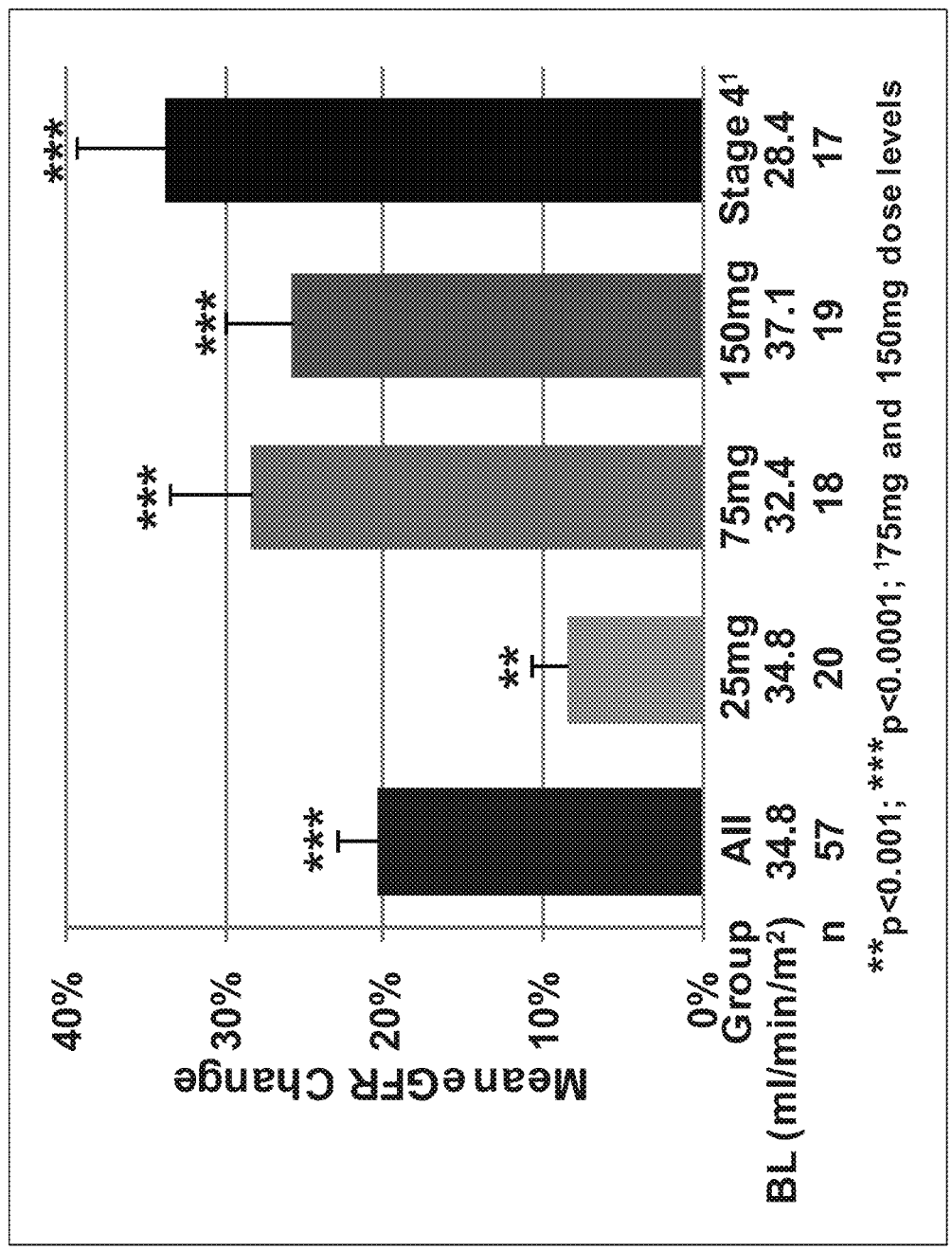
FIG. 9—Reversible Dose Dependent GFR Increase in 28 Days. Treatment with RTA 402 increases GFR dose-dependently. All evaluable patients were included. An improvement of >30% was noted in patients with Stage 4 renal disease.

The methods of this invention may be used to improve renal function. As shown in Example 6, treatment using RTA 402 has been shown to improve six measures of renal function and status, including serum creatinine based eGFR, creatinine clearance, BUN, Cystatin C, Adiponectin, and Angiotensin II. RTA 402 was shown to increase GFR in a dose-dependent manner and with high response rate (86%; n=22). As also shown in FIG. 9, the 28 day GFR improvements were reversible after the drug was withdrawn.

In some embodiments, treatment methods of this invention result in improved levels of Adiponectin and/or Angiotensin II. Adiponectin and Angiotensin II are typically elevated in DN patients and correlate with renal disease severity. Adiponectin (also referred to as Acrp30, apM1) is a hormone known to modulate a number of metabolic processes, including glucose regulation and fatty acid catabolism. Adiponectin is secreted from adipose tissue into the bloodstream and is abundant in plasma relative to many other hormones. Levels of the hormone are inversely correlated with body fat percentage in adults, while the association in infants and young children is more unclear. The hormone plays a role in the suppression of the metabolic derangements that may result in type 2 diabetes, obesity, atherosclerosis and non-alcoholic fatty liver disease (NAFLD). Adiponectin can be used to predict all-cause mortality and end stage renal disease in DN patients.

The compounds and methods of this invention may be used for treating various aspects of cardiovascular disease (CVD). The treatment methods of this invention have been found to reduce circulating endothelial cells (CECs) in human patients. CECs are markers of endothelial dysfunction and vascular injury. Endothelial dysfunction is a systemic inflammatory process that is linked to cardiovascular and end-organ damage. Elevated CECs typically correlate with the development, progression, and death from CVD. They also typically correlate with chronic kidney disease and decreased GFR. Historical normal levels are ≤5 cells/mL.

Typical features of endothelial dysfunction include the inability of arteries and arterioles to dilate fully in response to an appropriate stimulus. This creates a detectable difference in subjects with endothelial dysfunction versus a normal, healthy endothelium. Such a difference can be tested by a variety of methods including iontophoresis of acetylcholine, intra-arterial administration of various vasoactive agents, localised heating of the skin or temporary arterial occlusion by inflating a blood pressure cuff to high pressures. Testing can also take place in the coronary arteries themselves. These techniques are thought to stimulate the endothelium to release nitric oxide (NO) and possibly some other agents, which diffuse into the surrounding vascular smooth muscle causing vasodilation.

For example, according to the Phase II study results (Example 6), patients treated with RTA 402 for 28 days showed a reduction in cardiovascular inflammatory markers in the form of a reduction in the number of circulating endothelial cells. The reduction in CECs for the intent-to-treat group (n=20) was 27%; the reduction for the elevated baseline group (n=14) was 40% (p=0.02) and nine of those patients showed a normal level for CECs post-treatment. These results are consistent with a reversal of endothelial dysfunction.

The treatment methods of this invention have been found to reduce matrix metallopeptidase 9 (MMP-9), soluble adhesion molecules and tumor necrosis factor (TNFα) in most patients. High levels of these typically correlate with poor cardiovascular outcomes.

VI. Pharmaceutical Formulations and Routes of Administration

Administration of the compounds of the present invention to a patient will follow general protocols for the administration of pharmaceuticals, taking into account the toxicity, if any, of the drug. It is expected that the treatment cycles would be repeated as necessary.

The compounds of the present invention may be administered by a variety of methods, e.g., orally or by injection (e.g. subcutaneous, intravenous, intraperitoneal, etc.). Depending on the route of administration, the active compounds may be coated by a material to protect the compound from the action of acids and other natural conditions which may inactivate the compound. They may also be administered by continuous perfusion/infusion of a disease or wound site. Specific examples of formulations, including a polymer-based dispersion of CDDO-Me that showed improved oral bioavailability, are provided in U.S. application Ser. No. 12/191,176, filed Aug. 13, 2008, which is incorporated herein by reference in its entirety. It will be recognized by those skilled in the art that other methods of manufacture may be used to produce dispersions of the present invention with equivalent properties and utility (see Repka et al., 2002 and references cited therein). Such alternative methods include but are not limited to solvent evaporation, extrusion, such as hot melt extrusion, and other techniques.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions may be prepared in, e.g., glycerol, liquid polyethylene glycols, mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The actual dosage amount of a compound of the present invention or composition comprising a compound of the present invention administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the pharmaceutically effective amount is a daily dose from about 0.1 mg to about 500 mg of the compound. In some variations, the daily dose is from about 1 mg to about 300 mg of the compound. In some variations, the daily dose is from about 10 mg to about 200 mg of the compound. In some variations, the daily dose is about 25 mg of the compound. In other variations, the daily dose is about 75 mg of the compound. In still other variations, the daily dose is about 150 mg of the compound. In further variations, the daily dose is from about 0.1 mg to about 30 mg of the compound. In some variations, the daily dose is from about 0.5 mg to about 20 mg of the compound. In some variations, the daily dose is from about 1 mg to about 15 mg of the compound. In some variations, the daily dose is from about 1 mg to about 10 mg of the compound. In some variations, the daily dose is from about 1 mg to about 5 mg of the compound.

In some embodiments, the pharmaceutically effective amount is a daily dose is 0.01-25 mg of compound per kg of body weight. In some variations, the daily dose is 0.05-20 mg of compound per kg of body weight. In some variations, the daily dose is 0.1-10 mg of compound per kg of body weight. In some variations, the daily dose is 0.1-5 mg of compound per kg of body weight. In some variations, the daily dose is 0.1-2.5 mg of compound per kg of body weight.

In some embodiments, the pharmaceutically effective amount is a daily dose is of 0.1-1000 mg of compound per kg of body weight. In some variations, the daily dose is 0.15-20 mg of compound per kg of body weight. In some variations, the daily dose is 0.20-10 mg of compound per kg of body weight. In some variations, the daily dose is 0.40-3 mg of compound per kg of body weight. In some variations, the daily dose is 0.50-9 mg of compound per kg of body weight. In some variations, the daily dose is 0.60-8 mg of compound per kg of body weight. In some variations, the daily dose is 0.70-7 mg of compound per kg of body weight. In some variations, the daily dose is 0.80-6 mg of compound per kg of body weight. In some variations, the daily dose is 0.90-5 mg of compound per kg of body weight. In some variations, the daily dose is from about 1 mg to about 5 mg of compound per kg of body weight.

An effective amount typically will vary from about 0.001 mg/kg to about 1,000 mg/kg, from about 0.01 mg/kg to about 750 mg/kg, from about 0.1 mg/kg to about 500 mg/kg, from about 0.2 mg/kg to about 250 mg/kg, from about 0.3 mg/kg to about 150 mg/kg, from about 0.3 mg/kg to about 100 mg/kg, from about 0.4 mg/kg to about 75 mg/kg, from about 0.5 mg/kg to about 50 mg/kg, from about 0.6 mg/kg to about 30 mg/kg, from about 0.7 mg/kg to about 25 mg/kg, from about 0.8 mg/kg to about 15 mg/kg, from about 0.9 mg/kg to about 10 mg/kg, from about 1 mg/kg to about 5 mg/kg, from about 100 mg/kg to about 500 mg/kg, from about 1.0 mg/kg to about 250 mg/kg, or from about 10.0 mg/kg to about 150 mg/kg, in one or more dose administrations daily, for one or several days (depending, of course, of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range, for example, of 750 mg to 9,000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day, less than 10 mg/kg/day, or less than 5 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is within ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 1 mg/kg/body weight to about 5 mg/kg/body weight, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present invention may comprise, for example, at least about 0.1% of a compound of the present invention. In other embodiments, the compound of the present invention may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

Non-limiting specific formulations include CDDO-Me polymer dispersions (see U.S. application Ser. No. 12/191,176, filed Aug. 13, 2008, which is incorporated herein by reference). Some of the formulations reported therein exhibited higher bioavailability than either the micronized Form A or nanocrystalline Form A formulations. Additionally, the polymer dispersion based formulations demonstrated further surprising improvements in oral bioavailability relative to the micronized Form B formulations. For example, the methacrylic acid copolymer, Type C and HPMC-P formulations showed the greatest bioavailability in the subject monkeys.

VII. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Various combinations may be employed, such as when a compound of the present invention is "A" and "B" represents a secondary agent, non-limiting examples of which

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | | A/B/A/B | A/B/B/A | | B/B/A/A |
| B/A/B/A | B/A/A/B | A/A/A/B | | B/A/A/A | A/B/A/A | | A/A/B/A |

It is contemplated that other anti-inflammatory agents may be used in conjunction with the treatments of the current invention. For example, other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. See also U.S. Pat. No. 6,025,395, which is incorporated herein by reference.

Dietary and nutritional supplements with reported benefits for treatment or prevention of Parkinson's, Alzheimer's, multiple sclerosis, amyotrophic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the compounds of the current invention.

Other particular secondary therapies include immunosuppressants (for transplants and autoimmune-related RKD), anti-hypertensive drugs (for high blood pressure-related RKD, e.g., angiotensin-converting enzyme inhibitors and angiotensin receptor blockers), insulin (for diabetic RKD), lipid/cholesterol-lowering agents (e.g., HMG-CoA reductase inhibitors such as atorvastatin or simvastatin), treatments for hyperphosphatemia or hyperparathyroidism associated with CKD (e.g., sevelamer acetate, cinacalcet), dialysis, and dietary restrictions (e.g., protein, salt, fluid, potassium, phosphorus).

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Chemicals. Triterpenoids were synthesized as previously described in Honda et al. (1998), Honda et al. (2000b), Honda et al. (2002) and Yates et al. (2007), which are all incorporated herein by reference.

Example 2

Mouse Ischemia—Reperfusion Results

In a mouse model of ischemic acute renal failure, the renal artery is clamped for approximately twenty minutes. After this time, the clamp is removed and the kidney is reperfused with blood. Ischemia-reperfusion results in renal damage and decreased renal function which can be assessed by blood urea nitrogen (BUN) levels, which become elevated following renal damage. As shown in FIGS. 1a-d, surgically-induced ischemia-reperfusion increased BUN levels by approximately 2-fold. However, in animals treated with 2 mg/kg RTA 402 orally once daily beginning two days prior to the surgery, the BUN levels were significantly reduced ($p<0.01$) relative to vehicle-treated animals and were similar to the levels in animals that underwent sham surgeries (FIGS. 1a-c). Histological measures of kidney damage and inflammation were also significantly improved by treatment with RTA 402 (FIG. 1d). These data indicate that RTA 402 is protective against ischemia-reperfusion induced tissue damage.

Example 3

Rat Chemotherapy-Induced Acute Renal Injury Results

Figure 2:
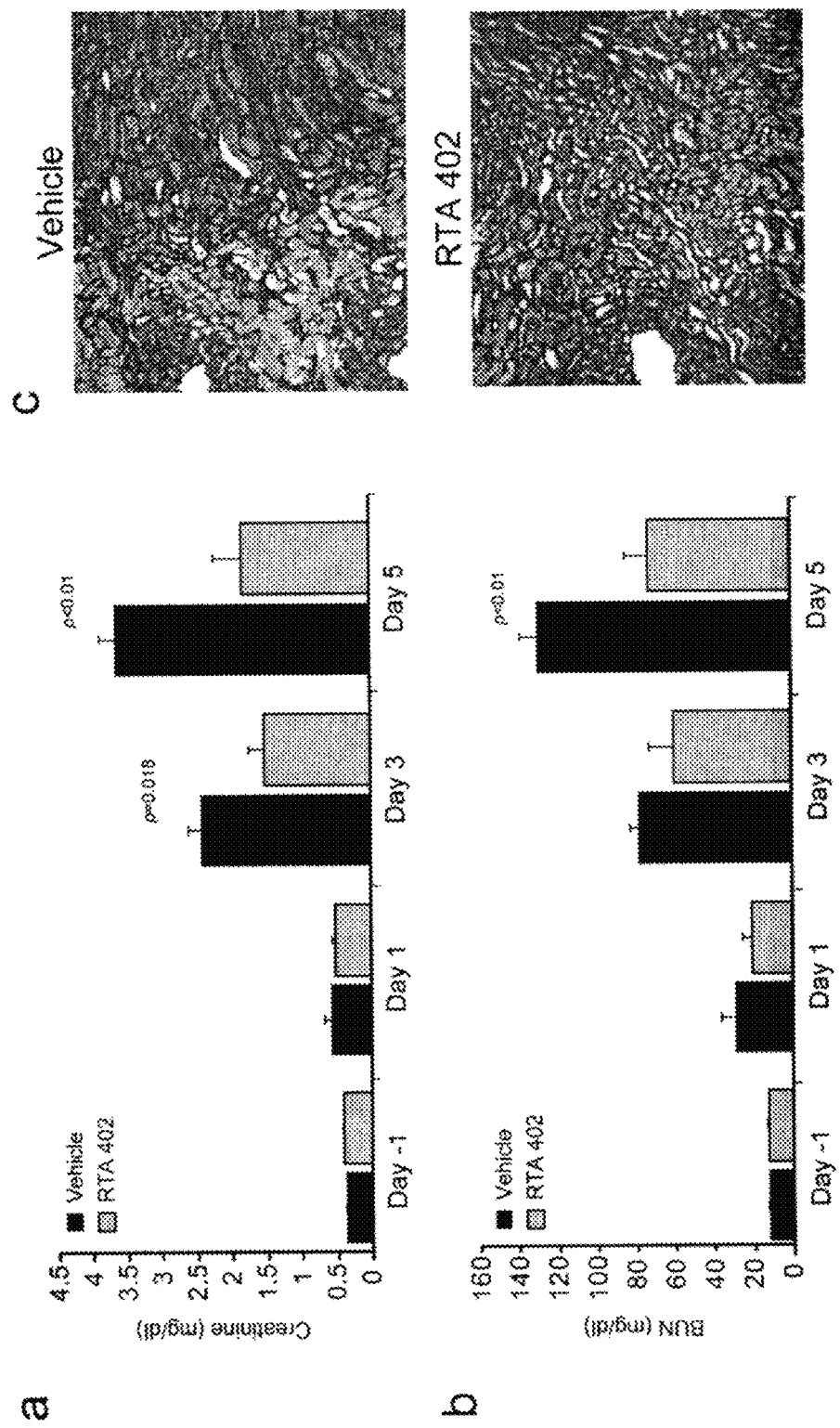
FIGS. 2a-c—RTA 402 reduces cisplatin-induced renal toxicity. Rats were administered RTA 402 at 10 mg/kg or simply the vehicle (sesame oil) every day by oral gavage beginning on Day −1. On Day 0, the rats received an intravenous injection of cisplatin at 6 mg/kg. Blood samples were drawn on the indicated days and the levels of creatinine (FIG. 2a) and blood urea nitrogen (BUN) (FIG. 2b) were measured as markers of renal damage. A statistically significant difference was observed between the vehicle-treated and RTA 402-treated groups on Day 3 (creatinine) and Day 5 (creatinine and BUN).
Figure 3:
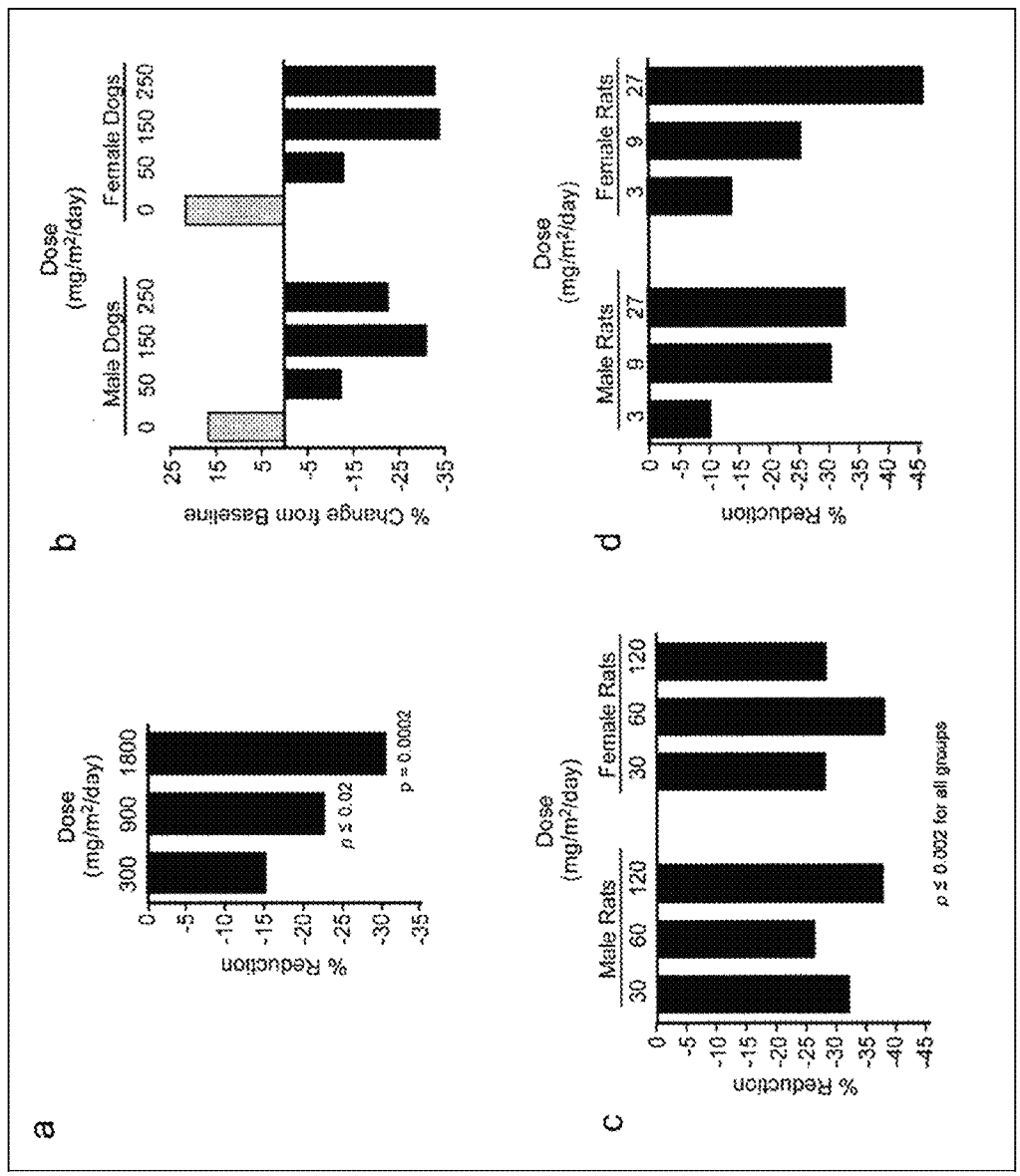
FIGS. 3a-d—RTA 402 reduces serum creatinine levels in monkeys, dogs, and rats.

In another model of acute renal injury, rats were injected intravenously with the antineoplastic agent cisplatin. In humans, nephrotoxicity is a dose-limiting side effect of treatment with cisplatin. Cisplatin-induced damage to the proximal tubules is thought to be mediated by increased inflammation, oxidative stress, and apoptosis (Yao et al., 2007). Rats treated with a single dose of cisplatin at 6 mg/kg developed renal insufficiency as measured by increased blood levels of creatinine and BUN. Treatment with 10 mg/kg RTA 402 by oral gavage beginning one day prior to treatment with cisplatin and continuing every day significantly reduced blood levels of creatinine and BUN (FIGS. 2a-b). Histological evaluation of the kidneys demonstrated an improvement in the extent of proximal tubule damage in RTA 402-treated animals compared to vehicle-treated animals (FIG. 2c).

Example 4

Reduction of Serum Creatinine Levels in Several Species

Serum creatinine has been measured in several animal species treated with RTA 402 in the course of toxicology studies. Significant reductions of serum creatinine levels relative to baseline levels or levels in control animals have been observed in cynomolgus monkeys, beagle dogs, and Sprague-Dawley rats (FIGS. 3a-d). This effect has been observed in rats with crystalline and amorphous forms of RTA 402.

Example 5

Reduced Serum Creatinine and Increased eGFR in Cancer Patients

Figure 4:
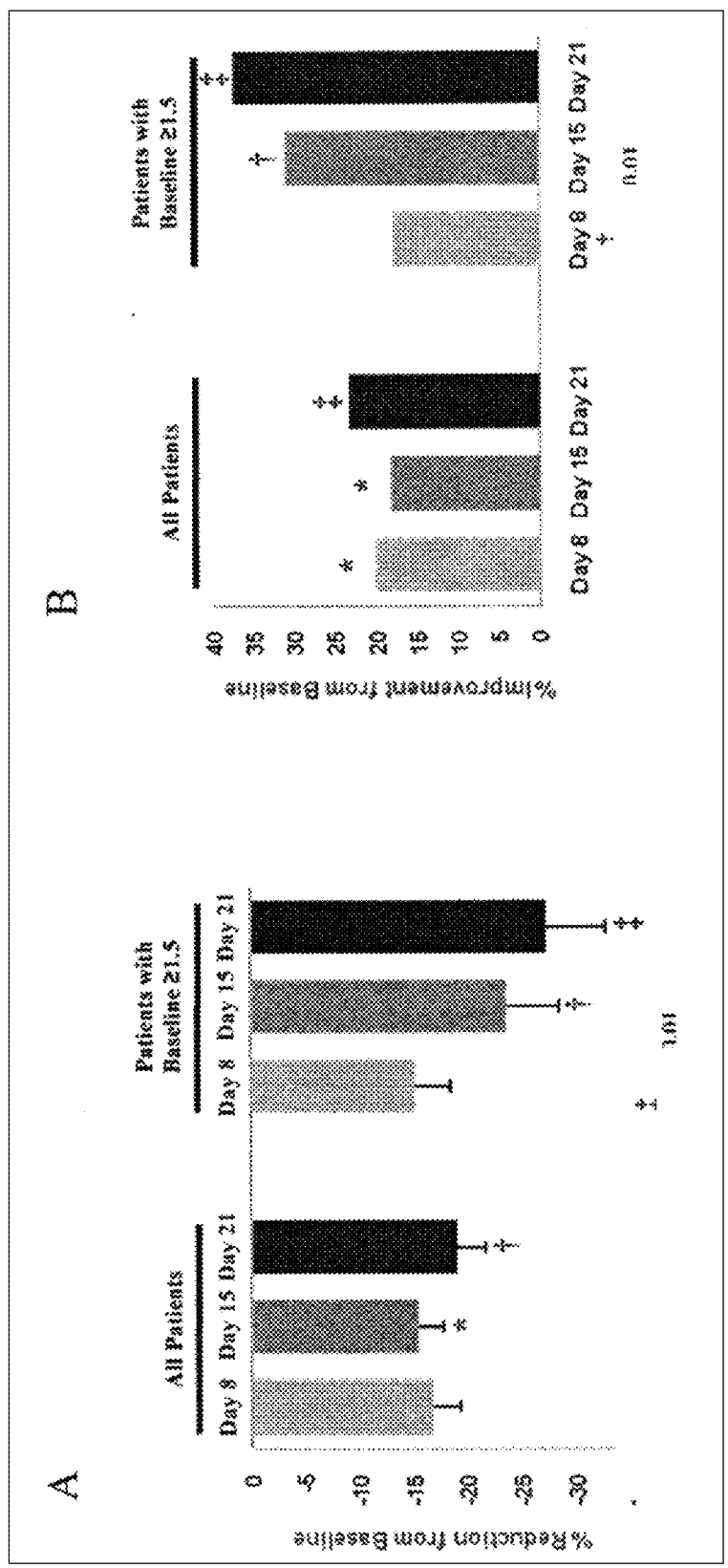
FIGS. 4A-B—RTA 402 reduces serum creatinine levels and increases the estimated glomerular filtration rate (eGFR) in human patients with cancer.

Serum creatinine has also been measured in patients with cancer enrolled in a Phase I clinical trial of RTA 402. These patients received RTA 402 once daily at doses from 5 to 1,300 mg/day for a total of twenty-one days every 28 days. A reduction in serum creatinine by greater than 15% was observed as early as eight days following treatment initiation and persisted through the end of the cycle (FIG. 4A). This reduction was maintained in those patients that received six or more cycles of treatment with RTA 402. A subset of patients with pre-existing renal damage (baseline serum creatinine levels of at least 1.5 mg/dl) also had significant reductions in serum creatinine levels following treatment with RTA 402. In these patients, serum creatinine levels decreased progressively throughout the cycle such that the Day 21 levels were approximately 25% lower than baseline levels (FIG. 4A). These results can be summarized as shown in the table below.

|  | All patients | Sub-set with elevated baseline serum creatinine levels |
| --- | --- | --- |
| Number of patients who received drug for at least 3 weeks | 45 | 8 |
| % of Patients with Decrease on Day 21 | 87% | 100% |
| % Serum Creatinine Decrease from Baseline | −18.3% | −24.5% |
| p-value (Baseline versus Day 21) | 0.001 | 0.0007 |

The estimated glomerular filtration rate (eGFR) significantly improved in the patients treated with RTA 402 (FIG. 4B).

Figure 5:
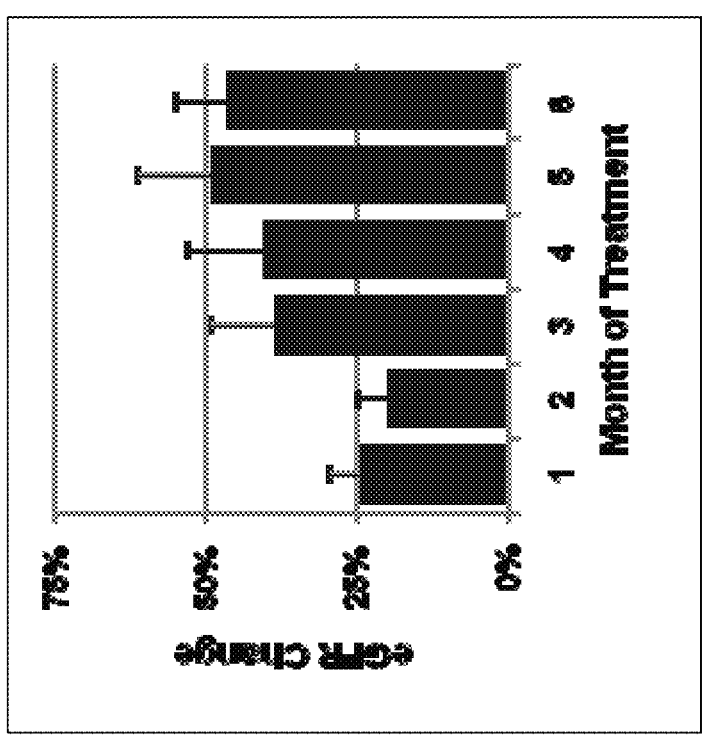
FIG. 5—RTA 402 increases GFR in human patients with cancer. Estimated glomerular filtration rate (eGFR) was measured in RTA 402-treated patients enrolled in a multi-month clinical trial for the treatment of cancer. All patients (n=11) dosed through six months were included in the analysis. The dosing information for these patients is provided in Example 5, below.

FIG. 5 shows the results following at least six months of RTA 402 treatment in eleven cancer patients, showing that eGFR improved in an approximately continuous manner. Some of these patients were enrolled in the Phase I study, whereas others were enrolled in a study of RTA 402 (in combination with gemcitabine) in patients with pancreatic cancer. The results can be summarized as shown in Table 2, below.

Example 6

Phase 2 Study in Patients with Diabetic Nephropathy

Serum creatinine has also been measured in patients with chronic kidney disease (CKD) enrolled in an open label Phase II clinical trial of RTA 402. These patients received RTA 402 once daily at three dose levels, 25 mg, 75 mg and 150 mg, for a total of 28 days.

The study was designed with multiple endpoints, in categories of insulin resistance, endothelial dysfunction/CVD, and CKD. These can be summarized as follows:

| Insulin Resistance/Diabetes | Endothelial Dysfunction/Cardiovascular | Chronic Kidney Disease |
| --- | --- | --- |
| Hgb A1c | CECs | GFR |
| GDR/ | C-Reactive Protein (CRP) | Serum Creatinine |
| Euglycemic Clamp Glucose | E-Selectin | Creatinine Clearance |
|  | VCAM | Cystatin C |
|  | Cytokines | Adiponectin |
|  |  | Angiotensin II |

A primary outcome measure for this study is determining the effects of RTA 402 administered orally at the three dose strengths on the glomerular filtration rate (as estimated by the MDRD formula) in patients with diabetic nephropathy.

Secondary outcome measures include: (1) an evaluation of the safety and tolerability of oral RTA 402 administered orally at the three different doses, in this patient population; (2) an evaluation of the effects of RTA 402 administered orally at the three dose strengths on the serum creatinine level, creatinine clearance, and urine albumin/creatinine ratio in patients with diabetic nephropathy; (3) an evaluation of the effects of RTA 402 administered orally at the three dose strengths on hemoglobin A c in all patients enrolled and on insulin response by the hyperinsulinemic euglycemic clamp test in patients enrolled at only one of the study centers; (4) an evaluation of the effects of RTA 402 at the three different doses on a panel of markers of inflammation, renal injury, oxidative stress, and endothelial cell dysfunction.

The patient population selected for this study all had type 2 diabetes with CKD. Most had been diagnosed with poor glycemic control for two decades. CKD was established through elevated serum creatinine (SCr) levels. Most of the patients had been diagnosed with cardiovascular disease (CVD) and most were receiving standard of care (SOC) treatment for diabetes, CKD and CVD, (e.g., insulin, ACEI/

TABLE 2 eGFR in Patients Receiving RTA 402 for 6 Cycles.

|  |  | Solid Tumor Study |  |  |  |  |  |  | Pancreatic Study |  |  |  |
| --- | --- | --- | --- | --- | --- | --- | --- | --- | --- | --- | --- | --- |
|  | Pt ID: | 402 | 406 | 408 | 409 | 410 | 421 | 427 | 1001 | 1104 | 1105 | 1106 |
|  | Dose (mg): | 5 | 80 | 150 | 150/300 | 300/600 | 1,300/900 | 1,300 | 150 | 300/150 | 300 | 300 |
| Cycle | BL | 109.7 | 94.2 | 73.2 | 48.4 | 49.9 | 52.5 | 70.1 | 68.8 | 67.3 | 82.4 | 89.0 |
| each cycle | 1 | 109.7 | 125.9 | 82.1 | 62.6 | 69.6 | 58.6 | 101.3 | 78.9 | 95.7 | 106.6 | 106.3 |
| is 28 days) | 2 | 109.7 | 107.9 | 77.4 | 62.6 | 63.4 | 66.2 | 78.3 | 109.9 | 71.6 | 89.3 | 106.3 |
|  | 3 | 95.7 | 107.9 | 69.4 | 62.6 | 63.4 | 75.8 | 88.4 | 135.7 | 141.2 | 106.6 | 106.3 |
|  | 4 | 95.7 | 125.9 | 77.4 | 57.0 | 69.6 | N/A | 101.3 | 175.5 | 95.7 | 106.6 | 131.2 |
|  | 5 | 109.7 | 107.9 | 77.4 | 69.2 | 63.4 | 88.4 | 101.3 | 175.5 | 114.4 | 131.6 | 131.2 |
|  | 6 | 95.7 | 125.9 | 87.4 | 69.2 | 69.6 | 75.8 | 101.3 | 135.7 | 114.4 | 170.3 | 131.2 |

ARB, β-blocker, diuretic, and statin). The baseline demographic can be summarized as follows:

| | |
|---|---|
| Age | 59 |
| Diabetes Duration (yrs) | 15.4 |
| Diabetic Nephropathy | 100% |
| Non-renal Diabetic Complications[1] | 100% |
| Hypertensive | 100% |
| Hgb A1c(%) | 7.9% |
| Failed Oral Antihyperglycemics | 90% |
| ACEI/ARB Use | 80% |
| Statin Use | 50% |

[1]Includes neuropathy and retinopathy
All values represent the mean;
n = 10;
1st 10 patients to complete study The patient inclusion criteria were as follows: (1) diagnosis of type 2 diabetes; (2) serum creatinine in women 1.3-3.0 mg/dL (115-265 μmol/L), inclusive, and in men 1.5-3.0 mg/dL (133-265 μmol/L), inclusive; (3) patient must agree to practice effective contraception; (4) patient must have a negative urine pregnancy test within 72 hours prior to the first dose of study medication; (5) patient is willing and able to cooperate with all aspects of the protocol and is able to communicate effectively; (6) patient is willing and able to provide written informed consent to participate in this clinical study.

The patient exclusion criteria were the following: (1) patients having type 1 (insulin-dependent; juvenile onset) diabetes; (2) patients with known non-diabetic renal disease (nephrosclerosis superimposed on diabetic nephropathy acceptable), or with renal allograft; (3) patients having cardiovascular disease as follows: unstable angina pectoris within 3 months of study entry; myocardial infarction, coronary artery bypass graft surgery, or percutaneous transluminal coronary angioplasty/stent within 3 months of study entry; transient ischemic attack within 3 months of study entry; cerebrovascular accident within 3 months of study entry, obstructive valvular heart disease or hypertrophic cardiomyopathy; second or third degree atrioventricular block not successfully treated with a pacemaker; (4) patients with need for chronic (>2 weeks) immunosuppressive therapy, including corticosteroids (excluding inhaled or nasal steroids) within 3 months of study entry, (5) patients with evidence of hepatic dysfunction including total bilirubin >1.5 mg/dL (>26 micromole/L) or liver transaminase (aspartate aminotransferase [AST] or alanine transferase [ALT])>1.5 times upper limit of normal; (6) if female, patient is pregnant, nursing or planning a pregnancy; (7) patients with any concurrent clinical conditions that in the judgment of the investigator could either potentially pose a health risk to the patient while involved in the study or could potentially influence the study outcome; (8) patients having known hypersensitivity to any component of the study drug; (9) patients having known allergy to iodine; (10) patients having undergone diagnostic or intervention procedure requiring a contrast agent within the last 30 days prior to entry into the study; (11) patients with change or dose-adjustment in any of the following medications: ACE inhibitors, angiotensin II blockers, non-steroidal anti inflammatory drugs (NSAIDs), or COX-2 inhibitors within 3 months; other anti-hypertensive, and other anti-diabetic medications within 6 weeks prior to entry into the study; (12) patients having a history of drug or alcohol abuse or having positive test results for any drug of abuse (positive urine drug test and/or alcohol breathalyzer test); (13) patients having participated in another clinical study involving investigational or marketed products within 30 days prior to entry into the study or would concomitantly participate in such a study; (14) patients unable to communicate or cooperate with the Investigator due to language problems, poor mental development or impaired cerebral function.

As of the end of September 2008, there were 32 of 60 patients enrolled in this study. All but one patient was receiving insulin and standard-of-care oral antihyper-glycemics.

Figure 6:
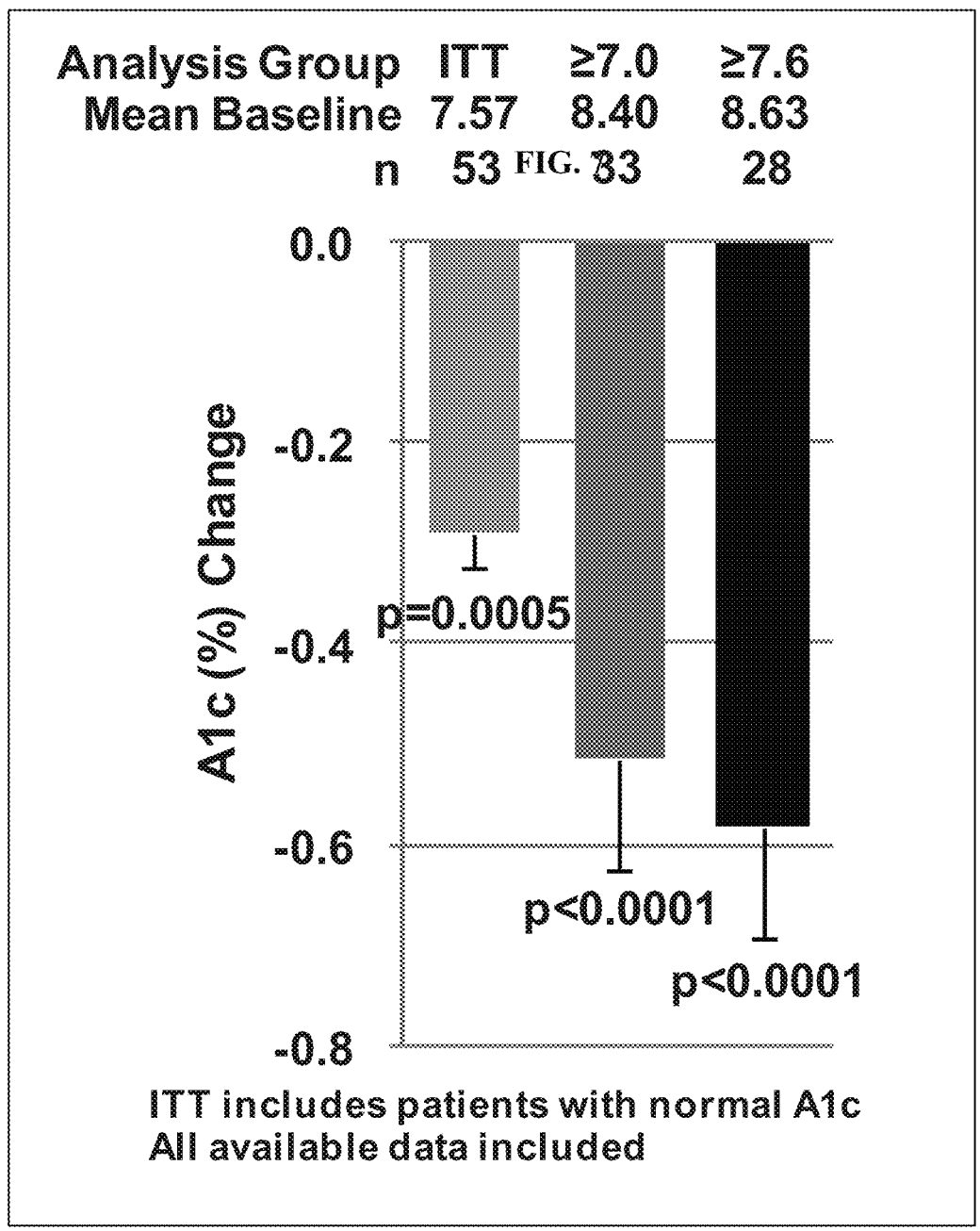
FIG. 6—RTA 402 Activity Correlates with Severity. Reduction of hemoglobin A1c is presented as a fraction of the initial baseline value. Groups with higher baselines, e.g., mean baseline ≥7.0% A1c or ≥7.6% A1c, showed greater reduction. The intent-to-treat (ITT) group includes all patients (n=53), including those starting at a normal A1c value.
Figure 7:
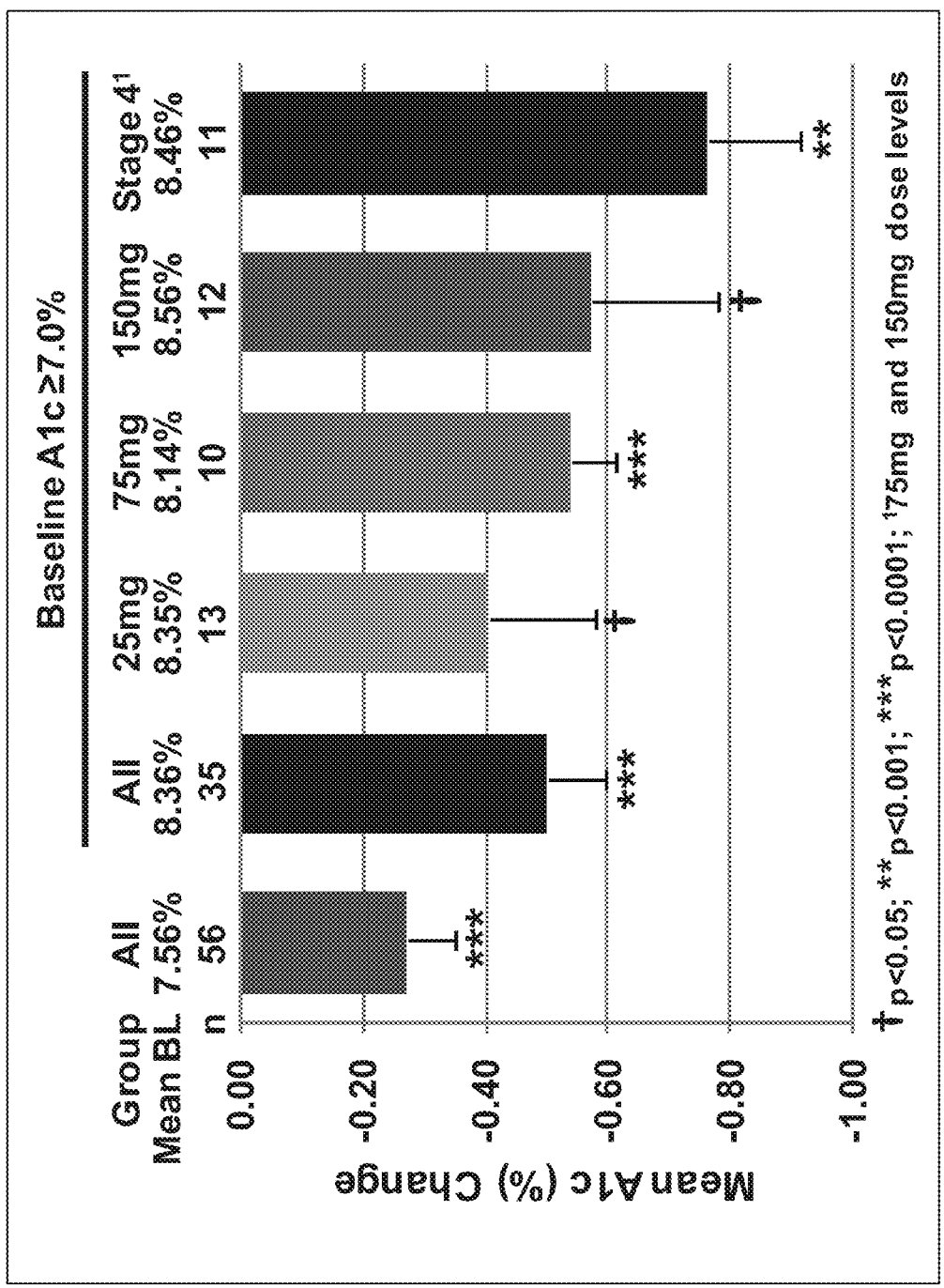
FIG. 7—RTA 402 Activity is Dose Dependent. Reduction of hemoglobin A1c is presented relative to the initial baseline value. The bar graph shows mean results for all patients, all patients with baseline A1c values ≥7.0%, individual dose cohorts from the ≥7.0% group, and patients with Stage 4 renal disease (GFR 15-29 mL/min), wherein n is the number of patients in each group.

Treatment with RTA 402 was observed to reduce hemoglobin % A1c in 28 days in refractory diabetics on top of standard of care. The treatment showed an intent-to-treat reduction of approximately 0.25 (n=56) and an elevated baseline (≥7.0 at baseline) reduction of 0.50 (n=35). Hemoglobin % A1c reduction as a function of baseline severity is shown in FIG. 6, and reduction as a function of dosage is shown in FIG. 7. Patients with advanced (Stage 4) renal disease (GFR from 15-29 ml/min) showed a mean % A1c reduction of approximately 0.77. All reductions were statistically significant.

Hyperinsulinemic euglycemic clamp test results showed that the 28 day treatment also improved glycemic control and insulin sensitivity in the patients, as measured by glucose disposal rate (GDR). Patients exhibited improvements in GDR after the 28 day treatment, with more severely impaired patients (GDR <4) showing statistically significant improvements (p≤0.02). The hyperinsulinemic euglycemic clamp test was performed at Baseline (Day −1) and at the end of the study on Day 28. The test measures the rate of glucose infusion (GINF) necessary to compensate for an increased insulin level without causing hypoglycemia; this value is used to derive the GDR.

In short, the hyperinsulinemic euglycemic clamp test takes about 2 hours. Through a peripheral vein, insulin is infused at 10-120 mU per m$^2$ per minute. In order to compensate for the insulin infusion, glucose 20% is infused to maintain blood sugar levels between 5 and 5.5 mmol/L. The rate of glucose infusion is determined by checking the blood sugar levels every 5 to 10 minutes. The rate of glucose infusion during the last 30 minutes of the test is used to determine insulin sensitivity as determined by the glucose metabolism rate (M) in mg/kg/min.

The following protocol guidelines are in place for the hyperinsulinemic euglycemic clamp test:
1) Subject to fast 8-10 hours prior to the clamp procedure.
2) The morning of the clamp measure vital signs and weight.
3) Start a retrograde line in one hand with 1¼", 18-20 gauge catheter for drawing samples.
4) Prepare IV tubing with 2 three-way stop cocks and j-loop extension tubing. Spike tubing to a liter bag of 0.9% NaCl to run at KVO (keep vein open, about 10 cc/hr) until the start of the procedure.
5) Apply a heating pad covered in a pillow case with a pad separating the heating pad from the subject's hand. (Enables the collection of shunted arterialized blood from venous catheterization)
6) Monitor the temperature (approximately 150° F./65° C.) generated by the heating pad before and during the clamp, to maintain arterialization.
7) Start another line opposite the draw side in the distal forearm with 1¼", 18-20 gauge catheter for the infusion line. Prepare IV tubing with 2 three-way stop cocks.
8) Hang a 500 ml bag of 20% dextrose and attach to port on the infusion side 9) Prepare the insulin infusion
   a. Remove 53 cc (50 cc of overfill) of saline from a 500 cc bag of 0.9% NaCl and discard
   b. Draw 8 cc of blood from subject using sterile technique and inject into a tiger top tube
   c. Centrifuge the tiger top tube. Withdraw 2 cc of serum and inject into the 500 cc bag of 0.9% NaCl
   d. Add 100 units of insulin to the bag with the serum and mix well (0.2 U insulin/ml)
   e. Connect IV tubing with duo-vent spike into the 0.9% NaCl bag
   f. Place on Baxter pump
10) Time and draw all basal blood samples (Baseline fasting blood glucose values will be obtained prior to beginning the insulin prime).
11) Perform insulin infusion rate calculations for a priming dose and 60 mU/m$^2$ insulin infusion. This background insulin is to suppress endogenous hepatic glucose production. Lean subjects can be suppressed with 40 mU/m$^2$; obese, insulin resistant subjects require 80 mU/m$^2$. 60 mU/m$^2$ should be sufficient to suppress the suggested study population with a BMI of 27-40 kg/m$^2$. The suggested 60 mU/m$^2$ insulin infusion may need to be adjusted if the BMI is amended.
12) 0.5 mL samples will be drawn every five minutes and the readings from the YSI Blood Glucose Analyzer will be used to determine/adjust the glucose infusion rate (mg/kg/min). Any additional laboratory tests required by the protocol will be in addition to the blood volume. The clamp will last 120 minutes which is believed to be a sufficient duration for determining insulin sensitivity.
13) Label and save all YSI printouts for source documents.
14) The glucose infusion rates from the last 30 minutes of the euglycemic clamp will be adjusted using space correction. This will be used to determine the glucose metabolism rate (M mg/kg/min), which represents the subject's sensitivity to insulin.

Figure 8:
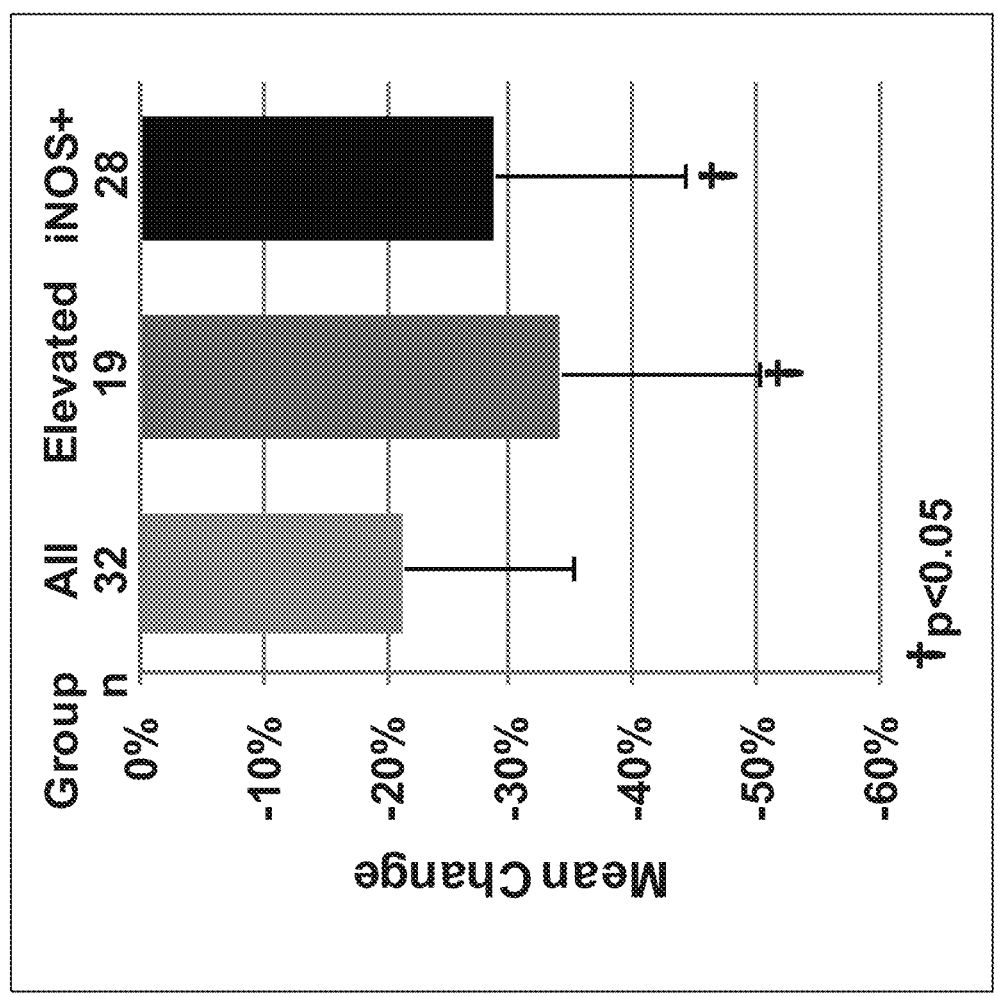
FIG. 8—RTA 402 Reduces Circulating Endothelial Cells (CECs) and iNOS-positive CECs. The change in the mean number of CECs in cells/mL is shown for intent-to-treat (ITT) and elevated baseline groups, both before and after the 28 day RTA treatment. The reduction for the Intent-to-treat group was approximately 20%, and the reduction in the elevated baseline group (>5 CECs/ml) was approximately 33%. The fraction of iNOS-positive CECs was reduced approximately 29%.

As shown in FIG. 8, RTA 402 reduces circulating endothelial cells (CECs). The mean number of CECs in cells/mL is shown for intent-to-treat (ITT) and elevated baseline groups, both before and after the 28 day RTA treatment. The reduction for the Intent-to-treat group was approximately 20%, and the reduction in the elevated baseline group (>5 CECs/ml) was approximately 33%. The fraction of iNOS-positive CECs was reduced approximately 29%. Normalization of CEC values (≤5 cells/mL) was observed in 11 out of the 19 patients with elevated baseline.

CECs were isolated from whole blood by using CD146 Ab (an antibody to the CD146 antigen that is expressed on endothelial cells and leukocytes). After CEC isolation, a FITC (fluorescein isothiocyanate) conjugated CD105 Ab (a specific antibody for endothelial cells) is used to identify CECs using the CellSearch™ system. A fluorescent conjugate of CD45 Ab was added to stain the leukocytes, and these were then gated out. For a general overview of this method, see Blann et al., (2005), which is incorporated herein by reference in its entirety. CEC samples were also assessed for the presence of iNOS by immunostaining. Treatment with RTA 402 reduced iNOS-positive CECs by approximately 29%, further indicating that RTA 402 reduces inflammation in endothelial cells.

Figure 10:
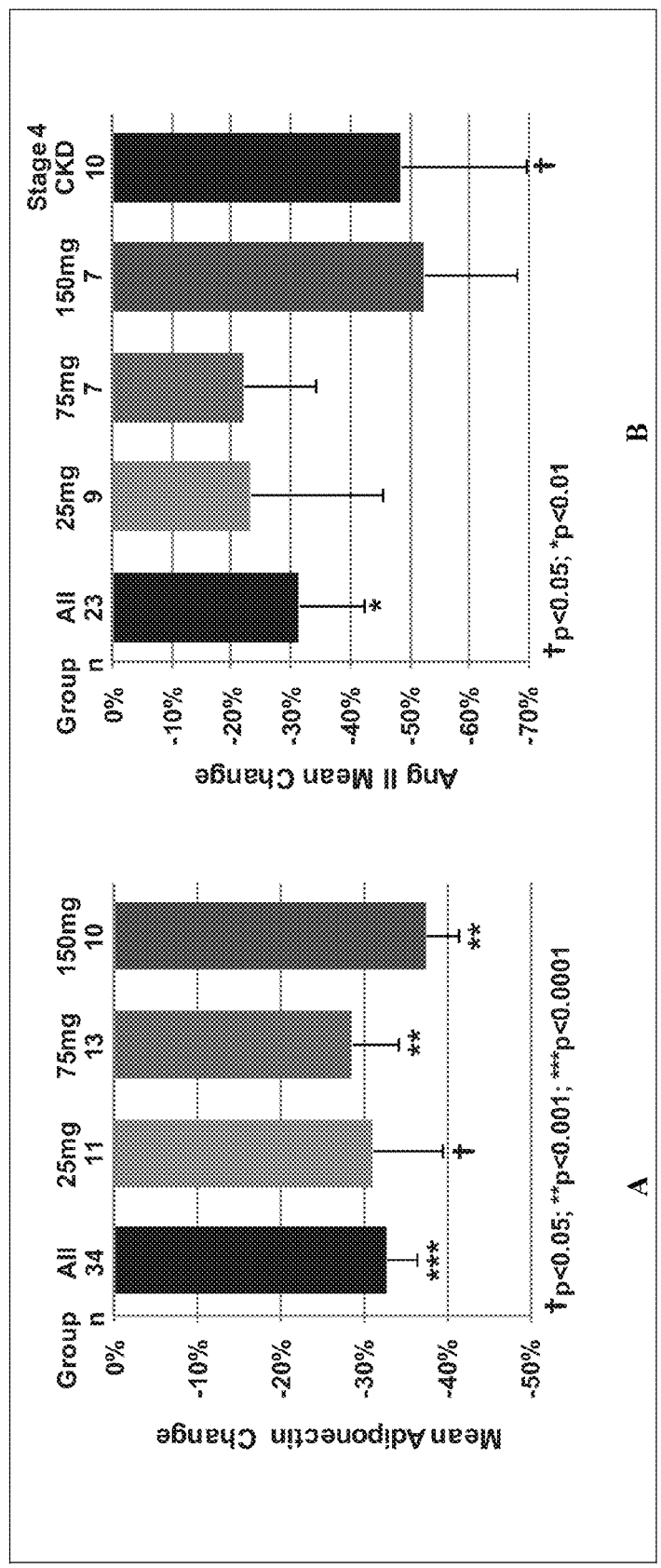
FIGS. 10A-B—Reduction of Markers of Diabetic Nephropathy Severity and Outcome. Improvements in Adiponectin (FIG. 10A) and Angiotensin II (FIG. 10B), which are elevated in diabetic nephropathy (DN) patients and correlate with renal disease severity. Adiponectin predicts all-cause mortality and end stage renal disease in DN patients. All available data included.
Figure 11:
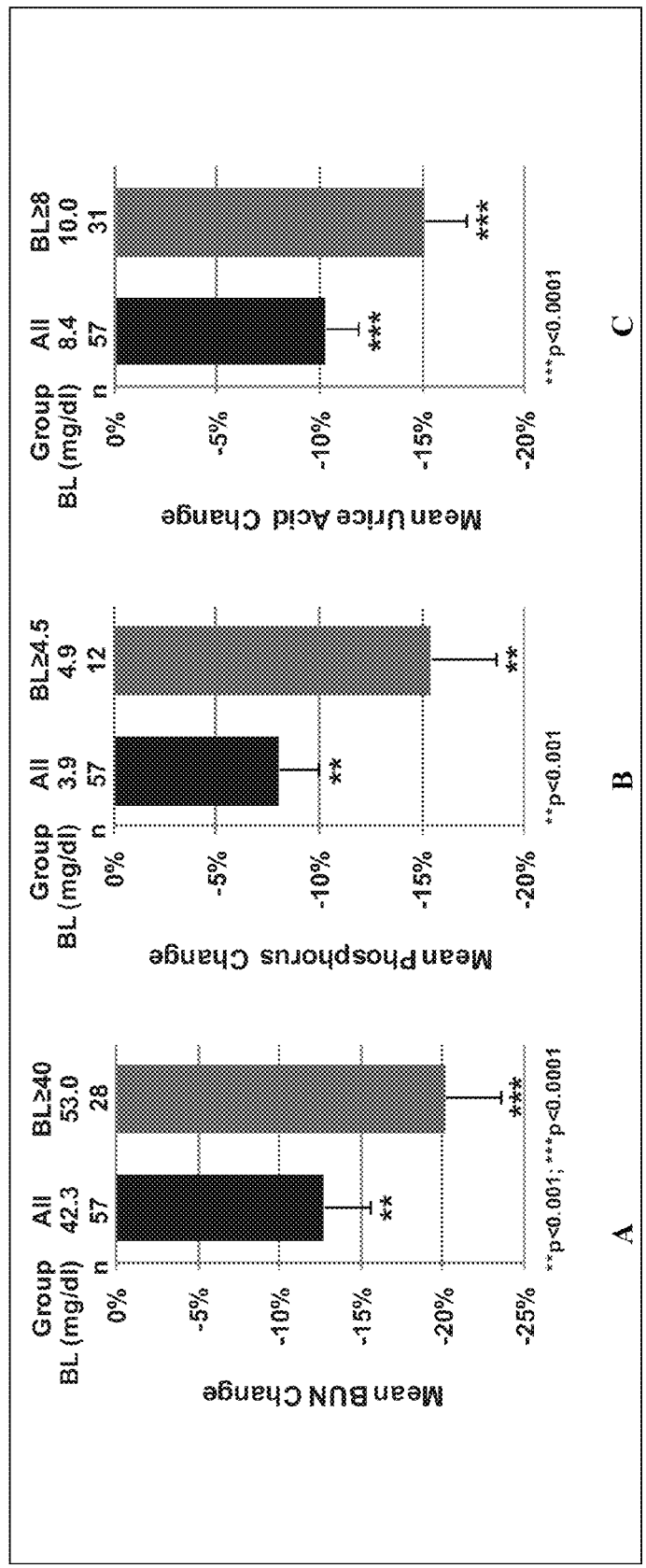
FIGS. 11A-C—RTA 402 Significantly Reduces Uremic Solutes. The graphs present mean changes in BUN (FIG. 11A), phosphorus (FIG. 11B), and uric acid (FIG. 11C) for all patients and for those patients showing elevated baseline values of a particular solute.

RTA 402 was shown to improve significantly eight measures of renal function and status, including serum creatinine based eGFR (FIG. 9), creatinine clearance, BUN (FIG. 11A), serum phosphorus (FIG. 11B), serum uric acid (FIG. 11C), Cystatin C, Adiponectin (FIG. 10A), and Angiotensin II (FIG. 10B). Adiponectin predicts all-cause mortality and end stage renal disease in DN patients. Adiponectin and Angiotensin II, which are elevated in DN patients, correlate with renal disease severity (FIGS. 10A-B). Effects on BUN, phosphorus, and uric acid are shown in FIGS. 11A-C.

Patients treated with higher doses (75 or 150 mg) of RTA 402 showed modest elevations (approximately 20 to 25%) in proteinuria. This is consistent with studies indicating that better GFR performance correlates with increased proteinuria. For example, in a long-term clinical study of more than 25,000 patients, treatment with ramipril (an ACE inhibitor) slowed the rate of eGFR decline more effectively than either telmisartan (an angiotensin receptor blocker) or the combination of ramipril and telmisartan (Mann et al., 2008). Conversely, proteinuria increased more in the ramipril group than in the other two groups. Major renal outcomes were also better with either drug alone than with combination therapy, although proteinuria increased least in the combination therapy group. Other studies have shown that drugs that reduce GFR, such as ACE-inhibitors, also reduce proteinuria (Lozano et al., 2001; Sengul et al., 2006). Other studies have shown that drugs that acutely increase GFR, such as certain calcium channel blockers, increase proteinuria up to 60% during short-term dosing (Agodoa et al., 2001; Viberti et al., 2002).

\* \* \*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. References

The following references, to the extent that they provide exemplary procedural or other details supplementary to those set forth herein, are specifically incorporated herein by reference.

U.S. Pat. No. 6,025,395
U.S. Pat. No. 6,326,507
U.S. Pat. No. 6,974,801
U.S. Patent Prov. 60/955,939
U.S. patent application Ser. No. 12/191,176
Agodoa et al., *JAMA*, 285:2719-2728, 2001.
Ahmad et al., *J. Biol. Chem.*, 281:3576-3579, 2006.
Aschner et al., *Diabetes Care*, 29(12):2632-2637, 2006.
Blann et al., *Thromb. Haemost.*, 93: 228-35 (2005).
DeFronzo et al., *Am. J. Physiol.*, 237(3):E214-223, 1979.
Dinkova-Kostova et al., *Proc. Natl. Acad. Sci. USA*, 102 (12):4584-4589, 2005.
Goldstein et al., *Diabetes Care*, 30(8): 1979-1987, 2007.
Goodman et al., *Kidney Int.*, 72:945-953, 2007.
Honda et al., *Bioorg. Med. Chem. Lett.*, 12:1027-1030, 2002.
Honda et al., *Bioorg. Med. Chem. Lett.*, 19:2711-2714, 1998.
Honda et al., *Bioorg. Med. Chem. Lett.*, 9:3429-3434, 1999.
Honda et al., *J. Med. Chem.*, 43:1866-1877, 2000a.

Honda et al., *J. Med. Chem.*, 43:4233-4246, 2000b.
Honda et al., *Med. Chem. Lett.*, 7:1623-1628, 1997.
Honda et al., *Org. Biomol. Chem.*, 1:4384-4391, 2003.
Huang et al., *Cancer Res.*, 54:701-708, 1994.
Ikeda et al., *Cancer Res.*, 63: 5551-5558, 2003.
Ikeda et al., *Mol. Cancer Ther.*, 3:39-45, 2004.
Kobayashi & Yamamoto, *Antioxid. Redox. Signal.*, 7:385-394, 2005.
Liby et al., *Cancer Res.*, 65:4789-4798, 2005.
Liu, *J. Ethnopharmacol.*, 49:57-68, 1995.
Lozano et al., *Nephrol. Dial. Transplant.*, 16-[Suppl 1]:85-89, 2001.
Ma et al., *Am. J. Pathol.*, 168:1960-1974, 2006.
Mann et al., *The Lancet*, 372: 547-553, 2008.
Maines & Gibbs, *Biochem. Biophys. Res. Commun.*, 338: 568-577, 2005.
Minns et al., *Gastroenterology*, 127:119-26, 2004.
Mix et al., *Mol. Pharmacol.*, 65:309-318, 2004.
Nath, *Kidney Int.*, 70, 432-443, 2006.
Nichols, *Drug News Perspect.*, 17:99-104, 2004.
Nishino et al., *Cancer Res.*, 48:5210-5215, 1988.
Place et al., *Clin. Cancer Res.*, 9:2798-2806, 2003.
Pullman et al., *Vasc. Health Risk Manag.*, 2(3):203-212, 2006.
Repka, M A, McGinity, J W, Zhang, F, Koleng, J J, Hot-melt extrusion technology. In: *Encyclopedia of Pharmaceutical Technology*, 2$^{nd}$ ed, New York, N.Y.: Marcel Dekker, 2002: 203-206.
Sengul et al., *Diab. Res. Clin. Pract.*, 71:210-219, 2006.
Shishodia et al., *Clin. Cancer Res.*, 12(6):1828-1838, 2006.
Suh et al., *Cancer Res.*, 63:1371-1376, 2003.
Suh et al., *Cancer Res.*, 58:717-723, 1998.
Suh et al., *Cancer Res.*, 59(2):336-341, 1999.
Tumlin et al., *Am. J. Cardiol.*, 98:14K-20K, 2006.
Viberti et al., *Circulation*, 106:672-678, 2002.
Wang et al., *Mol. Endocrinol.*, 14:1550-1556, 2000.
Wardle, *Nephrol. Dial. Transplant.*, 16, 1764-1768 2001.
Wermuth and Stahl, In: *Pharmaceutical Salts: Properties, Selection and Use—A Handbook*, Verlag Helvetica Chimica Acta, 2002.
Yao et al., *Am. J. Med. Sci.*, 334(2):115-24, 2007.
Yates et al., *Mol. Cancer Ther.*, 6(1):154-162, 2007.
Yoh et al., *Kidney Int.*, 60, 1343-1353, 2001.
Zingarelli et al., *Crit Care Med.*, 31, S105-S111, 2003.
Zoccali, *J. Amer. Soc. Nephrol,.* 17:S61-S-63, 2006.

What is claimed is:

1. A method for treating renal/kidney disease (RKD), insulin resistance, diabetes, endothelial dysfunction, fatty liver disease, or cardiovascular disease (CVD) in a subject in need thereof, comprising administering to the subject a pharmaceutically effective amount of a compound of the structural formula set forth below, wherein the subject does not have cancer:

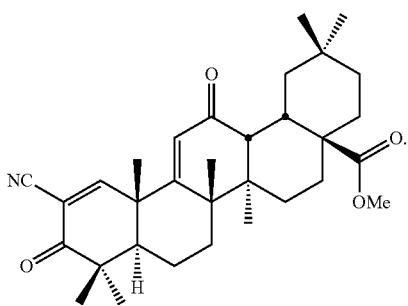

2. The method of claim 1, wherein the subject has RKD.
3. The method of claim 2, wherein the RKD is diabetic nephropathy (DN).
4. The method of claim 1, wherein the subject has insulin resistance.
5. The method of claim 1, wherein the subject has diabetes.
6. The method of claim 1, wherein the subject has CVD.
7. The method of claim 1, wherein the subject has endothelial dysfunction.
8. The method of claim 1, wherein the subject has fatty liver disease.
9. The method of either claim 1 or claim 7, further comprising identifying a subject in need of treatment of any of the listed diseases, dysfunctions, resistances or disorders.
10. The method of either claim 1 or claim 7, wherein the subject has a family or patient history of any of the listed diseases, dysfunctions, resistances or disorders.
11. The method of either claim 1 or claim 7, wherein the subject exhibits symptoms of any of the listed diseases, dysfunctions, resistances or disorders.
12. The method of either claim 1 or claim 7, wherein the subject is a primate.
13. The method of claim 12, wherein the primate is a human.
14. The method of claim 1, wherein at least a portion of the compound is present as a polymorphic form, wherein the polymorphic form is a crystalline form having an X-ray diffraction pattern (CuKα) comprising significant diffraction peaks at about 8.8, 12.9, 13.4, 14.2and 17.4 °2θ.
15. The method of claim 14, wherein the X-ray diffraction pattern (CuKα) is substantially as shown in FIG. 12A or FIG. 12B.
16. The method of claim 1, wherein at least a portion of the compound is present as a polymorphic form, wherein the polymorphic form is an amorphous form having an X-ray diffraction pattern (CuKα) with a halo peak at approximately 13.5 °2θ, substantially as shown in FIG. 12C, and a $T_g$.
17. The method of claim 16, wherein the $T_g$ value is in the range of about 120° C. to about 135° C.
18. The method of claim 17, wherein the $T_g$ value is in the range of about 125° C. to about 130° C.
19. The method according to claim 1, wherein the compound is formulated as a pharmaceutical composition comprising (i) a therapeutically effective amount of the compound and (ii) an excipient, wherein the excipient is (A) a carbohydrate, carbohydrate derivative, or carbohydrate polymer, (B) a synthetic organic polymer, (C) an organic acid salt, (D) a protein, polypeptide, or peptide, or (E) a high molecular weight polysaccharide.
20. The method of claim 19, wherein the excipient is a synthetic organic polymer.
21. The method of claim 20, wherein the excipient is selected from the group consisting of a hydroxypropyl methyl cellulose, a poly[1-(2-oxo-1pyrrolidinyl)ethylenel] or copolymer thereof, and a methacrylic acid-methylmethacrylate copolymer.
22. The method of claim 20, wherein the excipient is hydroxypropyl methyl cellulose phthalate ester.
23. The method of claim 21, wherein the excipient is PVP/VA.
24. The method of claim 20, wherein the excipient is a methacrylic acid-ethyl acrylate copolymer (1:1).

25. The method of claim 20, wherein the excipient is copovidone.

* * * * *

UNITED STATES PATENT AND TRADEMARK OFFICE
CERTIFICATE OF CORRECTION

PATENT NO. : 9,757,359 B2  
APPLICATION NO. : 13/886053  
DATED : September 12, 2017  
INVENTOR(S) : Michael B. Sporn et al.

Page 1 of 1

It is certified that error appears in the above-identified patent and that said Letters Patent is hereby corrected as shown below:

In the Claims

In Claim 14, Column 44, Line 30, delete "14.2and" and replace with --14.2 and-- therefor.

In Claim 21, Column 44, Line 56, delete "poly[1-(2-oxo-1pyrrolidinyl)ethylenel]" and replace with --poly[1-(2-oxo-1-pyrrolidinyl)ethylene]-- therefor.

Signed and Sealed this
Seventh Day of August, 2018

Andrei Iancu
*Director of the United States Patent and Trademark Office*